United States Patent
Tse et al.

(10) Patent No.: US 7,572,816 B2
(45) Date of Patent: Aug. 11, 2009

(54) THERAPEUTIC AGENTS FOR THE TREATMENT OF CANCER, METABOLIC DISEASES AND SKIN DISORDERS

(75) Inventors: Bruno Tse, San Diego, CA (US); Sepehr Sarshar, Cardiff by the Sea, CA (US)

(73) Assignee: Auspex Pharmaceuticals, Inc., Vista, CA (US)

( * ) Notice: Subject to any disclaimer, the term of this patent is extended or adjusted under 35 U.S.C. 154(b) by 599 days.

(21) Appl. No.: 10/514,383

(22) PCT Filed: Jul. 21, 2004

(86) PCT No.: PCT/US2004/023562

§ 371 (c)(1),
(2), (4) Date: Jul. 14, 2005

(87) PCT Pub. No.: WO2005/011573

PCT Pub. Date: Feb. 10, 2005

(65) Prior Publication Data

US 2006/0014800 A1    Jan. 19, 2006

(51) Int. Cl.
| | | |
|---|---|---|
| *A61K 31/47* | (2006.01) | |
| *A61K 31/425* | (2006.01) | |
| *A61K 31/415* | (2006.01) | |
| *C07D 295/00* | (2006.01) | |
| *C07D 207/00* | (2006.01) | |
| *C07D 401/00* | (2006.01) | |
| *C07D 233/00* | (2006.01) | |
| *C07D 277/00* | (2006.01) | |
| *C07D 409/00* | (2006.01) | |
| *C07D 403/00* | (2006.01) | |
| *C07D 239/02* | (2006.01) | |
| *C07D 215/02* | (2006.01) | |
| *C07D 271/00* | (2006.01) | |
| *C07D 285/02* | (2006.01) | |
| *C07D 257/04* | (2006.01) | |
| *C07D 487/00* | (2006.01) | |

(52) U.S. Cl. .................. 514/341; 514/277; 514/336; 514/340; 514/359; 514/365; 514/369; 514/371; 514/374; 514/376; 514/383; 514/385; 548/530; 548/300.1; 548/316.4; 548/317.1; 548/321.1; 548/146; 548/182; 548/183; 548/185; 548/131; 548/125; 548/250; 548/262.2; 548/266.2; 548/266.4; 548/190; 548/191; 548/356.1; 548/364.1; 546/268.1; 546/276.4; 546/278.4; 546/278.7; 546/112; 546/152; 546/165; 546/166; 546/181; 544/224; 544/238; 544/240; 544/242; 544/309; 544/310; 544/312

(58) Field of Classification Search ............ 514/277, 514/336, 340, 341, 359, 365, 369, 371, 374, 514/376, 383, 385; 544/224, 238, 240, 242, 544/298, 309, 310, 312; 546/268.1, 276.4, 546/278.4, 278.7, 112, 152, 165, 166, 181; 548/530, 300.1, 316.4, 317.1, 321.1, 146, 548/182, 183, 185, 125, 250
See application file for complete search history.

(56) References Cited

U.S. PATENT DOCUMENTS

2004/0122059 A1*  6/2004  Cantorna et al. ............ 514/342

OTHER PUBLICATIONS

"Cellular Processes." Retrieved via the Internet [Jul. 15, 2008] URL: http://en.wikipedia.org/wiki/Category:Cellular_processes.*
"Cancer." Retrieved via the Internet [Jul. 15, 2008] URL: http://www.nlm.nih.gov/medlineplus/cancer.html.*
Golub et al. Science (1999), vol. 286 521-537.*
Lala et al. Cancer and Metastasis Reviews (1998), 17(1), 91-106.*

* cited by examiner

*Primary Examiner*—Kamal A Saeed
*Assistant Examiner*—Samantha L Shterengarts
(74) *Attorney, Agent, or Firm*—Dennis A. Bennett; Michael Sertic

(57) ABSTRACT

The present invention is directed to compounds having the structure wherein $R_1$, $R_2$, $R_3$, $R_4$, $R_5$ and m are as defined herein. The compounds of this invention are novel therapeutic agents for the treatment of cancer, metabolic diseases and skin disorders in mammalian subjects. These compounds are also useful modulators of gene expression. They exert their activity by interfering with certain cellular signal transduction cascades. The compounds of the invention are thus also useful for regulating cell differentiation and cell cycle processes that are controlled or regulated by various hormones or cytokines. In particular, the invention relates to compounds that induce apoptosis of cancer cells and therefore may be used for the treatment or prevention of cancer, including advanced cancers and pre-cancerous cells. The invention also discloses pharmaceutical compositions and methods of treatment of disease in mammals

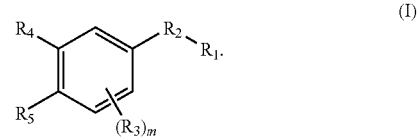

(I)

8 Claims, 9 Drawing Sheets

THERAPEUTIC AGENTS FOR THE TREATMENT OF CANCER, METABOLIC DISEASES AND SKIN DISORDERS

FIELD OF INVENTION

The invention relates generally to a novel class of retinoids and more specifically to methods of preparation, pharmaceutical compositions, and methods of disease treatment utilizing pharmaceutical compositions comprising these compounds.

BACKGROUND OF THE INVENTION

Cancer is a complex disease characterized by genetic mutations that lead to uncontrolled cell growth. Cancerous cells are present in all organisms and under normal circumstances their excessive growth is tightly regulated by various physiological factors. One such regulatory process is apoptosis or programmed cell death. When the internal machinery of a cell detects abnormalities in cell division and growth, a signal is propagated within the cell, activating suicide proteins that kill the afflicted cell and prevent its proliferation. Such an apoptotic signal can be triggered, for example, when a ligand or drug interacts with a receptor or protein in the cell.

Most agents that induce apoptosis in cancer cells (e.g. Doxorubicin and Vincristine) are extremely toxic and cause a number of undesirable side effects. The toxicity associated with these therapies is a result of the non-specific interaction of the drug with the DNA of non-cancerous cells (e.g. intestinal and red blood cells). In order to circumvent such undesirable side effects, more selective compounds have been designed that inhibit one or more signaling proteins, growth factors and/or receptors involved in cancer cell proliferation. Examples include monoclonal antibodies for breast cancer (e.g. Herceptin) and Non-Hodgkin's Lymphoma (e.g. Rituxan), as well anti-angiogenic drugs for chronic myeloid leukemia (e.g. Gleevec). Since patient populations are genetically heterogeneous, it follows that a single selective therapy will not work in all cases, and as a result, cancer drugs are often used in combination. As such, there is a continual need for improved treatments.

Retinoids are analogs of vitamin A and regulate cell growth, differentiation, and apoptosis. Retinoids bind to and activate two classes of Nuclear Retinoid receptors: the retinoic acid receptors (RARα, RARβ, RARγ) and retinoic X receptors (RXRα, RXRβ, RXRγ). These receptors bind to specific sequences of DNA and thereby regulate gene expression. The RAR and RXR receptor isoforms are expressed differently during development and differentiation. These various isoforms can either homodimerize or heterodimerize leading to a variety of protein complexes that regulate different sets of retinoid-induced genes. Activation of each receptor class results in modulation of various biological functions such as cell differentiation, embryonic development, and cell proliferation. Clinical studies have shown that retinoic acid and its synthetic analogs can inhibit the growth and invasion of cancer cells, and induce them to undergo apoptosis, thereby eradicating various types of cancers.

The novel compounds of this invention modulate the activity of Nuclear Retinoid receptors. These novel compounds are thus useful for regulating cell differentiation and cell cycle processes as well as other cellular signaling processes controlled or regulated by hormones and vitamins such as the thyroid hormone, vitamin D, all-trans retinoic acid and 9-cis-retinoic acid. Hence, conditions and/or diseases that are regulated by the aforementioned entities may be treated using the compounds of this invention. Examples of such conditions include for example cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like.

Compounds that modulate the activity of RAR receptors are structural analogs of all-trans-retinoic acid. On the other hand compounds that modulate the activity of RXR receptors are structural analogs of 9-cis-retinoic acid (e.g. Bexarotene). The aforementioned modulators of Nuclear Retinoid receptors bear a carboxylic acid group in a specific position of the molecule. This acidic group forms a salt bridge to a basic residue in the binding pocket of the Nuclear Retinoid receptors. Research in this field indicates that removal of this acidic group drastically reduces the potency or the modulator. There are however, other amino acid residues in the binding pocket that can interact with the modulator. None of the modulators of Nuclear Retinoid receptors described to date take advantage of these critical interactions.

Another drawback of the current state of the art is the limited aqueous solubility of the selective Nuclear Retinoid receptor modulators. Said modulators mimic the structures of retinoic acids in order to conform to the three-dimensional structure and the hydrophobic nature of the respective binding pockets. In general, introduction of solubilizing substituents has resulted in lower in vitro binding affinity or increased in vivo metabolism and toxicity.

There exists therefore a need to improve upon the prior art in order to enhance the clinical profile of such therapeutics. Such improvements may be carried out by introducing specially designed functional groups at specific positions on the molecular backbone of the modulator. The novel compounds of this invention address this issue and display enhanced in vitro profiles when compared to compounds of the prior art.

BREIF DESCRIPTION OF THE FIGURES

FIG. 1 depicts the growth inhibitory effect of 4 compounds on human melanoma cells (A375). The figure clearly shows the enhanced activity of example 8, example 10 and example 11 when compared to Bexarotene (4-[1-(3,5,5,8,8-pentamethyl-5,6,7,8-tetrahydro-naphthalen-2-yl)-vinyl]-benzoic acid).

FIG. 2 depicts the growth inhibitory effect of 4 compounds on human melanoma cells (A375). The figure clearly shows the enhanced activity of example 12, example 13 and example 14 when compared to Bexarotene (4-[1-(3,5,5,8,8-pentamethyl-5,6,7,8-tetrahydro-naphthalen-2-yl)-vinyl]-benzoic acid).

Figure 1:
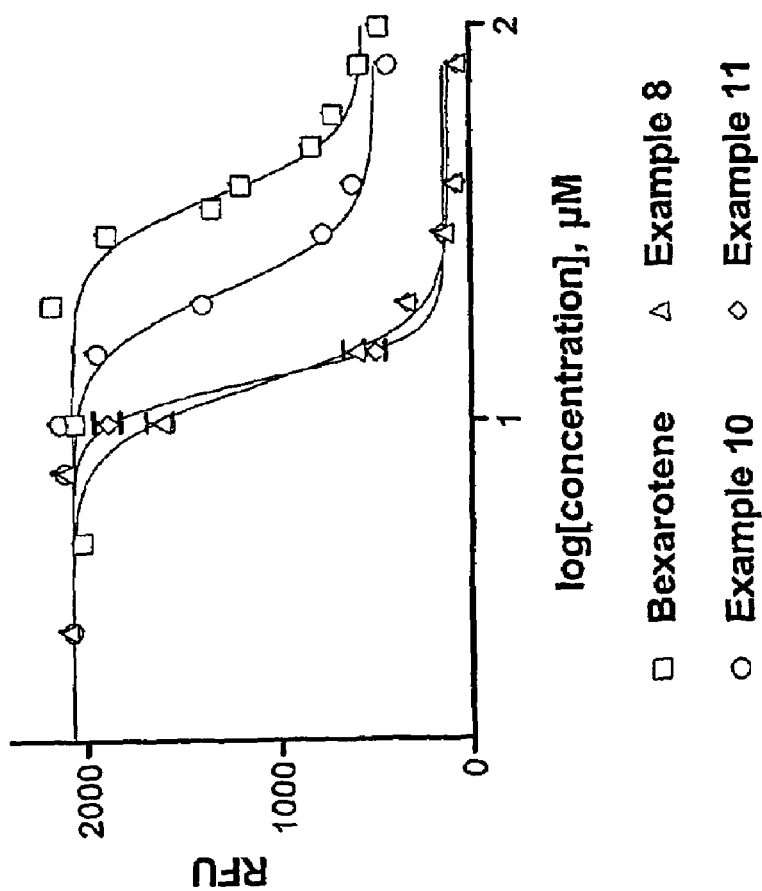
Figure 2:
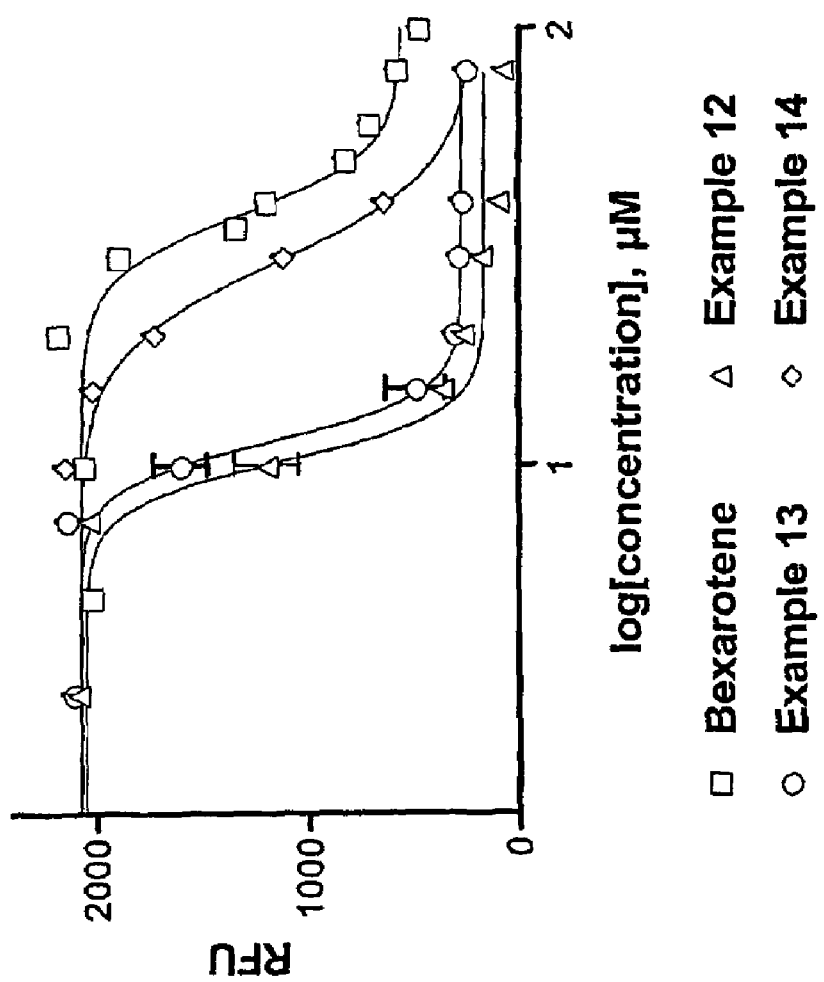
Figure 3:
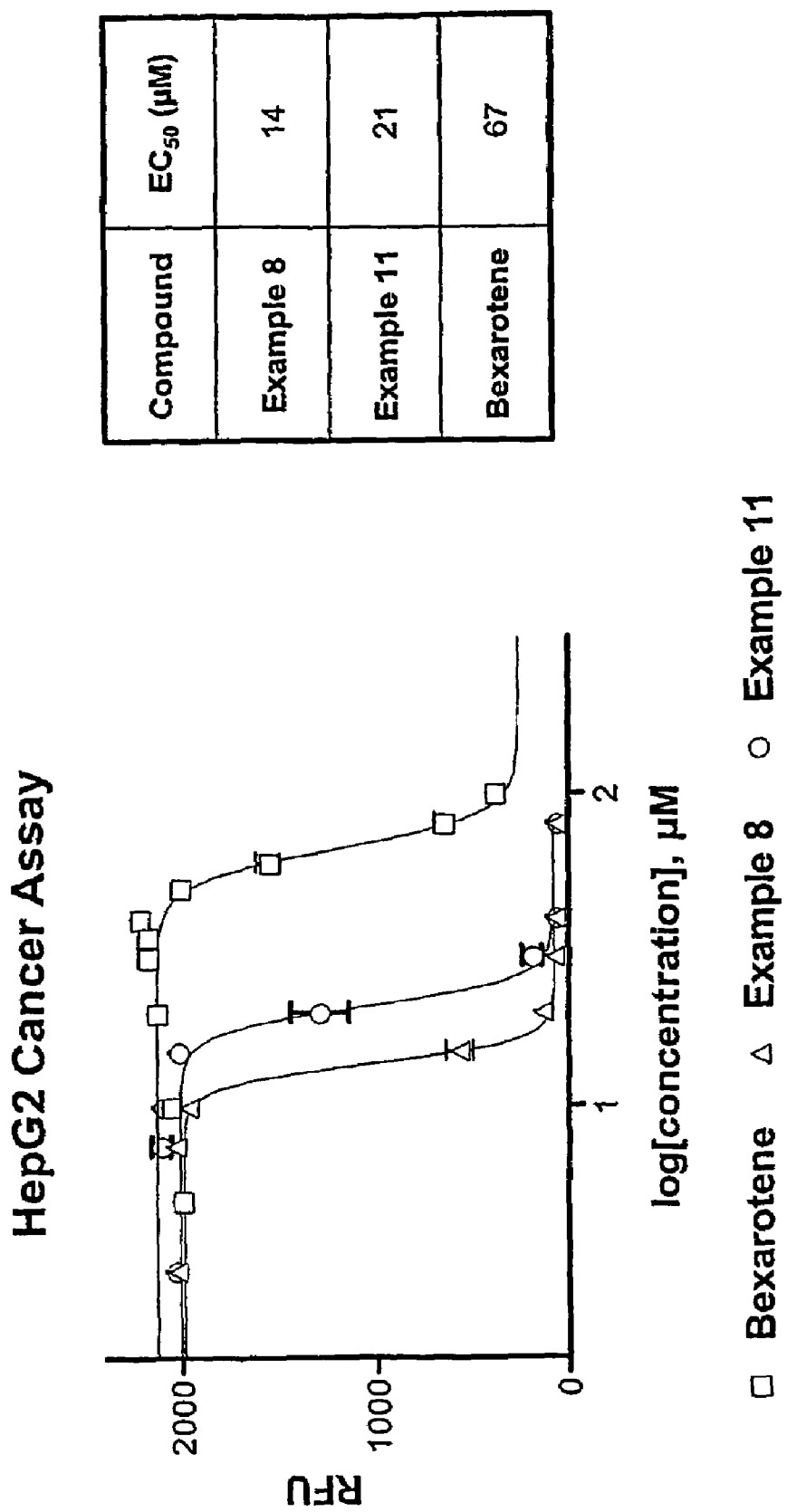
FIG. 3 depicts the growth inhibitory effect of 3 compounds on human hepatic carcinoma cells (HepG2). The figure clearly shows the enhanced activity of example 8, and example 11 when compared to Bexarotene (4-[1-(3,5,5,8,8-pentamethyl-5,6,7,8-tetrahydro-naphthalen-2-yl)-vinyl]-benzoic acid).
Figure 4:
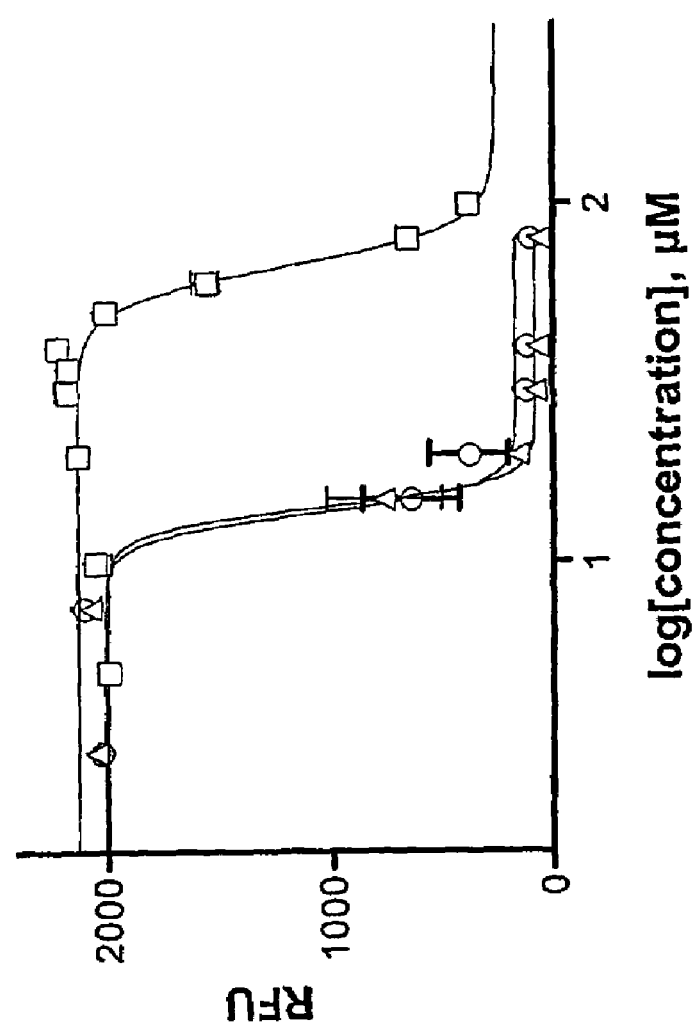
FIG. 4 depicts the growth inhibitory effect of 3 compounds on human hepatic carcinoma cells (HepG2). The figure clearly shows the enhanced activity of example 12, and example 13 when compared to Bexarotene (4-[1-(3,5,5,8,8-pentamethyl-5,6,7,8-tetrahydro-naphthalen-2-yl)-vinyl]-benzoic acid).
Figure 5:
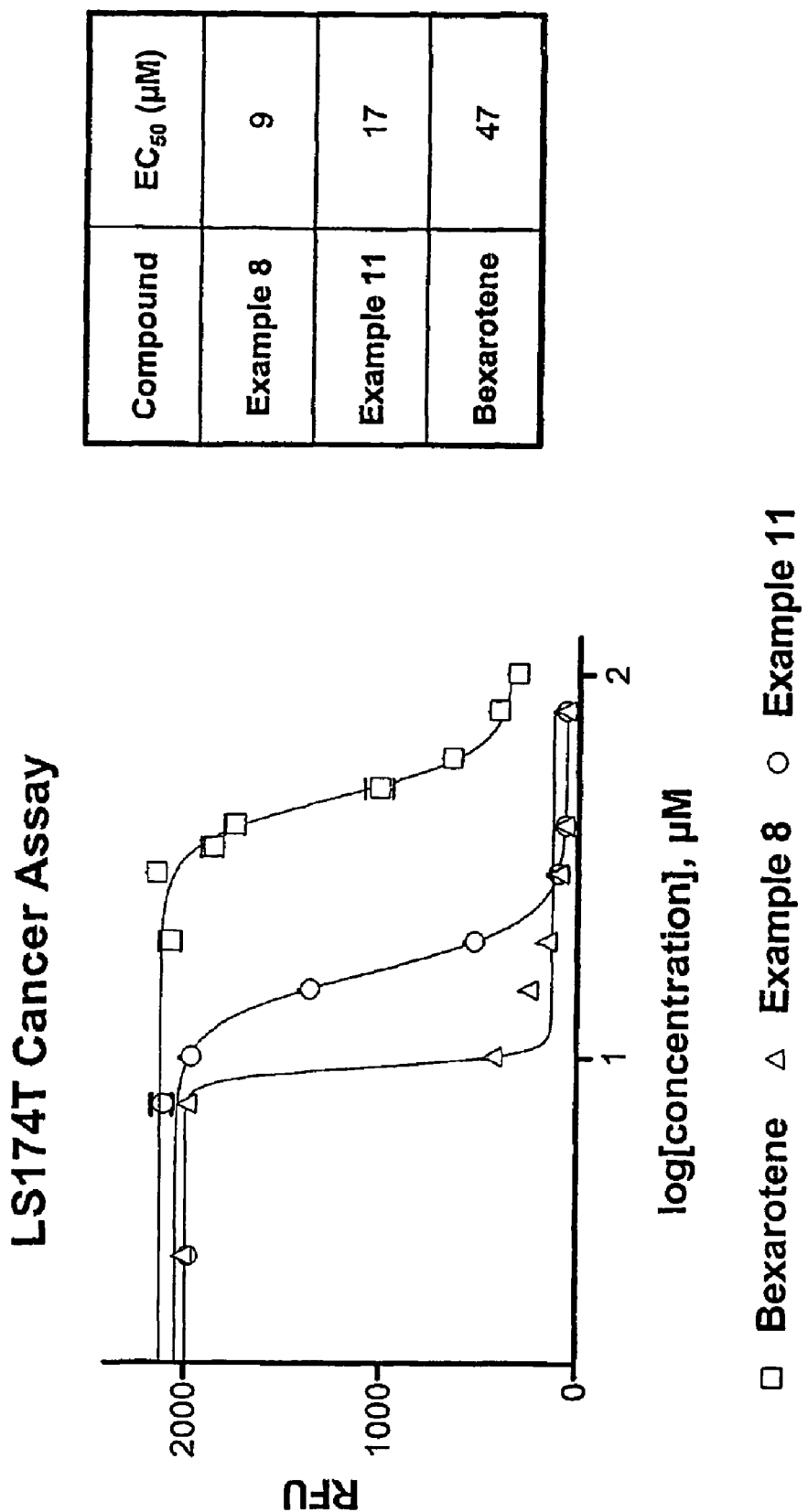
FIG. 5 depicts the growth inhibitory effect of 3 compounds on human colon cancer cells (LS174T). The figure clearly shows the enhanced activity of example 8 and example 11 when compared to Bexarotene (4-[1-(3,5,5,8,8-pentamethyl-5,6,7,8-tetrahydro-naphthalen-2-yl)-vinyl]-benzoic acid).
Figure 6:
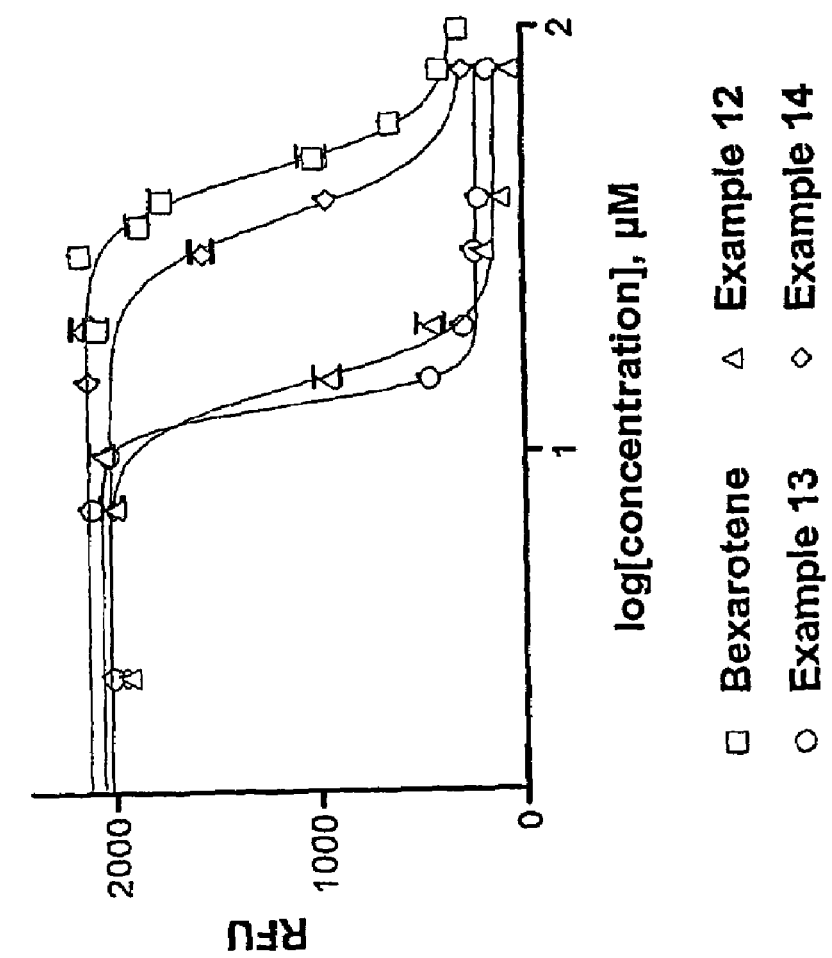

FIG. 6 depicts the growth inhibitory effect of 4 compounds on human colon cancer cells (LS174T). The figure clearly shows the enhanced activity of example 12, example 13 and example 14 when compared to Bexarotene (4-[1-(3,5,5,8,8-pentamethyl-5,6,7,8-tetrahydro-naphthalen-2-yl)-vinyl]-benzoic acid).

Figure 7:
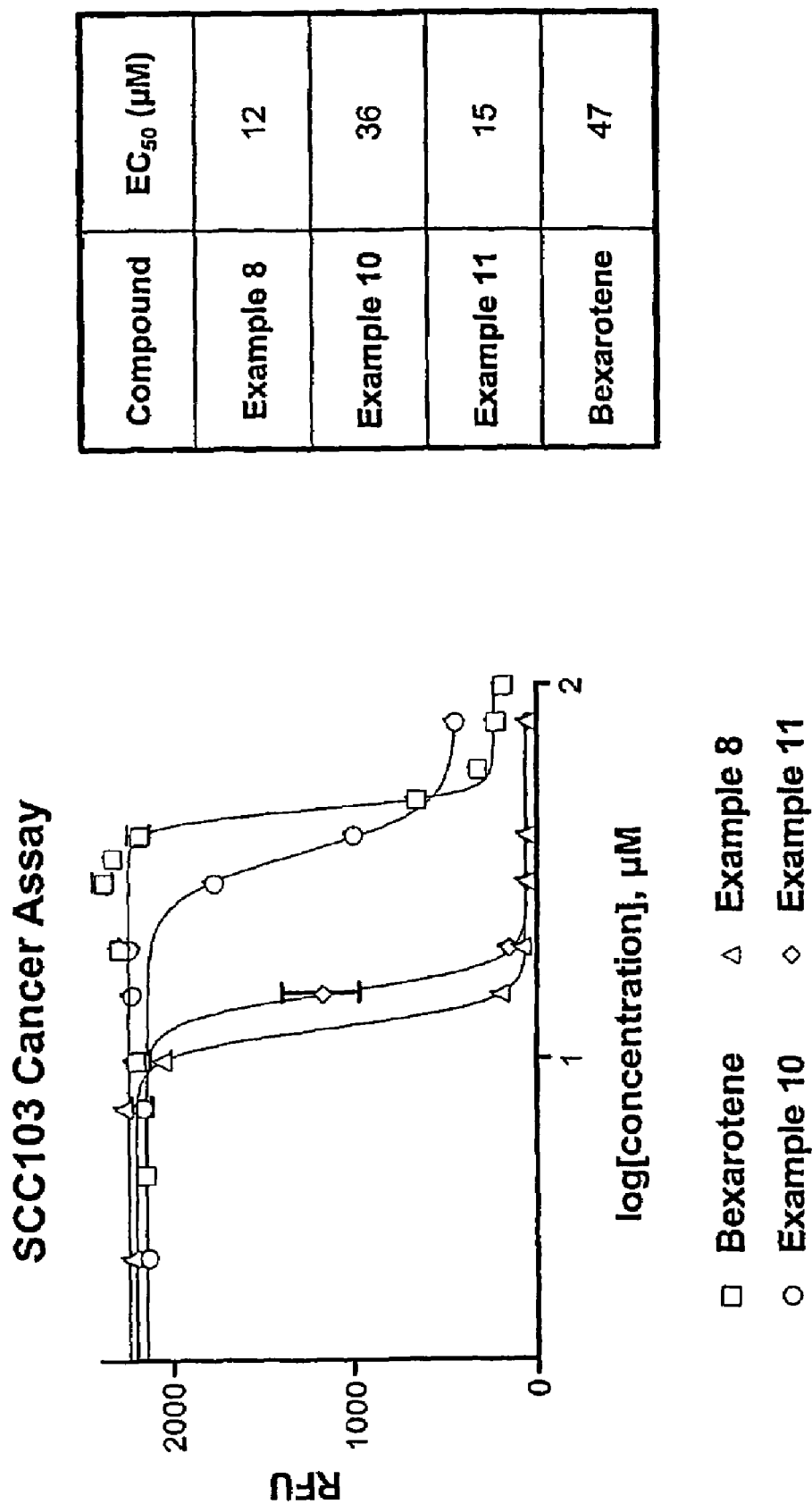

FIG. 7 depicts the growth inhibitory effect of 4 compounds on human head and neck squamous cell carcinoma cells (SCC 103). The figure clearly shows the enhanced activity of example 8, example 10 and example 11 when compared to Bexarotene (4-[1-(3,5,5,8,8-pentamethyl-5,6,7,8-tetrahydro-naphthalen-2-yl)-vinyl]-benzoic acid).

Figure 8:
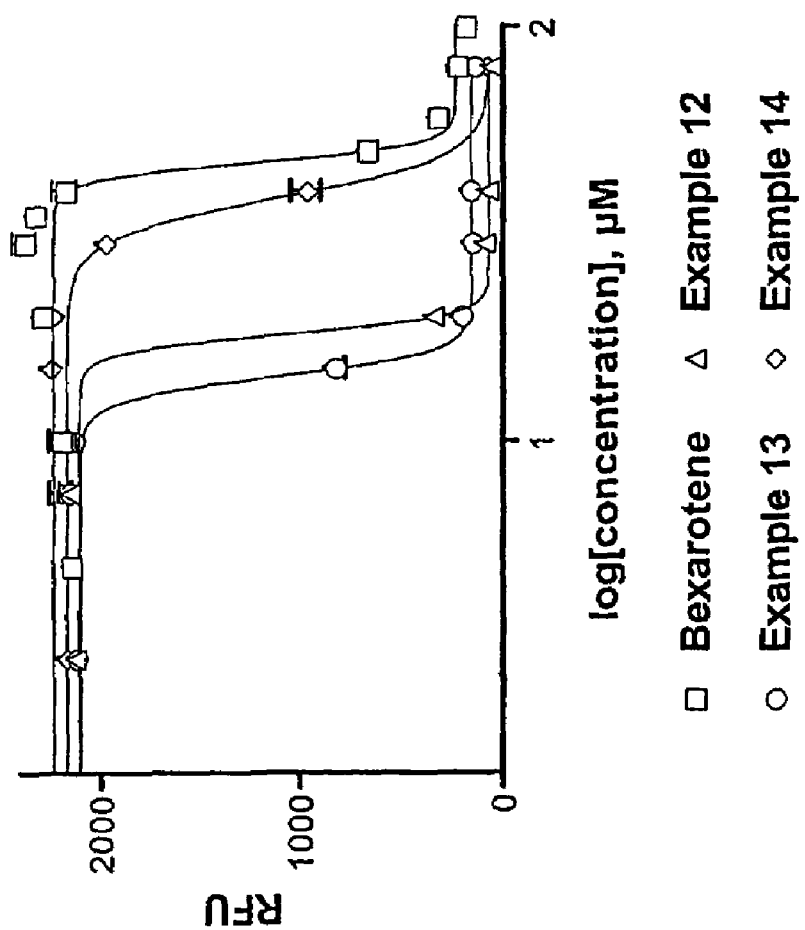

FIG. 8 depicts the growth inhibitory effect of 4 compounds on human head and neck squamous cell carcinoma cells (SCC 103). The figure clearly shows the enhanced activity of example 12, example 13 and example 14 when compared to Bexarotene (4-[1-(3,5,5,8,8-pentamethyl-5,6,7,8-tetrahydro-naphthalen-2-yl)-vinyl]-benzoic acid).

Figure 9:
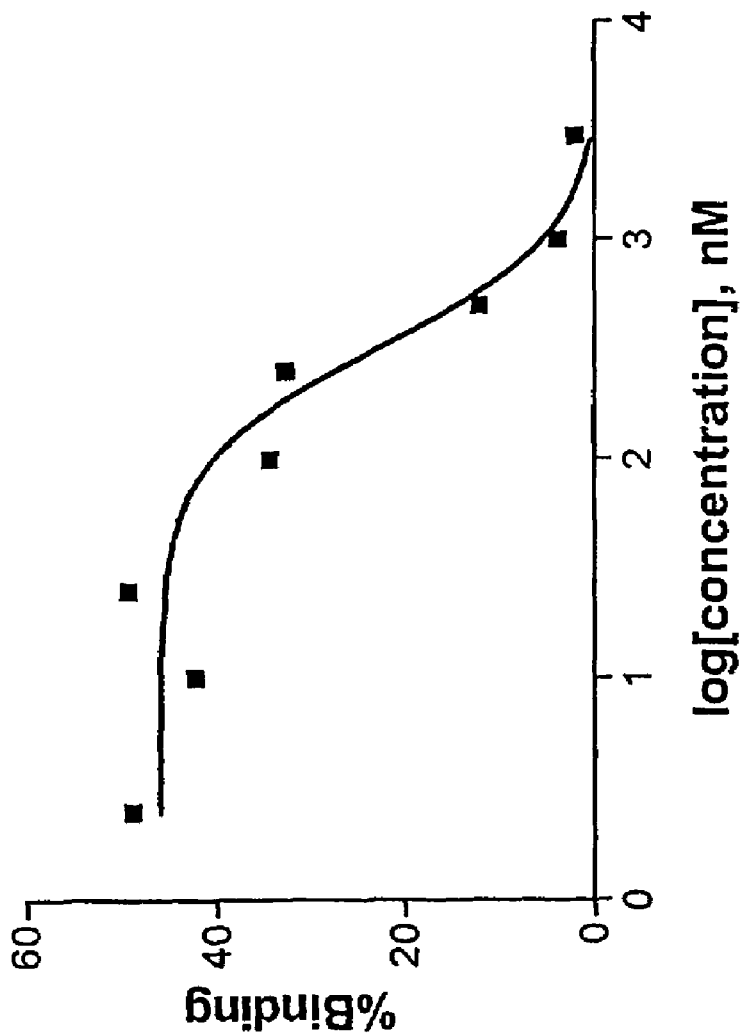

FIG. 9 depicts the binding affinity of example 8 to RXRγ

SUMMARY OF THE INVENTION

The invention provides novel therapeutic agents for the treatment of cancer, metabolic diseases and skin disorders in mammalian subjects. These novel agents bear specially designed functional groups at specific positions on the molecular backbone of the modulator. These modifications provide additional interactions between the compounds of this invention and certain amino acid residues in the binding pocket of the Retinoid Nuclear receptors. As a result, the compounds of this invention show enhanced in vitro profiles when compared to previously known compounds.

The invention also provides novel compounds that interact with one or more cellular receptors and are useful in the modulation of gene expression.

Furthermore, the invention also provides novel compounds that are useful in controlling cell cycle, and cell differentiation processes regulated by certain hormones, such as for example the thyroid hormone and the like, and/or certain vitamins, such as for example vitamin D and the like, and/or certain retinoids, such as for example 9-cis-retinoic acid and the like.

Furthermore, the invention also provides novel compounds that are useful in inducing apoptosis in mammalian cells.

Furthermore, the invention also provides novel chemical compositions and discloses synthetic methodologies to prepare the same.

In one aspect the invention relates to novel compounds comprising the structural formula A

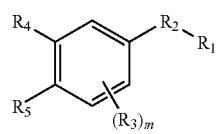

wherein:

$R_1$ is

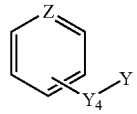

Z is selected from the group comprising CH, and nitrogen; $Y_4$ is selected from the group comprising substituted or unsubstituted $C_{1-6}$ alkyl, $C_{1-6}$ alkyl, $C_{0-5}$ alkyloxy-$C_{0-5}$ alkyl, $C_{0-5}$ alkylthio-$C_{0-5}$ alkyl, and $C_{0-5}$ alkylamino-$C_{0-5}$ alkyl; Y can be attached to any position on $Y_4$ and Y is selected from the group comprising cyano, —COOR$_{21}$, —CONR$_{22}$R$_{23}$, —CONR$_{21}$NR$_{22}$R$_{23}$, heteroaryl, formulae A$_1$, A$_2$, A$_3$, A$_4$, A$_5$,

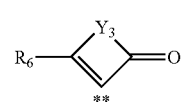

A1

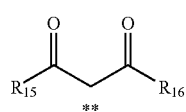

A2

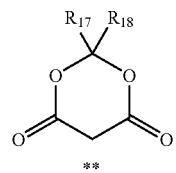

A3

A4

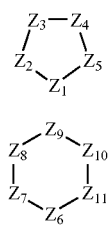

A5

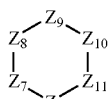

wherein:

$Y_3$ is selected from the group comprising $C_{2-8}$ alkyl, and $C_{2-8}$ substituted alkyl; $Z_2$, $Z_5$, $Z_7$ and $Z_{11}$ are independently selected from the group comprising C=O, C=S, C=NR$_{17}$, C=NNR$_{22}$R$_{23}$, C=NOR$_{17}$, and CR$_{24}$R$_{25}$; $Z_1$, $Z_3$, $Z_4$, $Z_6$, $Z_8$, $Z_9$ and $Z_{10}$ are independently selected from the group comprising O, S, N, —NH, alkylamino, arylamino, and CR$_{24}$R$_{25}$, but cannot be O or S if $Z_1$, $Z_3$, $Z_4$, $Z_6$, $Z_8$, $Z_9$ or $Z_{10}$ is the point of attachment to $Y_4$, and $Z_3$ and $Z_4$ cannot both be O at the same time, and $Z_8$ and $Z_9$ cannot both be O at the same time, and $Z_9$ and $Z_{10}$ cannot both be O at the same time, and $Z_3$, $Z_4$, $Z_8$, $Z_9$ or $Z_{10}$ can form double bonds to each other provided that none are O or S; $R_6$ is selected from the group comprising —OH, alkyloxy, aryloxy, alkylcarboxy, arylcarboxy, —SH, alkylthio, arylthio, —NH$_2$, alkylamino, arylamino, N-aryl-N-alkylamino, —NHNH$_2$, alkylhydrazino, arylhydrazino, N-aryl-N-alkylhydrazino, —NHOR$_{17}$, —O(P=O)(OR$_{17}$)(OR$_{18}$), —OCH$_2$O(P=O)(OR$_{17}$)(OR$_{18}$), and —OSO$_3$R$_{17}$; $R_{15}$ and $R_{16}$ are independently selected from the group comprising —OH, alkyloxy, aryloxy, —NH$_2$, alkylamino, arylamino, N-aryl-N-alkylamino, —NHNH$_2$, alkylhydrazino, arylhydrazino, N-aryl-N-alkylhydrazino, —NHOR$_{17}$, alkyl, and aryl; R$_{17}$ and R$_{18}$ are independently selected from the group comprising hydrogen, alkyl, and aryl; R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined herein; R$_{24}$ and R$_{25}$ are independently selected from the group comprising hydrogen, halogen, alkyl, and aryl; ** represents the point of attachment of Y to Y$_4$ R$_2$ is selected from the group comprising

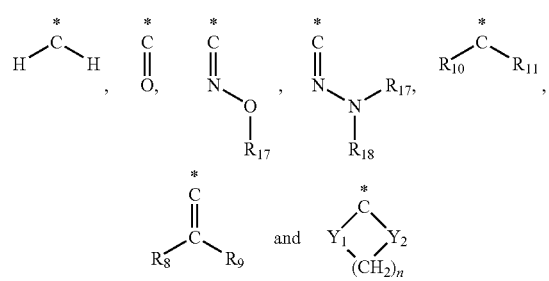

wherein:

Y$_1$ and Y$_2$ are independently selected from the group comprising O, S, NH, alkylamino, and CR$_{24}$R$_{25}$ or Y$_1$ is O, S or NH, alkylamino and Y$_2$ is CR$_{24}$R$_{25}$, with the proviso that Y$_1$ and Y$_2$ cannot both be O, S, NH or alkylamino if n is 0 or 1; R$_8$ and R$_9$ are independently selected from the group comprising hydrogen, halogen and alkyl; or R$_8$ and R$_9$ may be linked together to form a substituted or unsubstituted C$_{3-6}$ cycloalkyl; R$_{10}$ and R$_{11}$ are independently selected from the group comprising hydrogen, halogen and alkyl; * represents the point of attachment of the R$_2$ to the molecule of formula A R$_3$ substituents are independently selected from the group comprising alkyl, alkyloxy, and halogen;

R$_4$ is selected from the group comprising alkyl, aryl, heteroaryl, and adamantyl; R$_5$ is selected from the group comprising alkyl, alkyloxy, alkylthio, aryl, and heteroaryl; or R$_4$ and R$_5$ may be linked together to form a substituted or unsubstituted 5- or 6-membered cycloalkyl or cycloalkenyl ring, where said substituents are selected from the group comprising —OH, =O, halogen, alkyl, and where 1 or 2 of the carbon atoms on said 5- or 6-membered cycloalkyl or cycloalkenyl ring may be optionally replaced by W where W is selected from the group comprising O, S N, NH, alkylamino, and arylamino;

m and n are independently 0, 1, 2 or 3, and pharmaceutically acceptable salts of the thereof.

The non-limiting examples shown in schemes 1-4, illustrate some methods for carrying out the preparative process of the invention. LG represents a leaving group as defined herein.

Scheme 1

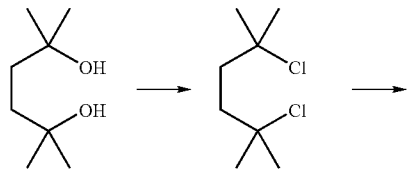

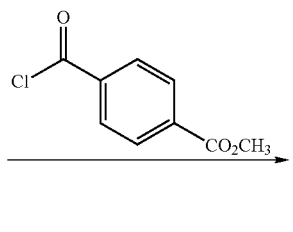

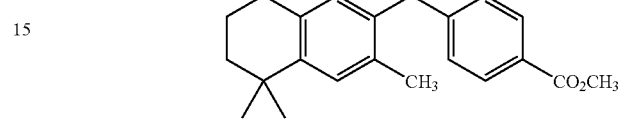

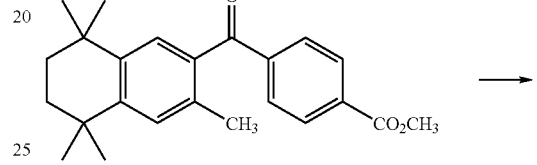

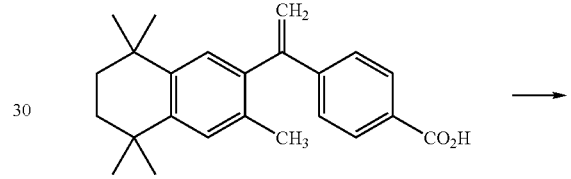

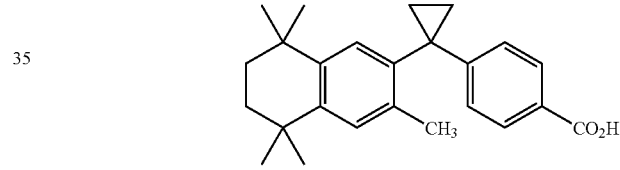

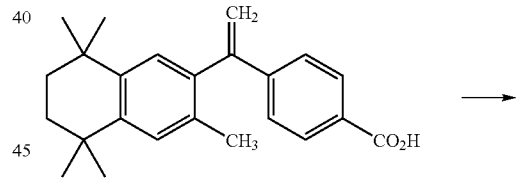

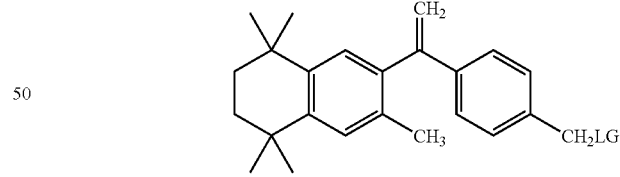

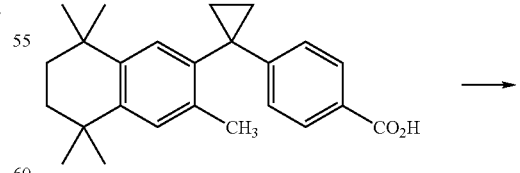

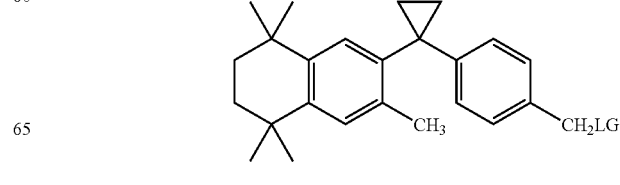

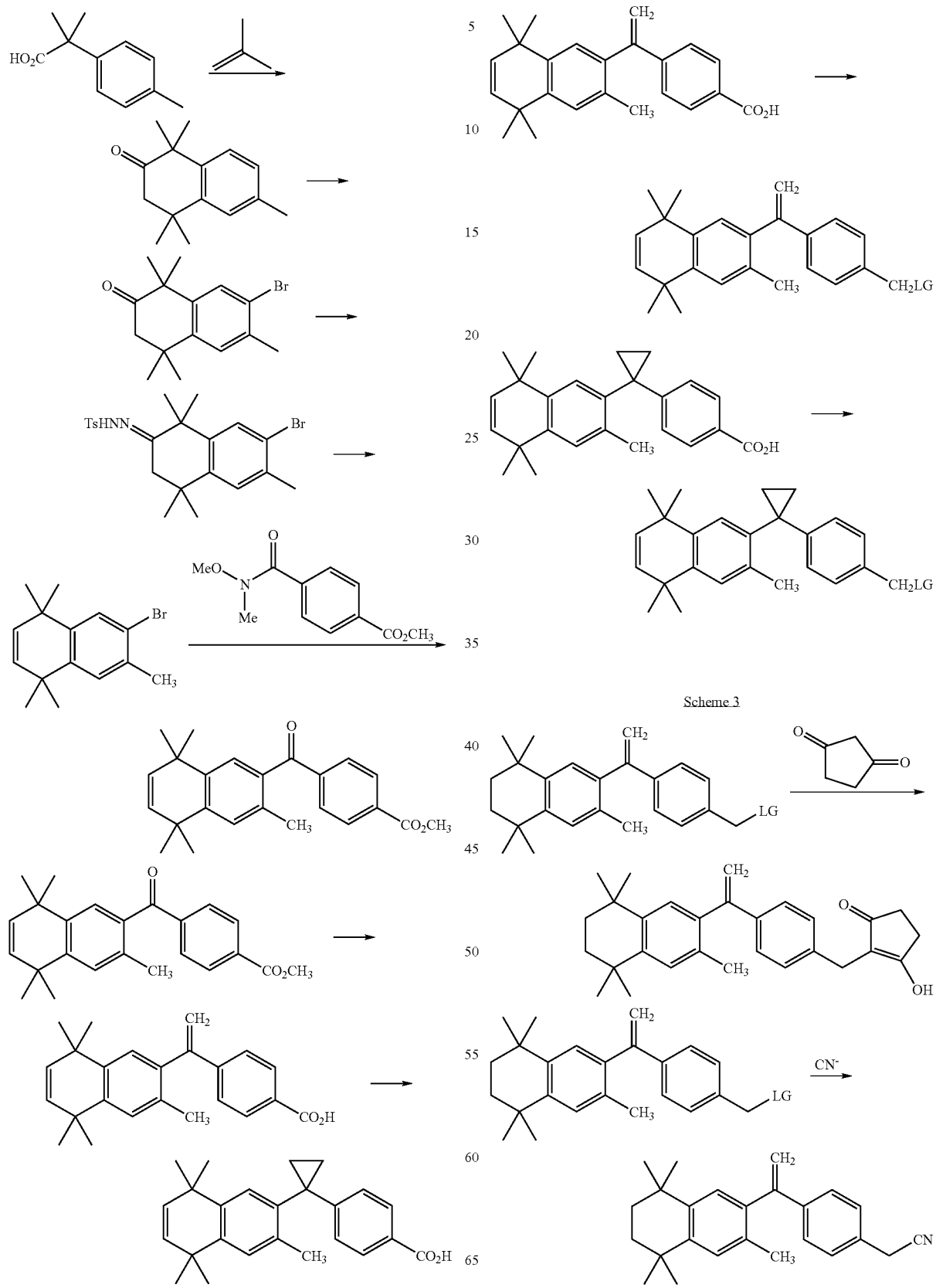

-continued

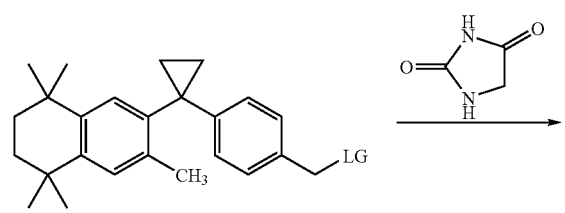

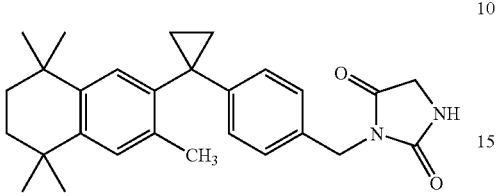

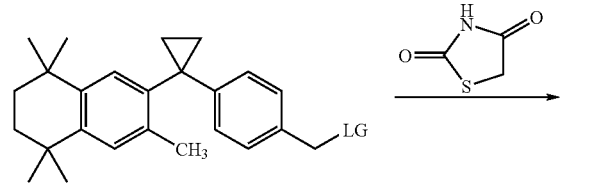

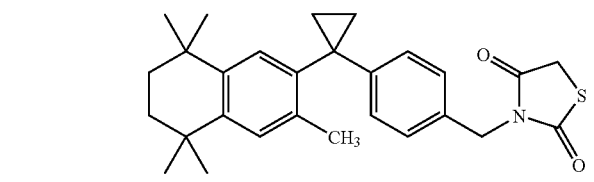

Scheme 4

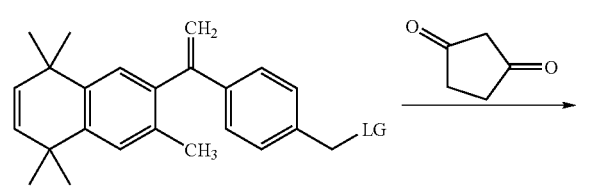

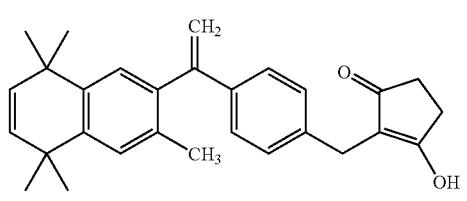

-continued

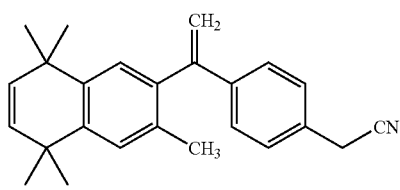

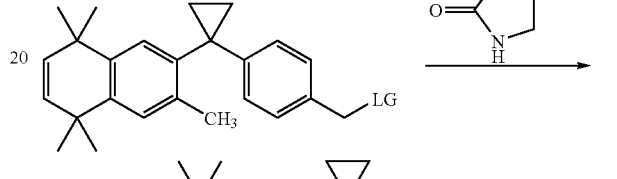

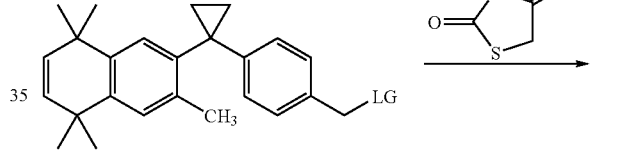

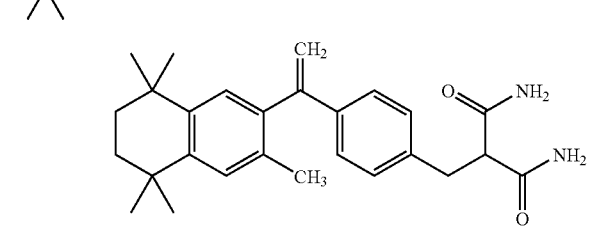
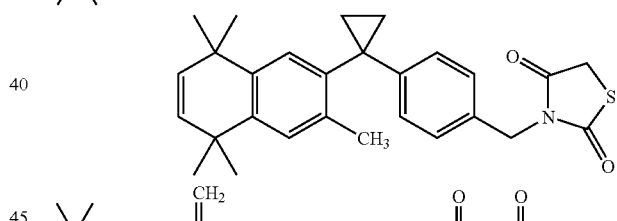

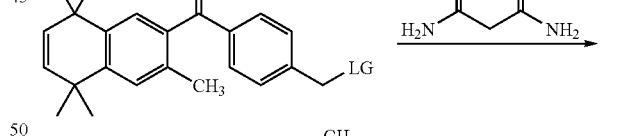

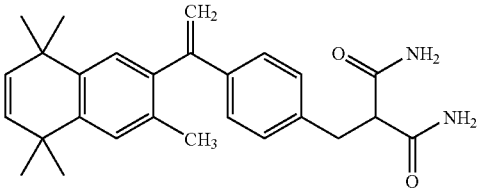

In another aspect, the invention relates to pharmaceutical compositions containing the novel compounds of the invention and to methods of using these compounds for modulating and controlling cell cycle, cell differentiation and apoptosis processes regulated by certain hormones, such as for example the thyroid hormone and the like, and/or certain vitamins, such as for example vitamin D and the like, and/or certain retinoids, such as for example 9-cis-retinoic acid and the like.

In another aspect, the invention relates to pharmaceutical compositions containing the novel compounds of the invention and to methods of using these compounds for modulating and controlling cell cycle, cell differentiation and apoptosis processes regulated by certain genes, such as for example the Fibroblast Growth Fact Binding Protein mRNA, and the like, and/or certain Signal Transducers and Activators of Transcription, such as for example STAT3, and the like, and/or certain proteins, such as for example Cyclin Dependent Kinase (CDK), Transforming Growth Factor alpha (TGF-α), and the like, and/or certain receptors, such as for example Transforming Growth Factor Receptor (TGFR), Endothelial Growth Factor Receptor (EGFR), Retinoid X Receptor (RXR) and the like.

In another aspect, the invention relates to pharmaceutical compositions containing the novel compounds of the invention and to methods of using these compounds to modulate selective gene expression by one or more cellular receptors.

In another aspect, the invention relates to pharmaceutical compositions containing the novel compounds of the invention and to methods of treating diseases and/or conditions using the same. Examples of such disorders include proliferative disorders, differentiation disorders, cancer, inflammatory diseases, cardiovascular diseases, plasma HDL levels, apolipoprotein A1 metabolism, hyperlipidemia, lipid metabolism, lipid homeostasis, hyperlipidemia, skin-related processes, autoimmune diseases, fatty acid metabolism, malignant cell development, premalignant lesions, programmed cell death, endocrinological processes, AP-1 metabolism and the like.

In another aspect, the invention relates to pharmaceutical compositions containing the novel compounds of the invention and to methods of treating diseases and/or conditions using the same. Example of diseases and/or conditions include cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like.

In yet another aspect, the invention relates to pharmaceutical compositions containing the novel compounds of the invention in combination with other therapeutic agents and to methods of treating diseases and/or conditions using the same. Example of diseases and/or conditions include cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia and the like. Examples of other therapeutic agents include Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Toremifene, Arzoxifene, Raloxifene, Tamoxifen, and the like.

The invention further provides pharmaceutical compositions containing one or more of the novel compounds as well as pharmaceutically acceptable pro-drugs and salts of such compounds.

Additional aspects of the invention are set forth in part in the detailed description which follows, and in part will become apparent to those skilled in the art upon examination of the following, or may be learned by practice of the invention.

DETAILED DESCRIPTION OF THE INVENTION

In one embodiment of the invention, there are provided compounds comprising the structural formula A:

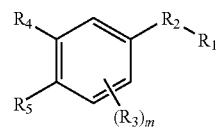

wherein:
a. $R_1$ is

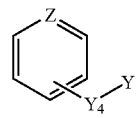

b. Z is selected from the group comprising CH, and nitrogen
c. $Y_4$ is selected from the group comprising substituted or unsubstituted $C_{1-6}$ alkyl, $C_{1-6}$ alkyl, $C_{0-5}$ alkyloxy-$C_{0-5}$ alkyl, $C_{0-5}$ alkylthio-$C_{0-5}$ alkyl, and $C_{0-5}$ alkylamino-$C_{0-5}$ alkyl
d. Y can be attached to any position on $Y_4$ and Y is selected from the group comprising cyano, —COOR$_{21}$, —CONR$_{22}$R$_{23}$, —CONR$_{21}$NR$_{22}$R$_{23}$, heteroaryl, formulae $A_1, A_2, A_3, A_4, A_5$,

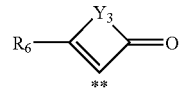

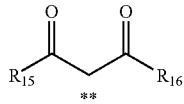

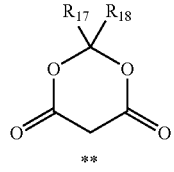

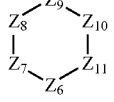

wherein:
i) $Y_3$ is selected from the group comprising $C_{2-8}$ alkyl, and $C_{2-8}$ substituted alkyl,
ii) $Z_2$, $Z_5$, $Z_7$ and $Z_{11}$ are independently selected from the group comprising C=O, C=S, C=NR$_{17}$, C=NNR$_{22}$R$_{23}$, C=NOR$_{17}$, and CR$_{24}$R$_{25}$
iii) $Z_1$, $Z_3$, $Z_4$, $Z_6$, $Z_8$, $Z_9$ and $Z_{10}$ are independently selected from the group comprising O, S N, —NH, alkylamino, arylamino, and CR$_{24}$R$_{25}$, but cannot be O or S if $Z_1$, $Z_3$, $Z_4$, $Z_6$, $Z_8$, $Z_9$ or $Z_{10}$ is the point of attachment to $Y_4$, and $Z_3$ and $Z_4$ cannot both be O at the same time, and $Z_8$ and $Z_9$ cannot both be O at the same time, and $Z_9$ and $Z_{10}$ cannot both be O at the same time, and $Z_3$, $Z_4$, $Z_8$, $Z_9$ or $Z_{10}$ can form double bonds to each other provided that none are O or S.
iv) $R_6$ is selected from the group comprising —OH, alkyloxy, aryloxy, alkylcarboxy, arylcarboxy, —SH, alkylthio, arylthio, —NH$_2$, alkylamino, arylamino, N-aryl-N-alkylamino, —NHNH$_2$, alkylhydrazino, arylhydrazino, N-aryl-N-alkylhydrazino, —NHOR$_{17}$, —O(P=O)(OR$_{17}$)(OR$_{18}$), —OCH$_2$O(P=O)(OR$_{17}$)(OR$_{18}$), and —OSO$_3$R$_{17}$,
v) $R_{15}$ and $R_{16}$ are independently selected from the group comprising —OH, alkyloxy, aryloxy, —NH$_2$, alkylamino, arylamino, N-aryl-N-alkylamino, —NHNH$_2$, alkylhydrazino, arylhydrazino, N-aryl-N-alkylhydrazino, —NHOR$_{17}$, alkyl, and aryl,
vi) $R_{17}$ and $R_{18}$ are independently selected from the group comprising hydrogen, alkyl, and aryl,
vii) $R_{21}$, $R_{22}$ and $R_{23}$ are independently selected from hydrogen, alkyl, aryl, or $R_{22}$ and $R_{23}$ are taken together with the nitrogen to which they are attached forming a saturated cyclic or unsaturated cyclic system containing 3 to 8 carbon atoms with at least one substituent as defined herein.
viii) $R_{24}$ and $R_{25}$ are independently selected from the group comprising hydrogen, halogen, alkyl, and aryl,
ix) ** represents the point of attachment of Y to $Y_4$
e. $R_2$ is selected from the group comprising

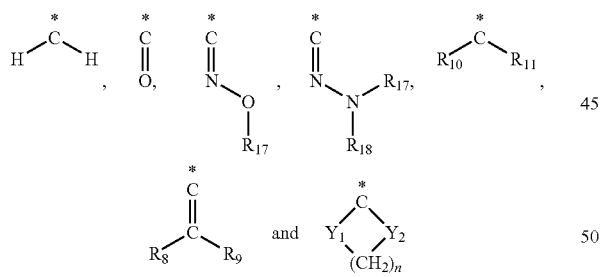

wherein:
i) $Y_1$ and $Y_2$ are independently selected from the group comprising O, S NH, alkylamino, and CR$_{24}$R$_{25}$ or $Y_1$ is O, S or NH, alkylamino and $Y_2$ is CR$_{24}$R$_{25}$, with the proviso that $Y_1$ and $Y_2$ cannot both be O, S, NH or alkylamino if n is 0 or 1, and
ii) $R_8$ and $R_9$ are independently selected from the group comprising hydrogen, halogen and alkyl; or $R_8$ and $R_9$ may be linked together to form a substituted or unsubstituted $C_{3-6}$cycloalkyl;
iii) $R_{10}$ and $R_{11}$ are independently selected from the group comprising hydrogen, halogen and alkyl;
iv) * represents the point of attachment of the $R_2$ to the molecule of formula A f. $R_3$ substituents are independently selected from the group comprising alkyl, alkyloxy, and halogen,
g. $R_4$ is selected from the group comprising alkyl, aryl, heteroaryl, and adamantyl; $R_5$ is selected from the group comprising alkyl, alkyloxy, alkylthio, aryl, and heteroaryl; or $R_4$ and $R_5$ may be linked together to form a substituted or unsubstituted 5- or 6-membered cycloalkyl or cycloalkenyl ring, where said substituents are selected from the group comprising —OH, =O, halogen, alkyl, and where 1 or 2 of the carbon atoms on said 5- or 6-membered cycloalkyl or cycloalkenyl ring may be optionally replaced by W where W is selected from the group comprising O, S N, NH, alkylamino, and arylamino;
h. m and n are independently 0, 1, 2 or 3,
and pharmaceutically acceptable salts of the thereof.

In another embodiment of the invention, there are provided compounds having the structure, selected from the group comprising formulae $B_1$, $B_2$, $B_3$, $B_4$, $B_5$, $B_6$, $B_7$, $B_8$, $B_9$, $B_{10}$, $B_{11}$, and $B_{12}$

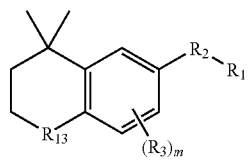

$B_1$

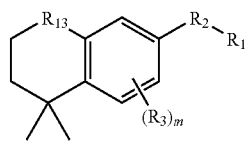

$B_2$

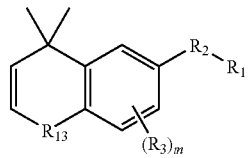

$B_3$

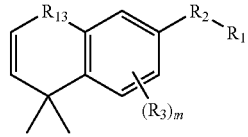

$B_4$

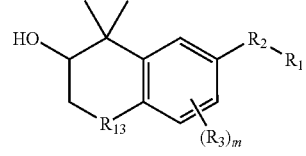

$B_5$

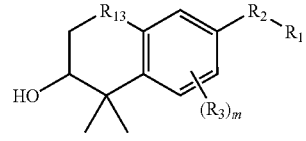

$B_6$

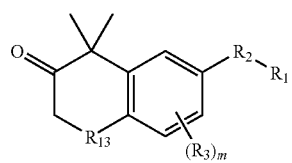
B7

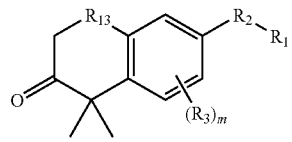
B8

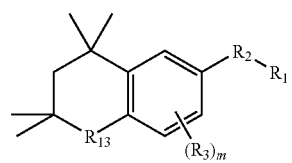
B9

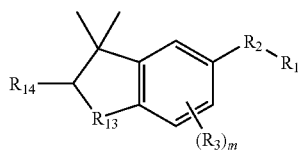
B10

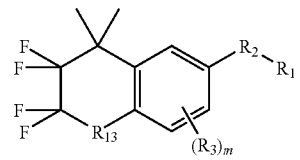
B11

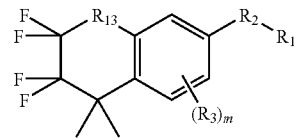
B12 wherein $R_1$, $R_2$ and $R_3$ are as described above and $R_{13}$ is selected from the group comprising O, S $(CH_3)_2C$ and $CH_2$, and $R_{14}$ is hydrogen or methyl.

The compounds according to this invention may contain one or more asymmetric carbon atoms and can thus occur as racemates and racemic mixtures, single enantiomers, diastereomeric mixtures or individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All such isomeric forms of these compounds are expressly included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers.

The terms "optically pure compound" or "optically pure isomer" refers to a single stereoisomer of a chiral compound regardless of the configuration of the said compound.

For purpose of this application, all sugars are referenced using conventional three-letter nomenclature. All sugars are assumed to be in the D-form unless otherwise noted, except for fucose, which is in the L-form. Further, all sugars are in the pyranose form.

The compounds according to this invention may occur as a mixture of tautomers. The term "tautomer" or "tautomerism" refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention. The following example of tautomerism is provided for reference:

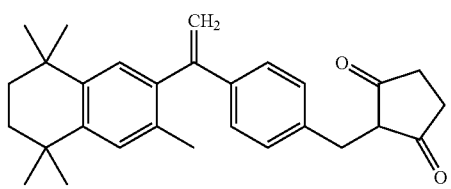
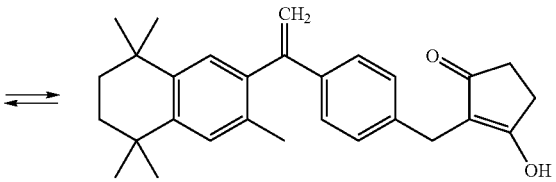

The following example of nomenclature and numbering system is provided for reference.

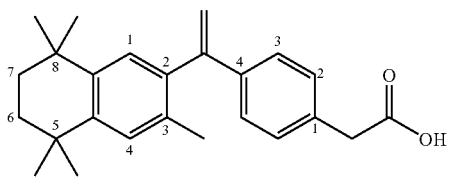

4-[1-(3,5,5,8,8-Pentamethyl-5,6,7,8-tetrahydro-naphthalen-2-yl)-vinyl]-phenyl acetic acid The term "substantially homogeneous" refers to collections of molecules wherein at least 80%, preferably at least about 90% and more preferably at least about 95% of the molecules are a single compound or a single stereoisomer thereof.

As used herein, the term "attached" signifies a stable covalent bond, certain preferred points of attachment being apparent to those skilled in the art.

The terms "optional" or "optionally" refer to occurrence or non-occurrence of the subsequently described event or circumstance, and that the description includes instances where said event or circumstance occurs and instances where it does not. In such context, the sentence "optionally substituted alkyl group" means that the alkyl group may or may not be substituted and the description includes both a substituted and an unsubstituted alkyl group.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount", yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

When used in conjunction with a compound of this invention, the terms "elicite", "eliciting, "modulator", "modulate", "modulating", "regulator", "regulate" or "regulating" selective gene expression refer to a compound that can act as an activator, an agonist, a pan-agonist or an antagonist of gene expression by a particular receptor, such as for example a Retinoid X Receptor and the like.

The terms "therapeutic agent" and "chemotherapeutic agent", refer to a compound or compounds and pharmaceutically acceptable compositions thereof that are administered to mammalian subjects as prophylactic or remedy in the treatment of a disease or medical condition. Such compounds may be administered to the subject via oral formulation, transdermal formulation or by injection.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dehydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like. Certain Lewis acids may have optically pure ligands attached to the electron acceptor atom, as set forth in Corey, E. J. Angewandte Chemie, International Edition (2002), 41(10), 1650-1667; Aspinall, H. C. Chemical Reviews (Washington, DC, United States) (2002), 102(6), 1807-1850; Groger, H. Chemistry—A European Journal (2001), 7(24), 5246-5251; Davies, H. M. L. Chemtracts (2001), 14(11), 642-645; Wan, Y. Chemtracts (2001), 14(11), 610-615; Kim, Y. H. Accounts of Chemical Research (2001), 34(12), 955-962; Seebach, D. Angewandte Chemie, International Edition (2001), 40(1), 92-138; Blaser, H. U. Applied Catalysis, A: General (2001), 221(1-2), 119-143; Yet, L. Angewandte Chemie, International Edition (2001), 40(5), 875-877; Jorgensen, K. A. Angewandte Chemie, International Edition (2000), 39(20), 3558-3588; Dias, L. C. Current Organic Chemistry (2000), 4(3), 305-342; Spindler, F. Enantiomer (1999), 4(6), 557-568; Fodor, K. Enantiomer (1999), 4(6), 497-511; Shimizu, K. D.; Comprehensive Asymmetric Catalysis I-III (1999), 3, 1389-1399; Kagan, H. B. Comprehensive Asymmetric Catalysis I-III (1999),1, 9-30; Mikami, K. Lewis Acid Reagents (1999), 93-136 and all references cited therein. Such Lewis acids maybe used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, acetyl chloride, succinic anhydride, diketene, diallyl carbonate, carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell and as such would be obvious to one of ordinary skill and knowledge in the art. The definition of "electrophile" includes but is not limited to: hydronium, acylium, lewis acids, such as for example, boron trifluoride and the like, halogens, such as for example $Br_2$ and the like, carbocations, such as for example tert-butyl cation and the like, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyldimethyl silyll chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "leaving group" refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, methanesulfonate, tolylsulfonate, trifluoromethanesulfonate, acetate, trichloroacetate, benzoate and the like.

The term "oxidant" refers to any reagent that will increase the oxidation state of a carbon atom in the starting material by either adding an oxygen atom to this carbon or removing an electron from this carbon and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "reducing reagent" refers to any reagent that will decrease the oxidation state of a carbon atom in the starting material by either adding a hydrogen atom to this carbon or adding an electron to this carbon and as such would be obvious to one of ordinary skill and knowledge in the art. The definition of "reducing reagent" includes but is not limited to: borane-dimethyl sulfide complex, 9-borabicyclo[3.3.1.]nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl) carbodiimide (EDCl), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, brom-trispyrrolidino-phosphonium hexafluorophosphate, 2-(5-norbornene-2,3-dicarboximido)-1,3,3-tetramethyluronium tetrafluoroborate (TNTU), O-(N-succinimidyl)-1,1,3,3-tetramethyluronium tetrafluoroborate (TSTU), tetramethylfluoroformamidinium hexafluorophosphate and the like.

The term "removable protecting group" or "protecting group" refers to any group which when bound to a functionality, such as the oxygen atom of a hydroxyl or carboxyl group or the nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:
a) Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiioxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl)ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like;
b) Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl (Trityl), α-naphthyldiphenylmethyl, (4-Methoxyphenyl)-diphenyl-methyl, di-(p-methoxyphenyl)-phenylmethyl, tri-(p-methoxyphenyl)methyl, 4(4'-bromophenacyloxy)-phenyldiphenylmethyl, 4,4',4''-tris(4,5-dichlorophthalimidophenyl)methyl, 4,4',4''-tris(levulinoyloxyphenyl)methyl, 4,4'-dimethoxy-3''-[N-(imidazolylmethyl)]trityl, 4,4'-dimethoxy-3''-[N-(imidazolylethyl)carbamoyl]trityl, 1,1-bis(4-methoxyphenyl)-1'-pyrenylmethyl, 4-(17-tetrabenzo[a,c,g,l]fluorenylmethyl)-4,4'-dimethoxytrityl, 9-anthryl, 9-(9-phenyl)xanthenyl, 9-(9-phenyl-10-oxo)anthryl and the like;

c) Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

d) —C(O)$R_{20}$, where $R_{20}$ is selected from alkyl, substituted alkyl, aryl and more specifically $R_{20}$=hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[bis(4-methoxyphenyl)hydroxymethylphenoxy]-4-oxopentyl, phenyl, 4methylphenyl, 4-nitrophenyl, 4-fluorophenyl, 4-chlorophenyl, 4-methoxyphenyl, 4-phenylphenyl, 2,4.6-trimethylphenyl, α-naphthyl, benzoyl and the like;

e) —C(O)O$R_{20}$, where $R_{20}$ is selected from alkyl, substituted alkyl, aryl and more specifically $R_{20}$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-Butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

The definition of "amino protecting group" includes but is not limited to:

a) 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonytmethyl, m-nitrophenyl, 3.5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3nitro-2-pyridinesulfenyl, N-p-toluenesulfonyl, N-benzenesulfonyl, N-2,3,6-trimethyl4-methoxybenzenesulfonyl, N-2,4,6-trimethoxybenzene-sulfonyl, N-2,6-dimethyl-4-methoxybenzenesulfonyl, N-pentamethylbenzenesulfonyl, N-2,3,5.6-tetramethyl-4-methoxybenzenesulfonyl and the like;

b) —C(O)O$R_{20}$, where $R_{20}$ is selected from alkyl, substituted alkyl, aryl and more specifically $R_{20}$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10, 10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1.1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, Vinyl, allyl, 1-isopropylallyl, cinnamyl, 4-nitrocinnamyl, 3-(3'-pyridyl)prop-2-enyl, 8-quinolyl, N-Hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-tri-methylphenyl, 4-(trimethylammonium)benzyl, 2,4,6-trimethylbenzyl and the like.

The definition of "carboxyl protecting group" includes but is not limited to:

2-N-(morpholino)ethyl, choline, methyl, methoxyethyl, 9-Fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl. α-methylphenacyl, p-methoxyphenacyl, desyl, carboxamidomethyl, p-azobenzenecarboxamidomethyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butylmethoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2.6-dimethoxybenzyl, 4-(methylsulfinyl)benzyl, 4-Sulfobenzyl, 4-azidomethoxybenzyl, 4-(a/-[1-(4,4-dimethyl-2,6-dioxocyclohexylidene)-3-methylbutyl] aminobenzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like.

The term "Amino acid" refers to any of the naturally occurring amino acids, as well as synthetic analogs and derivatives thereof. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like. One of skill in the art will appreciate that the term "amino acid" can also include beta-, gamma-, delta-, omega-amino acids, and the like. Unnatural amino acids are also known in the art, as set forth in, Natchus, M. G. Organic Synthesis: Theory and Applications (2001), 5, 89-196; Ager, D. J. Current Opinion in Drug Discovery & Development (2001), 4(6), 800; Reginato, G. Recent Research Developments in Organic Chemistry (2000), 4(Pt. 1), 351-359; Dougherty, D. A. Current Opinion in Chemical Biology (2000), 4(6), 645-652; Lesley, S. A. Drugs and the Pharmaceutical Sciences (2000), 101(Peptide and Protein Drug Analysis), 191-205; Pojitkov, A. E. Journal of Molecular Catalysis B: Enzymatic (2000), 10(1-3), 47-55; Ager, D. J. Speciality Chemicals (1999), 19(1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components of compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group. The particular protecting group employed is not critical.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group.

The particular protecting group employed is not critical.

The term "Prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et a). (1998) "The Use of Esters as Prodrugs for Oral Delivery of .beta.-Lactam antibiotics," Pharm. Biotech. 11,:345365; Gaignault et al. (1996) "Designing Prodrugs and Bioprecursors I. Carrier Prodrugs," Pract. Med. Chem. 671-696; Asghamejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3): 183-209 (1999); Browne, "Fosphenytoin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8(1): 1-38 (1992); Fleisher et al. "Improved oral drug delivery: solubility limitations overcome by the use of prodrugs", Adv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989).

The terms "halogen", "halide" or "halo" include fluorine, chlorine, bromine, and iodine.

The terms "alkyl" and "substituted alkyl" are interchangeable and include substituted and unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group comprising halogen, —OH, —SH, —$NH_2$, —CN, —$NO_2$, =O, =$CH_2$, trihalomethyl, carbamoyl, aryl$C_{0-10}$alkyl, heteroaryl$C_{0-10}$alkyl, $C_{1-10}$alkyloxy, aryl$C_{0-10}$alkyloxy, $C_{1-10}$alkylthio, aryl$C_{0-10}$alkylthio, $C_{1-10}$alkylamino, aryl$C_{0-10}$ alkylamino, N-aryl-N-$C_{0-10}$alkylamino, $C_{1-10}$alkylcarbonyl, aryl$C_{0-10}$alkylcarbonyl, $C_{1-10}$alkylcarboxy, aryl$C_{0-10}$alkylcarboxy, $C_{1-10}$alkylcarbonylamino, aryl$C_{0-10}$alkylcarbonylamino, tetrahydrofuryl, morpholinyl, piperazinyl, hydroxypyronyl, —$C_{0-10}$alkylCOOR$_{21}$ and —$C_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined herein.

The term "alkyloxy" (e.g. methoxy, ethoxy, propyloxy, allyloxy, cyclohexyloxy) represents a substituted or unsubstituted alkyl group as defined above having the indicated number of carbon atoms attached through an oxygen bridge. The term "alkyloxyalkyl" represents an alkyloxy group attached through an alkyl or substituted alkyl group as defined above having the indicated number of carbon atoms.

The term "alkylthio" (e.g. methylthio, ethylthio, propylthio, cyclohexenylthio and the like) represents a substituted or unsubstituted alkyl group as defined above having the indicated number of carbon atoms attached through a sulfur bridge. The term "alkylthioalkyl" represents an alkylthio group attached through an alkyl or substituted alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, and the like) represents one or two substituted or unsubstituted alkyl groups as defined above having the indicated number of carbon atoms attached through an amine bridge. The substituted or unsubstituted alkyl groups maybe taken together with the nitrogen to which they are attached forming a saturated or unsaturated cyclic system containing 3 to 10 carbon atoms with at least one substituent as defined above. The term "alkylaminoalkyl" represents an alkylamino group attached through a substituted or unsubstituted alkyl group as defined above having the indicated number of carbon atoms.

The term "alkylhydrazino" (e.g. methylhydrazino, diethylhydrazino, butylhydrazino, (2-cyclopentyl)propylhydrazino, cyclohexanehydrazino, and the like) represents one or two substituted or unsubstituted alkyl groups as defined above having the indicated number of carbon atoms attached through a nitrogen atom of a hydrazine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylhydrazinoalkyl" represents an alkylhydrazino group attached through a substituted or unsubstituted alkyl group as defined above having the indicated number of carbon atoms.

The term "alkylcarbonyl" (e.g. cyclooctylcarbonyl, pentylcarbonyl, 3-hexenylcarbonyl and the like) represents a substituted or unsubstituted alkyl group as defined above having the indicated number of carbon atoms attached through a carbonyl group. The term "alkylcarbonylalkyl" represents an alkylcarbonyl group attached through a substituted or unsubstituted alkyl group as defined above having the indicated number of carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl and the like) represents an alkylcarbonyl group as defined above wherein the carbonyl is in turn attached through the nitrogen atom of an amino group. The nitrogen group may itself be substituted with a substituted or unsubstituted alkyl or aryl group. The term "alkylcarbonylaminoalkyl" represents an alkylcarbonylamino group attached through a substituted or unsubstituted alkyl group as defined above having the indicated number of carbon atoms.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group comprising halogen, —OH, —SH, —CN, —$NO_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, alkyl, aryl or R$_{22}$ and R$_{23}$ are taken together with the nitrogen to which they are attached forming a saturated cyclic or unsaturated cyclic system containing 3 to 8 carbon atoms with at least one substituent as defined above.

The definition of "aryl" includes but is not limited to phenyl, biphenyl, naphthyl, dihydronaphthyl, tetrahydronaphthyl, indenyl, indanyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through a substituted or unsubstituted alkyl group as defined above having the indicated number of carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl) propylcarbonyl, (2-chloronaphthyl)pentenyl-carbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of carbon atoms attached through an oxygen bridge. The term "aryloxyalkyl" represents an aryloxy group attached through a substituted or unsubstituted alkyl group as defined above having the indicated number of carbon atoms.

The term "arylthio" (e.g. phenylthio, naphthylthio, 3-bromophenylthio, and the like) represents an aryl or substituted aryl group as defined above having the indicated number of carbon atoms attached through a sulfur bridge. The term "arylthioalkyl" represents an arylthio group attached through a substituted or unsubstituted alkyl group as defined above having the indicated number of carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of carbon atoms attached through an amine bridge. The term "arylaminoalkyl" represents an arylamino group attached through a substituted or unsubstituted alkyl group as defined above having the indicated number of carbon atoms. The term "arylalkylamino" represents an aryl group attached through an alkylamino group as defined above having the indicated number of carbon atoms. The term "N-aryl-N-alkylamino" (e.g. N-phenyl-N-methylamino, N-naphthyl-N-butylamino, and the like) represents one aryl and one a substituted or unsubstituted alkyl group as defined above having the indicated number of carbon atoms independently attached through an amine bridge.

The term "arylhydrazino" (e.g. phenylhydrazino, naphthylhydrazino, 4-methoxyphenylhydrazino, and the like) represents one or two aryl groups as defined above having the indicated number of carbon atoms attached through a hydrazine bridge. The term "arylhydrazinoalkyl" represents an arylhydrazino group attached through a substituted or unsubstituted alkyl group as defined above having the indicated number of carbon atoms. The term "arylalkylhydrazino" represents an aryl group attached through an alkylhydrazino group as defined above having the indicated number of carbon atoms. The term "N-aryl-N-alkylhydrazino" (e.g. N-phenyl-N-methylhydrazino, N-naphthyl-N-butylhydrazino, and the like) represents one aryl and one a substituted or unsubstituted alkyl group as defined above having the indicated number of carbon atoms independently attached through an amine atom of a hydrazine bridge.

The term "arylcarboxy" (e.g. phenylcarboxy, naphthylcarboxy, 3-fluorophenylcarboxy and the like) represents an arylcarbonyl group as defined above wherein the carbonyl is in turn attached through an oxygen bridge. The term "arylcarboxyalkyl" represents an arylcarboxy group attached through a substituted or unsubstituted alkyl group as defined above having the indicated number of carbon atoms.

The term "arylcarbonylamino" (e.g. phenylcarbonylamino, naphthylcarbonylamino, 2-methylphenylcarbonylamino and the like) represents an arylcarbonyl group as defined above wherein the carbonyl is in turn attached through the nitrogen atom of an amino group. The nitrogen group may itself be substituted with an a substituted or unsubstituted alkyl or aryl group. The term "arylcarbonylaminoalkyl" represents an arylcarbonylamino group attached through a substituted or unsubstituted alkyl group as defined above having the indicated number of carbon atoms. The nitrogen group may itself be substituted with a substituted or unsubstituted alkyl or aryl group.

The term "arylcarbonylhydrazino" (e.g. phenylcarbonylhydrazino, naphthylcarbonylhydrazino, and the like) represents an arylcarbonyl group as defined above wherein the carbonyl is in turn attached through the nitrogen atom of a hydrazino group.

The terms "heteroaryl", "heterocycle" or "heterocyclic" refers to a monovalent unsaturated group having a single ring or multiple condensed rings, from 1 to 8 carbon atoms and from 1 to 4 hetero atoms selected from nitrogen, sulfur or oxygen within the ring. The heteroaryl groups in this invention can be optionally substituted with 1 to 3 substituents selected from the group comprising: halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N-$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{1-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5] tetrazinanyl-3,6-dione, dihydro-pyrimidinyl-2,4-dione, pyrimidinyl-2,4,6-trione and the like. For the purposes of this application, the terms "heteroaryl", "heterocycle" or "heterocyclic" do not include carbohydrate rings (i.e. mono- or oligosaccharides).

The term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

The saturated heterocyclic substituents are independently selected from the group comprising halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N-$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of saturated heterocyclic includes but is not limited to pyrrolidinyl, pyrazolidinyl, piperidinyl, 1,4-dioxanyl, morpholinyl, 1,4-dithienyl, thiomorpholinyl, piperazinyl, quinuclidinyl, and the like.

The term "alpha-beta-unsaturated carbonyl" refers to a molecule that has a carbonyl group directly attached to a double or triple bonded cabon and which would be obvious to one of ordinary skill and knowledge in the art. The definition of alpha-beta-unsaturated carbonyl includes but is not limited to acrolein, methyl vinyl ketone, and the like.

Invention compounds having structure A include

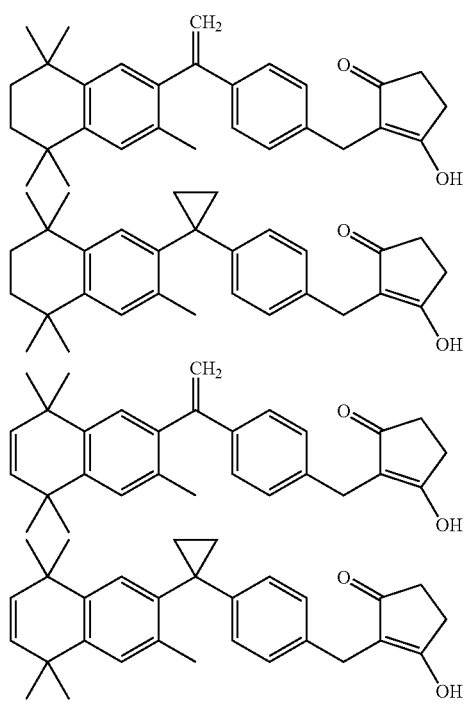

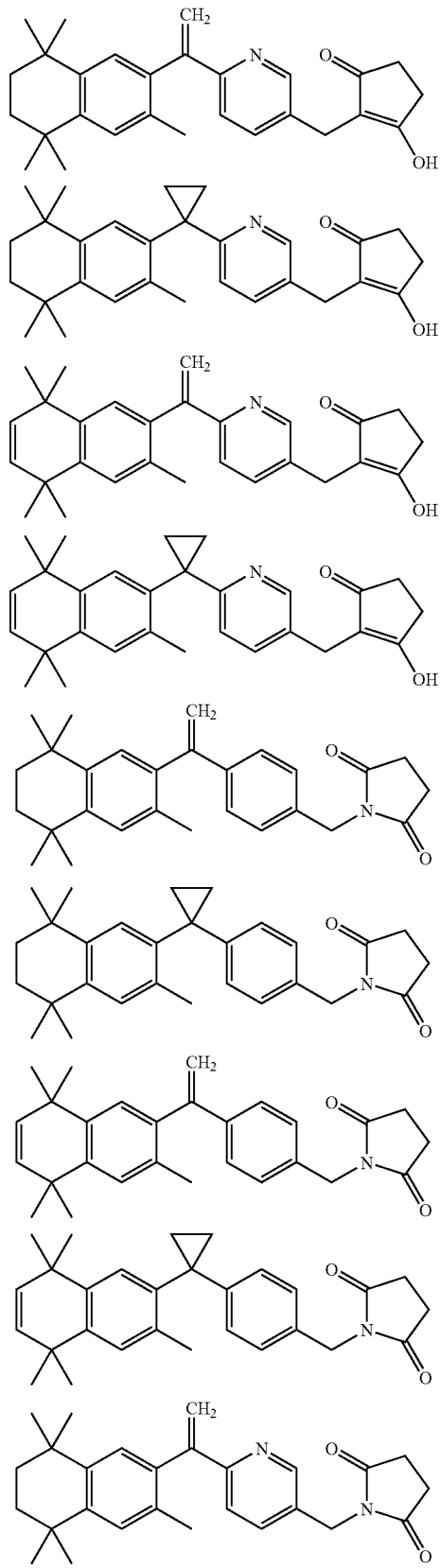

-continued
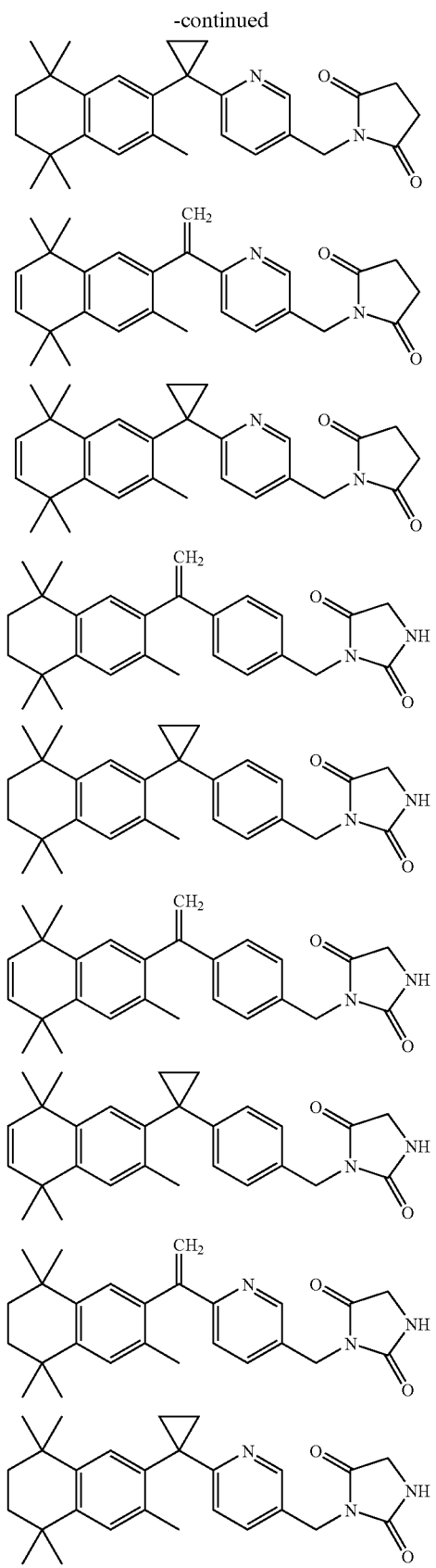
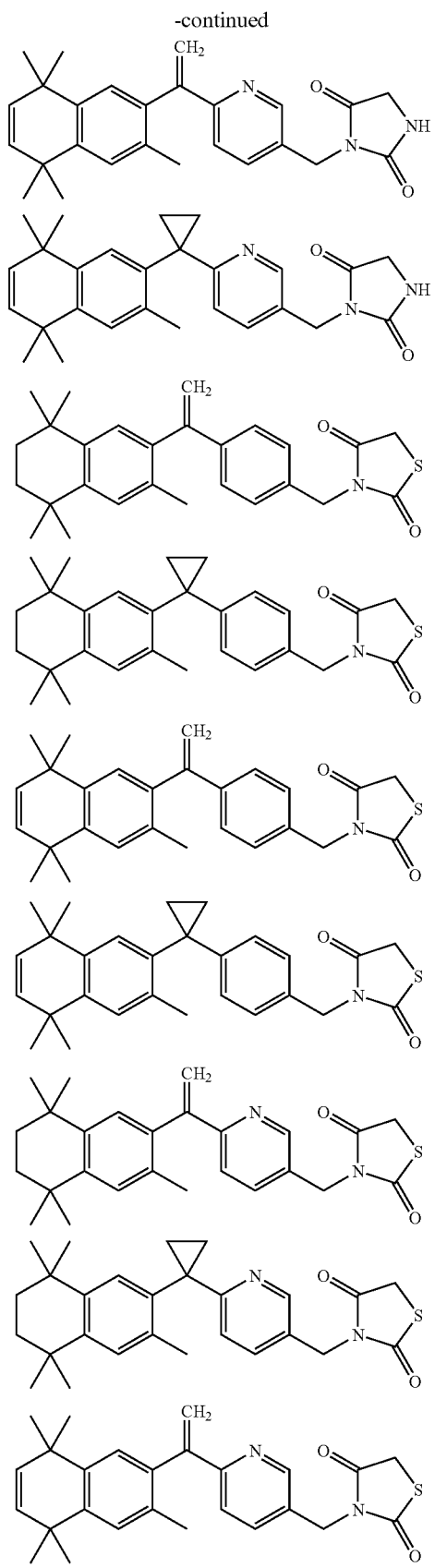

-continued
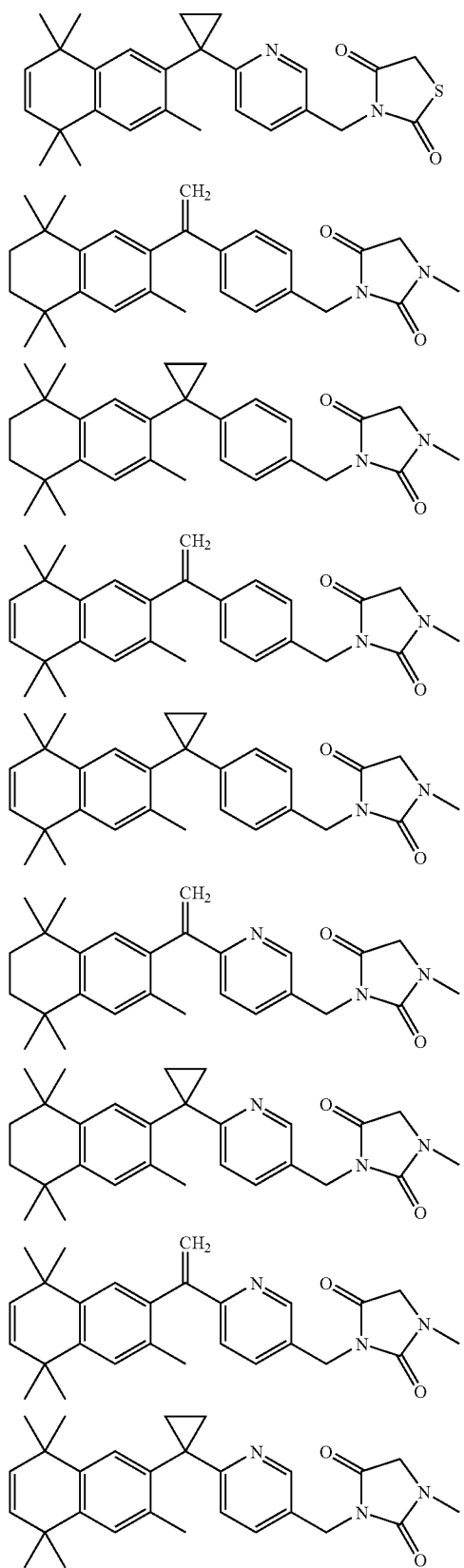
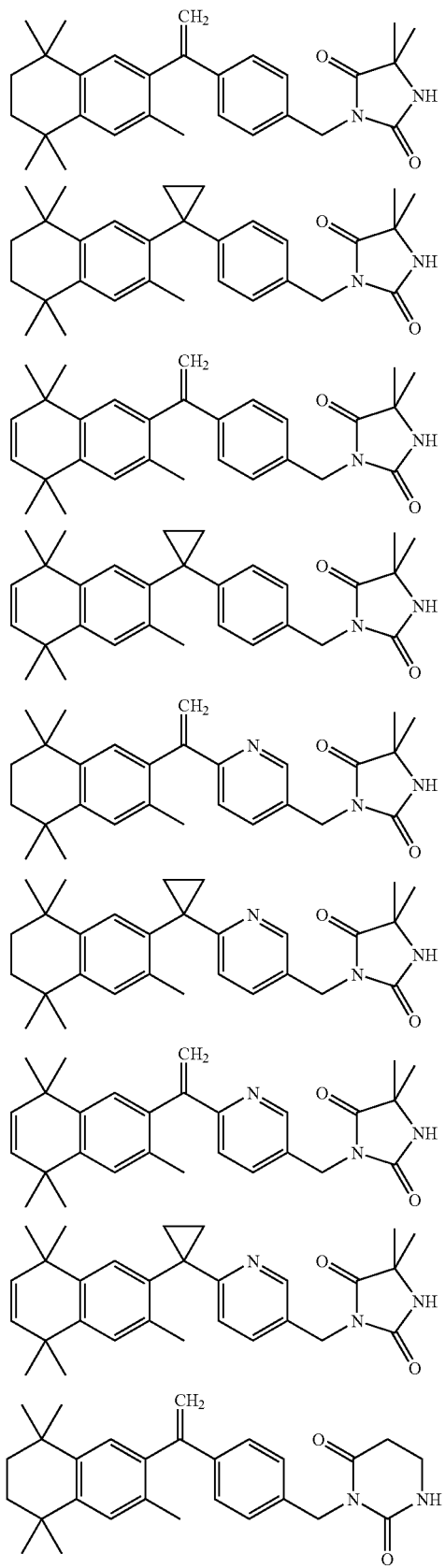

-continued
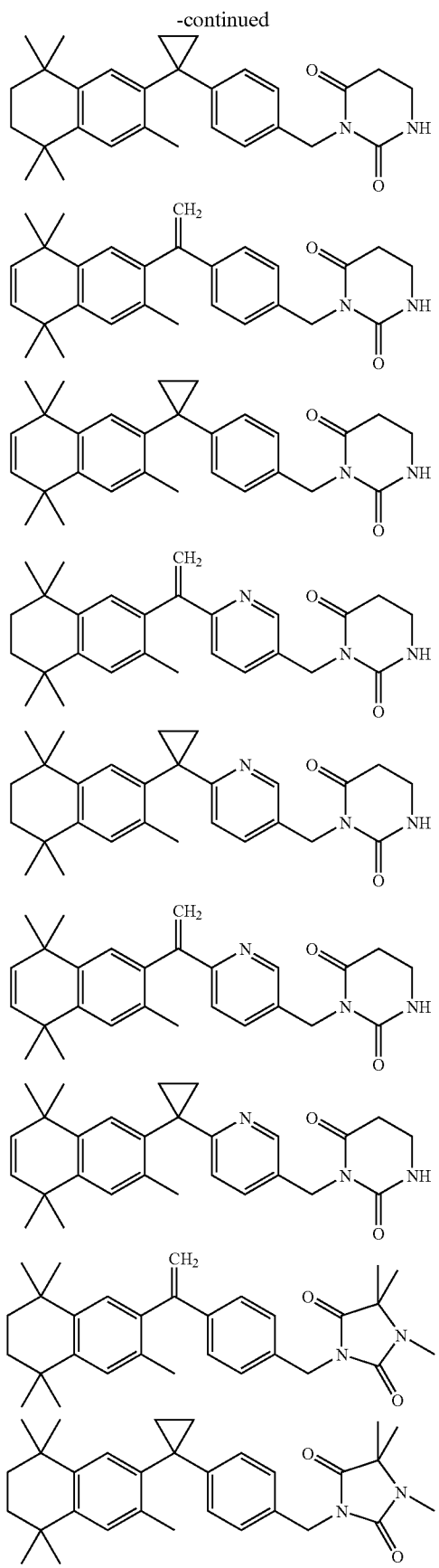
-continued
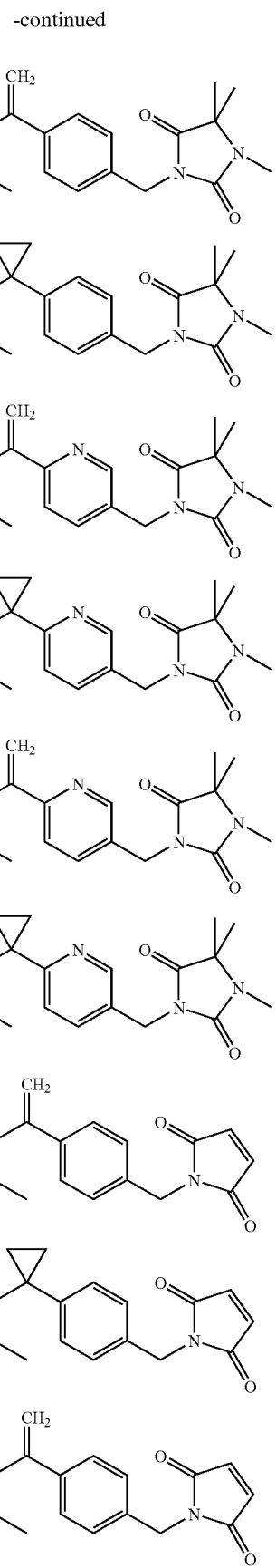

-continued
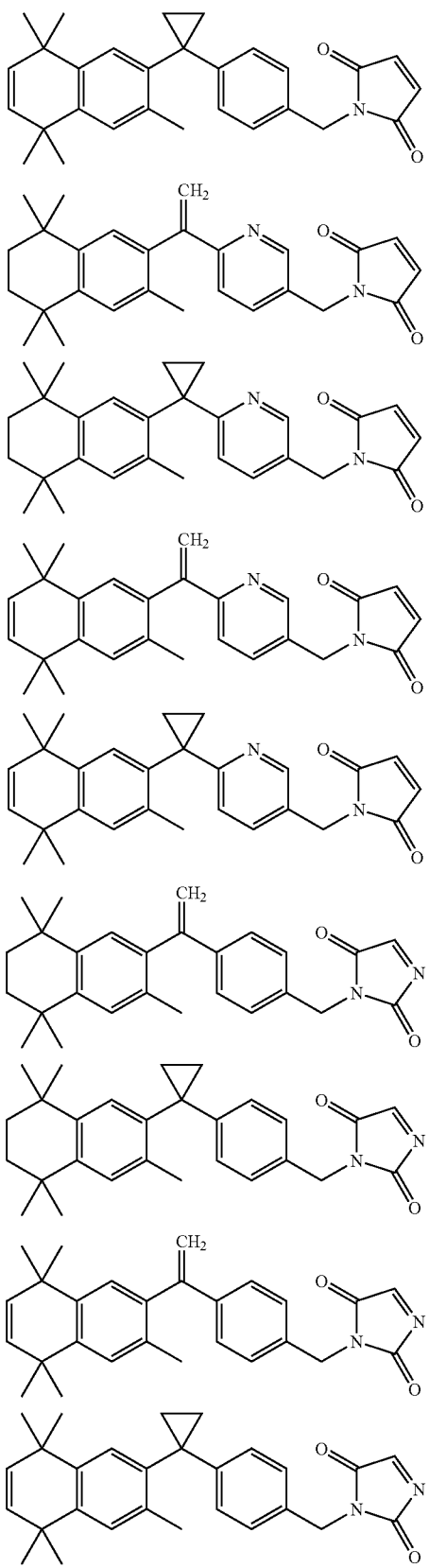
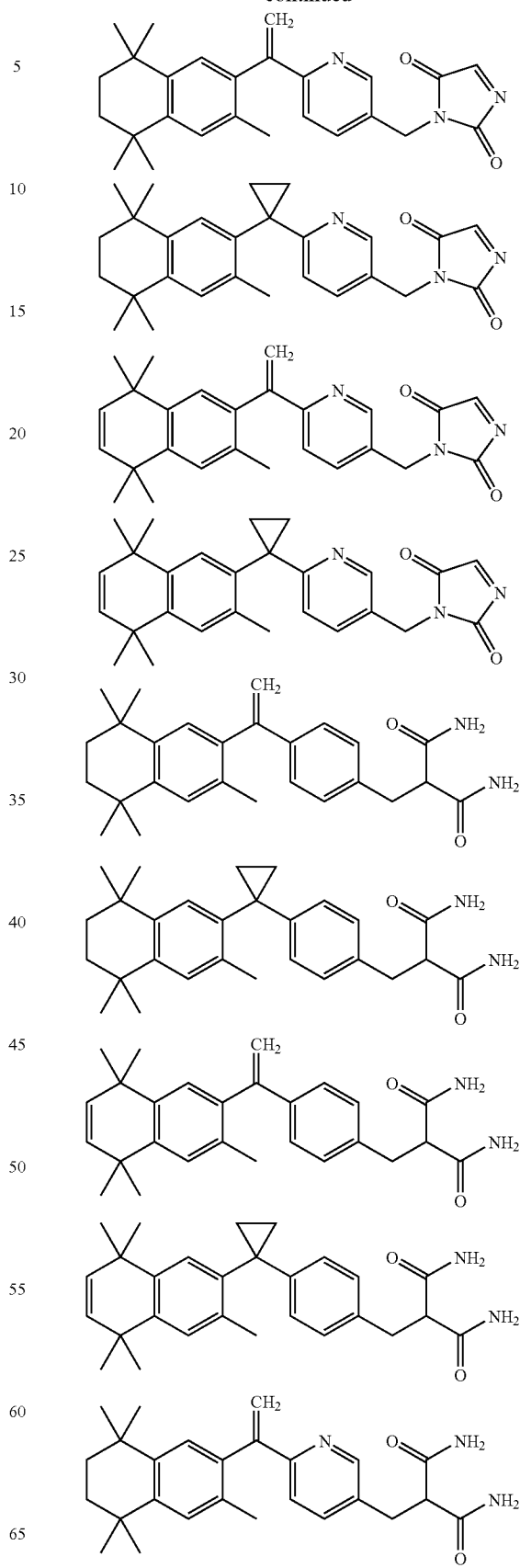

-continued
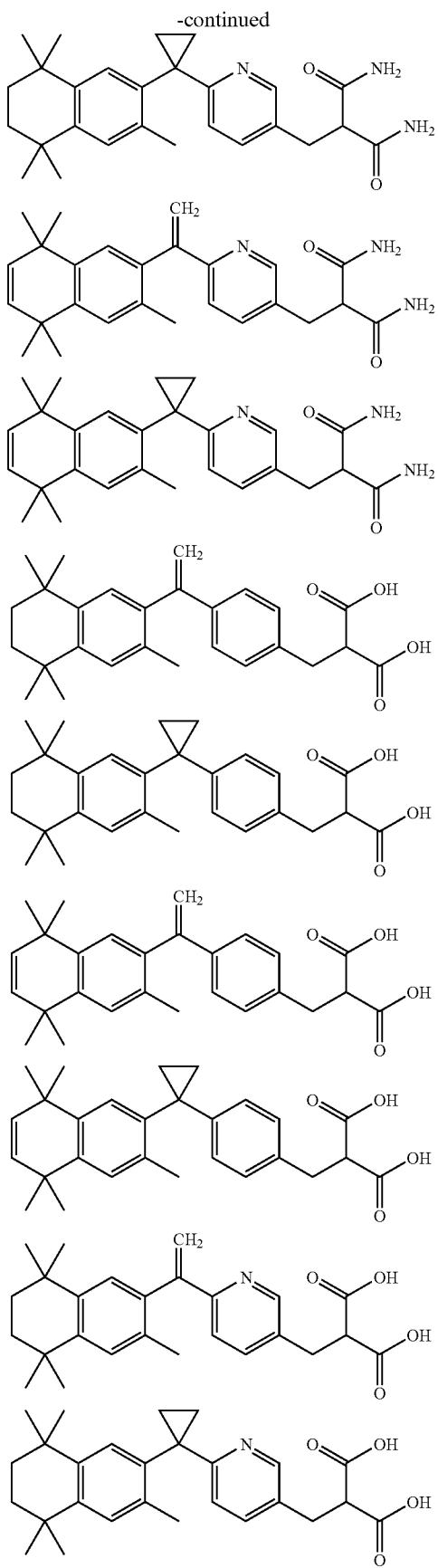
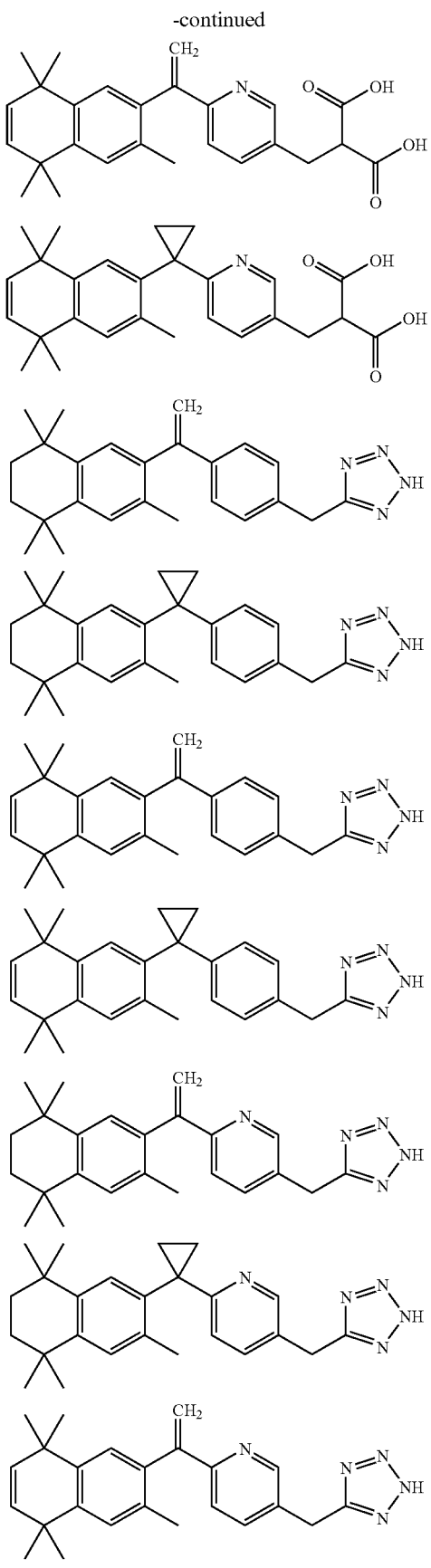

-continued
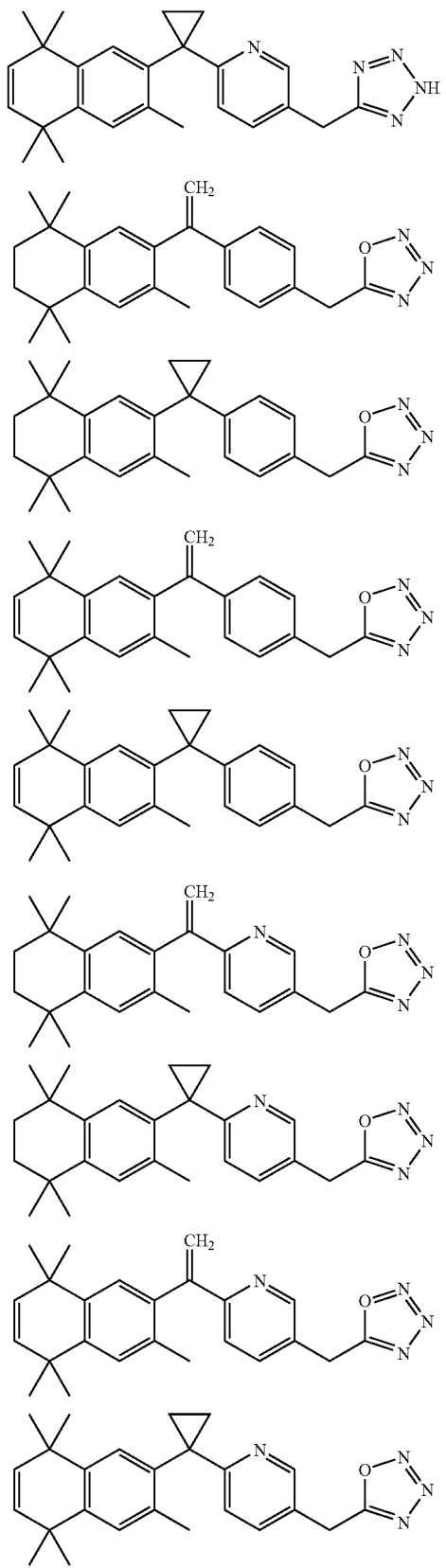
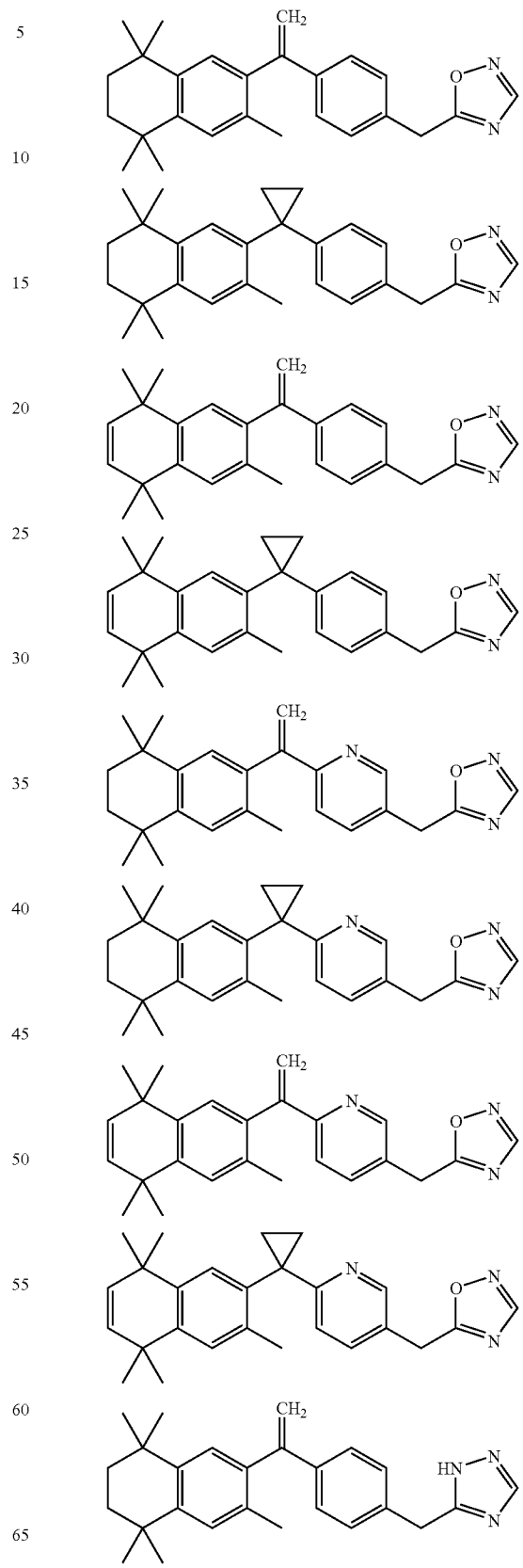

-continued
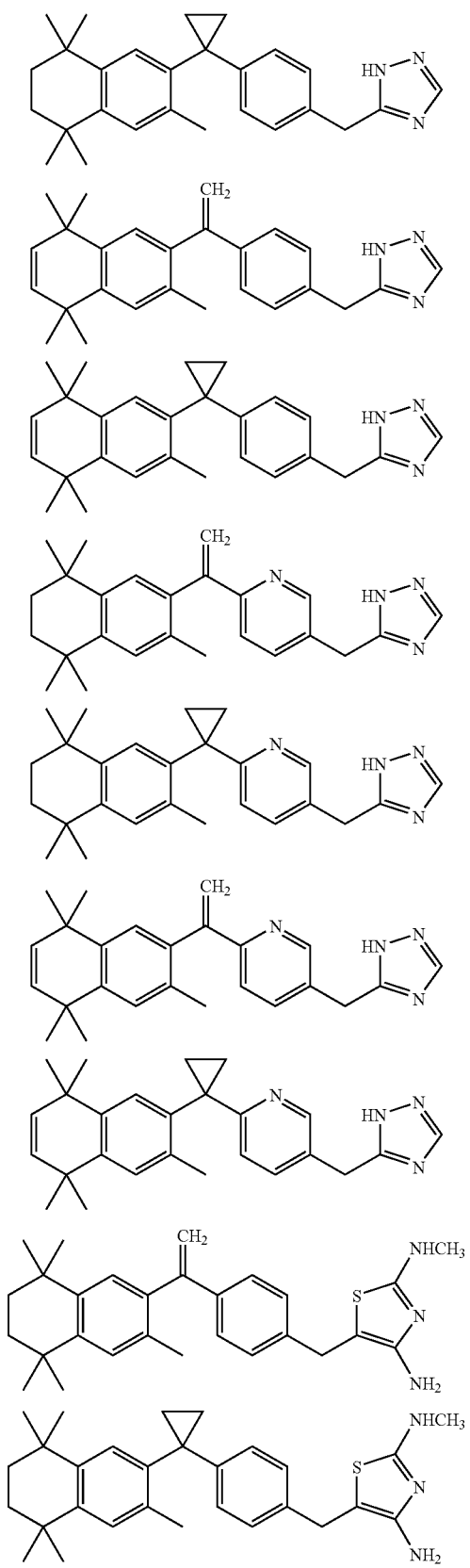
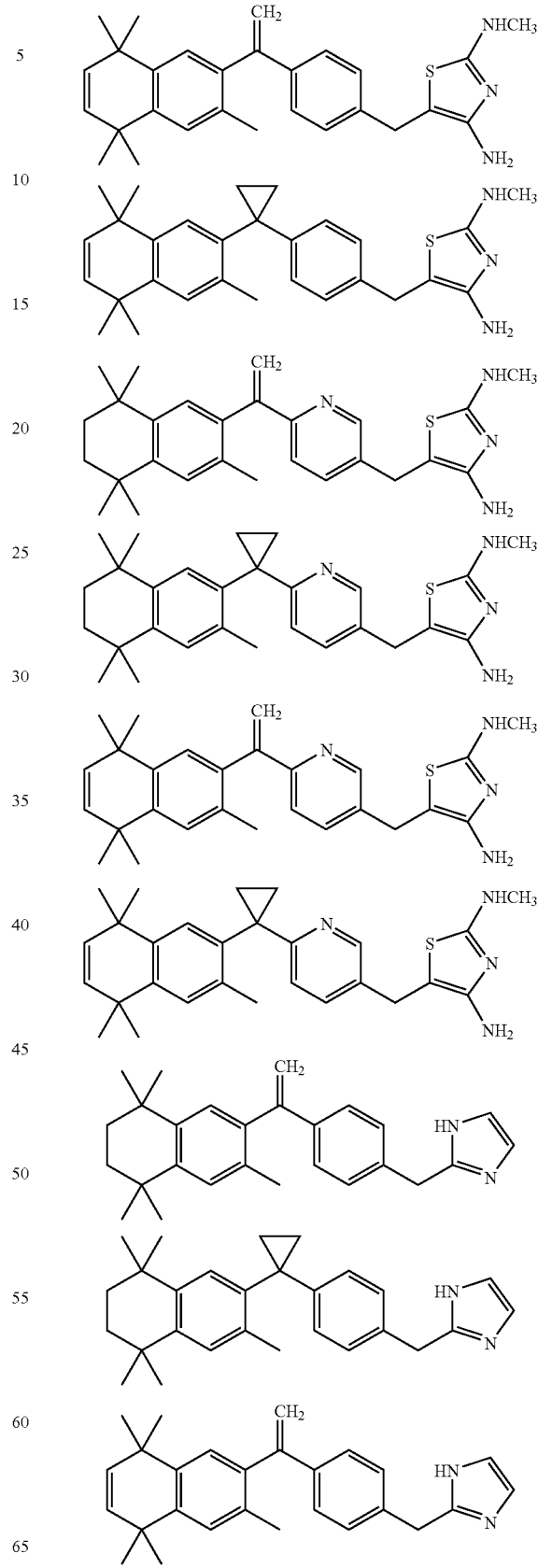

-continued
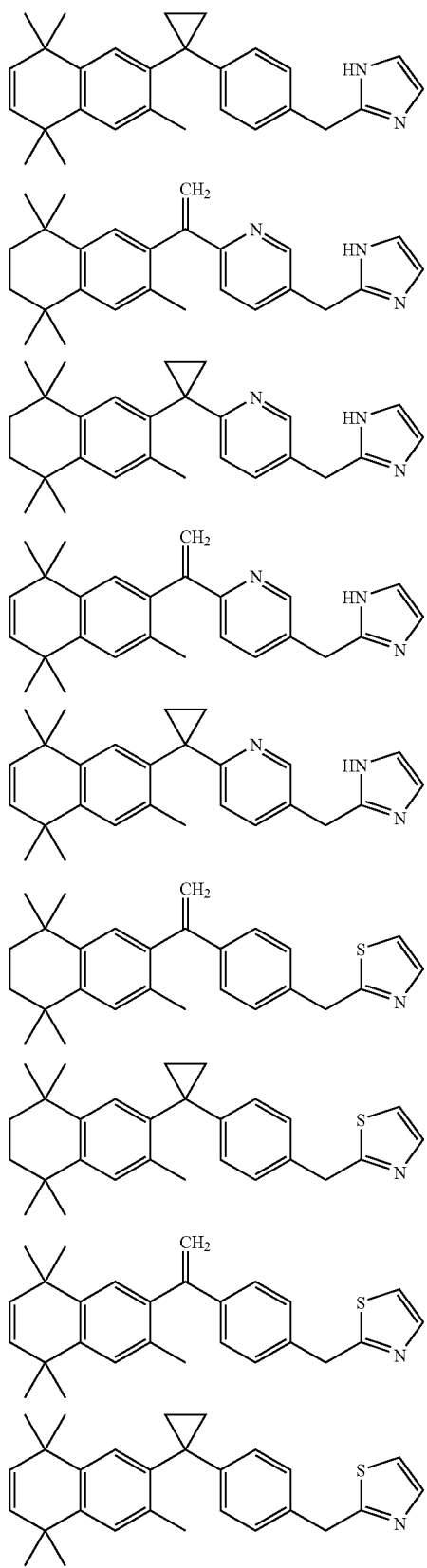
-continued
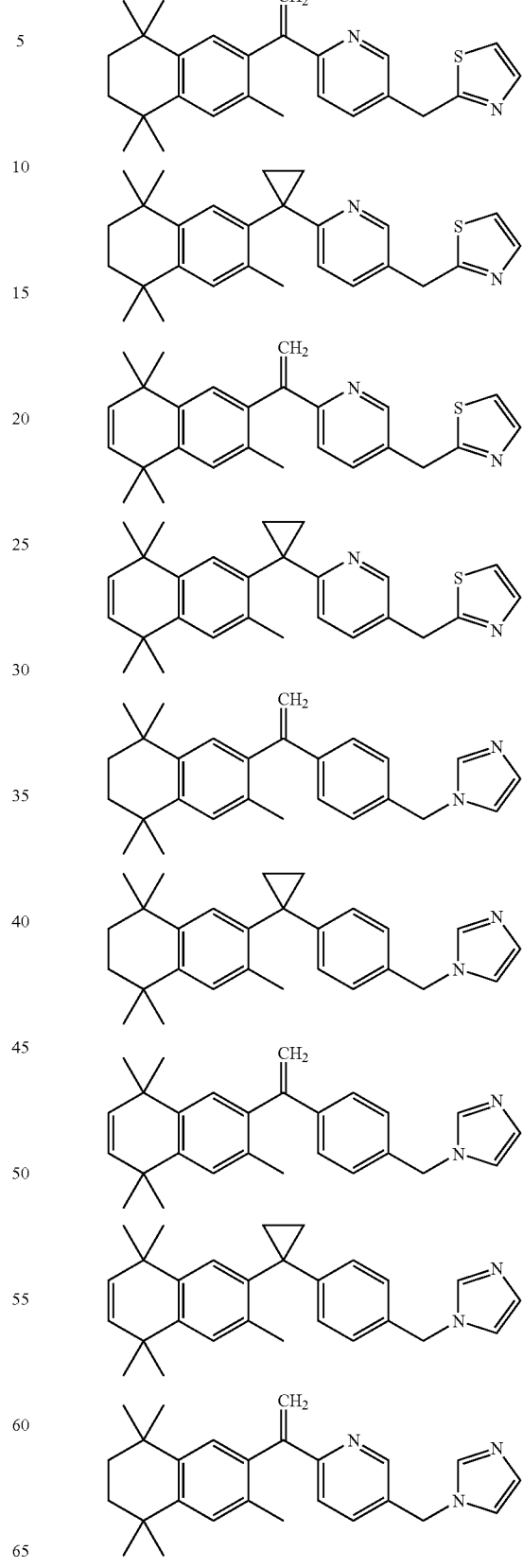

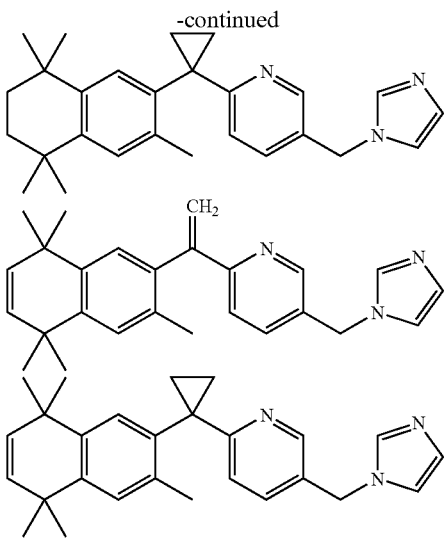

and pharmaceutically acceptable salts of the thereof

In another embodiment of the invention, there are provided pharmaceutical compositions comprising at least one of the compounds of the invention, as well as pharmaceutically acceptable pro-drugs and salts of such compounds, in a pharmaceutically acceptable vehicle, for enteral, parenteral, topical or ocular administration.

In another embodiment of the invention, there are provided pharmaceutical compositions comprising an effective regulating amount of at least one of the compounds of the invention in combination with a pharmaceutically acceptable vehicle, for control of cellular processes, cellular differentiation, cellular proliferation or apoptosis.

In another embodiment of the invention, there are provided pharmaceutical compositions comprising in a pharmaceutically acceptable vehicle suitable for enteral, parenteral, or topical administration, one or more compounds of the invention for treating a mammalian subject wherein said wherein said compound exerts its therapeutic effects via the in vivo modulation of lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

In another embodiment of the invention, there are provided pharmaceutical compositions comprising at least one of the compounds of the invention, in a pharmaceutically acceptable vehicle, for the treatment of carcinomas. Examples of carcinomas include mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, and the like.

In another embodiment of the invention, there are provided pharmaceutical compositions comprising at least one the compounds of the invention in combination with other chemotherapeutic agents, in a pharmaceutically acceptable vehicle, for the treatment of carcinomas. Examples of chemotherapeutic agents contemplated for use in the practice of this particular invention include Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Toremifene, Arzoxifene, Raloxifene, Tamoxifen, and the like.

In another embodiment of the invention, there are provided pharmaceutical compositions comprising at least one the compounds of the invention in combination with one or more antiestrogenic agents, in a pharmaceutically acceptable vehicle, for the treatment of mammary carcinoma. Examples of antiestrogenic agents contemplated for use in the practice of this particular invention include Toremifene, Arzoxifene, Raloxifene, Tamoxifen, and the like.

In another embodiment of the invention, there are provided cosmeceutical compositions comprising at least one the compounds of the invention, in a cosmetically acceptable vehicle, for dermal indications.

Before the present compounds, compositions and methods are disclosed and described, It is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds, reference to "a pharmaceutical carrier" includes mixtures of two or more such carriers, and the like.

Certain pharmaceutically acceptable salts of the invention are prepared by treating the novel compounds of the invention with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula A to base used is chosen to provide the ratio desired for any particular salts. For preparing, for example, the ammonium salts of the starting material, compounds of formula A can be treated with approximately one equivalent of the pharmaceutically acceptable base to yield a neutral salt. When calcium salts are prepared, approximately one-half a molar equivalent of base is used to yield a neutral salt, while for aluminum salts, approximately one-third a molar equivalent of base will be used.

The compounds of the invention according to formula A, including the pharmacologically acceptable pro-drugs or salts thereof, are useful to elicit, modulate and/or regulate selective gene expression by cellular receptors and provide control over cellular growth, proliferation and differentiation processes regulated by certain hormones or vitamins such as for example all-trans-retinoic acid, 13-cis-retinoic acid, 9cis-retinoic acid, vitamin D, thyroid hormone and the like. As noted above, the compounds of the invention are thus useful in the treatment of conditions and/or diseases that are regulated by the aforementioned entities. Examples of such conditions include for example cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, acne, psoriasis, aging, wrinkling, diabetes, hyperglycemia, bone calcification, thyroid conditions, and the like The compounds of the invention may be conveniently formulated into pharmaceutical compositions composed of one or more of the compounds together with a pharmaceutically acceptable vehicle as described in Remington's Pharmaceutical Sciences, latest edition, by E. W. Martin (Mack Publ. Co., Easton Pa.).

The compounds of the invention may be administered orally, parenterally (e.g., intravenously), by intramuscular injection, by intraperitoneal injection, topically, transdermally, or the like, although oral or topical administration is typically preferred. The amount of active compound administered will, of course, be dependent on the subject being treated, the subject's weight, the manner of administration and the judgment of the prescribing physician. The dosage will be in the range of about 2 microgram per kilogram per day to 4 milligram per kilogram per day.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels and the like, preferably in unit dosage form suitable for single administration of a precise dosage. The compositions will include, as noted above, an effective amount of the selected drug in combination with a pharmaceutically acceptable vehicle and, in addition, may include other medicinal agents, pharmaceutical agents, carriers, adjuvants, diluents and the like.

For solid compositions, conventional non-toxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable-compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Wherever required, flavoring, preserving, suspending, thickening, or emulsifying agents may also be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, as emulsions, or as sustained release delivery system.

EXAMPLES

Used herein, the following abbreviations have the following meanings: Me refers to methyl ($CH_3$—), Et refers to ethyl ($CH_3CH_2$—) i-Pr refers to isopropyl (($CH_3)_2CH_2$—), t-Bu or tert-butyl refers to tertiary butyl (($CH_3)_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to ter-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), DMF refers to N,N-dimethylformamide, DCM refers to dichloromethane ($CH_2Cl_2$), THF refers to tetrahydrofuran, EtOAc refers to ethyl acetate, $Et_2O$ refers to diethyl ether, MeCN refers to acetonitrile ($CH_3CN$), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCl refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAl refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4diyl diether, (DHQD)$_2$PHAL refers to dihydroquinidine phthalazine-1,4diyl diether, (DHQD)$_2$PYR refers to dihydroquinidine 2,5-diphenyl-4,6-pyrimidinediyl diether, LDA refers to lithium diisopropylamide, LiTMP refers to lithium 2,2,6,6-tetramethylpiperdinamide, n-BuLi refers to n-butyllithium, t-BuLi refers to tert-butyl lithium, IBA refers to 1-hydroxy-1,2-benziodoxol-3(1H)-one 1-oxide, $OsO_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, $Ac_2O$ refers to acetic anhydride, AcCl refers to acetyl chloride, TsOH refers to p-toluenesulfonic acid, TsCl refers to p-toluenesulfonyl chloride, MBHA refers to 4-methylbenzhydrylamine, BHA refers to benzhydrylamine, $ZnCl_2$ refers to zinc (II) dichloride, $BF_3$ refers to boron trifluoride, Y(OTf)$_2$ refers to yttrium (III) trifluoromethanesulfonate, Cu(BF$_4$)$_2$ refers to copper (II) tetrafluoroborate, LAH refers to lithium aluminum hydride (LiAlH$_4$), NaHCO$_3$ refers to sodium bicarbonate, $K_2CO_3$ refers to potassium carbonate, NaOH refers to sodium hydroxide, KOH refers to potassium hydroxide, LiOH refers to lithium hydroxide, HCl refers to hydrochloric acid, $H_2SO_4$ refers to sulfuric acid, MgSO$_4$ refers to magnesium sulfate, and Na$_2$SO$_4$ refers to sodium sulfate. 1H NMR refers to proton nuclear magnetic resonance, 13C NMR refers to carbon 13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, El refers to electron impact, FAB refers to fast atom bombardment, Cl refers to chemical ionization, HPLC refers to high pressure liquid chromatography, TLC refer to thin layer chromatography, $R_f$ refers to, $R_t$ refers to retention time, GC refers to gas chromatography, min is minutes, h is hours, rt or RT is room temperature, g is grams, mg is milligrams, L is liters, mL is milliliters, mol is moles and mmol is millimoles.

For all of the following examples, standard work-up and purification methods can be utilized and will be obvious to those skilled in the art. Synthetic methodologies can be used to practice the invention are shown in Schemes 1-4. These Schemes are intended to describe the applicable chemistry through the use of specific examples and are not necessarily indicative of the full scope of the invention.

Example 1

1,1,4,4,6-pentamethyl-1,2,3,4-tetrahydronaphthalene

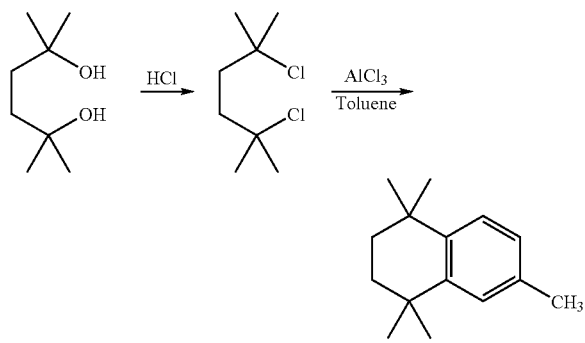

To 2,5-dimethyl-2,5-hexanediol (10 g, 68.5 mmol) in a 500 mL flask was added reagent grade concentrated HCl (150 mL) and the solution was stirred at ambient temperature for 1 h. Water (100 mL) and $CH_2Cl_2$ (100 mL) were then added slowly and the layers were separated. The aqueous layer was washed with additional $CH_2Cl_2$ (100 mL). The combined organic layers were dried over $MgSO_4$ and filtered thru silica gel pad. The solvent was removed to yield 10.9 g (87%) of 2,5-dichloro-2,5-dimethylhexane. The dichloride was dissolved in 150 mL of $CH_2Cl_2$ and 9.6 mL of toluene (90 mmol) was added. $AlCl_3$ (390 mg, 2.9 mol) was added in portions over 5 min at ambient temperature. HCl is evolved and the solution turns dark red. The reaction was placed in an ice-bath and quenched with deionized water (120 mL). Hexane (150 mL) was added and the organic layer was removed. The aqueous layer was washed with additional hexane (150 mL). The combined organic layers were washed with water (200 mL) and brine (100 mL) and dried over $MgSO_4$. The solvent was removed in vacuo to give 1,1,4,4,6-pentamethyl-1,2,3,4-tetrahydronaphthalene as a colorless oil that crystallized after storage at −20° C.

Yield: 12 g (91%); low melting white solid; $R_f$=0.7 in 100% hexane.

$^1$H NMR (CDCl$_3$, 300 MHz) δ 1.32 (s, 12H), 1.7 (s, 4H), 2.34 (s, 3H), 6.85 (dd, 1H), 7.14 (d, 1H), 7.22 (d, 1H)

$^{13}$C NMR (CDCl$_3$, 75 MHz) δ 21.54, 32.26, 32.32, 34.29, 34.51, 35.57, 35.63, 126.64, 126.75, 127.21, 134.93, 142.00, 144.83

Example 2

4-(3,5,5,8,8-Pentamethyl-5,6,7,8-tetrahydro-naphthalene-2-carbonyl)-benzoic acid methyl ester

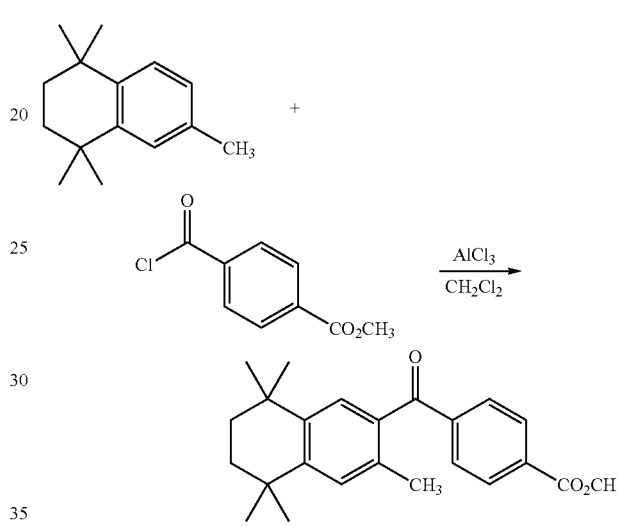

To a solution of 1,1,4,4,6-pentamethyl-1,2,3,4-tetrahydronaphthalene (470 mg, 2.33 mmol) in 10 mL of CHCl$_3$ was added the acid chloride shown (462 mg, 2.33 mmol), followed by AlCl$_3$ (930 mg, 6.97 mmol) at room temperature. The mixture was stirred at room temperature under nitrogen for 20 minutes. Water (10 mL) was added, and the product was extracted with CH$_2$Cl$_2$ three times. The combined organic fraction was dried over Na$_2$SO$_4$, filtered and purified by silica gel chromatography to yield 830 mg of the desired methyl ester product.

Yield: 0.83 g (98%); white solid; $R_f$=0.6 in 10% EtOAc/hexanes $^1$H NMR (CDCl$_3$, 300 MHz) δ 1.22 (6H, s), 1.34 (6H, s), 1.71 (4H, s), 2.38 (3H, s), 3.97 (3H, s), 7.23 (1H, s), 7.29 (1H, s), 7.91 (2H, d), 8.22 (2H, d)

Example 3

4-(3,5,5,8,8-Pentamethyl-5,6,7,8-tetrahydro-naphthalene-2-carbonyl)-benzoic acid

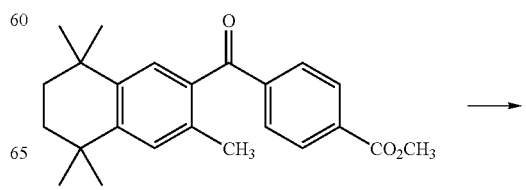

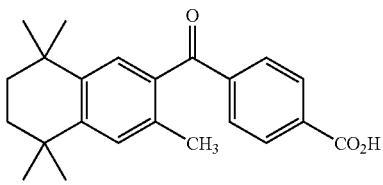

To a solution of 4-(3,5,5,8,8-Pentamethyl-5,6,7,8-tetrahydro-naphthalene-2carbonyl)-benzoic acid methyl ester (820 mg, 2.25 mmol) in 10 mL of THF and 10 mL of MeOH was added NaOH (22 mL of 1N solution, 22 mmol). The mixture was stirred at room temperature overnight. The mixture was acidified with HCl (23 mL of 1N solution, 23 mmol). The product was extracted with $CH_2Cl_2$ twice and EtOAc twice. The combined organic fraction was dried over $Na_2SO_4$, filtered and was used in the next step without purification.

Yield: 0.62 g (79%); white solid; $R_f$=0.45 in 1:1 EtOAc/hexanes $^1$H NMR (CDCl$_3$, 300 MHz) δ 1.23 (6H, s), 1.34 (6H, s), 1.72 (4H, s), 2.38 (3H, s), 7.23 (1H, s), 7.28 (1H, s), 7.91 (2H, d), 8.22 (2H, d)

Example 4

4-[1-(3,5,5,8,8-Pentamethyl-5,6,7,8-tetrahydro-naphthalen-2-yl)-vinyl]-benzoic acid

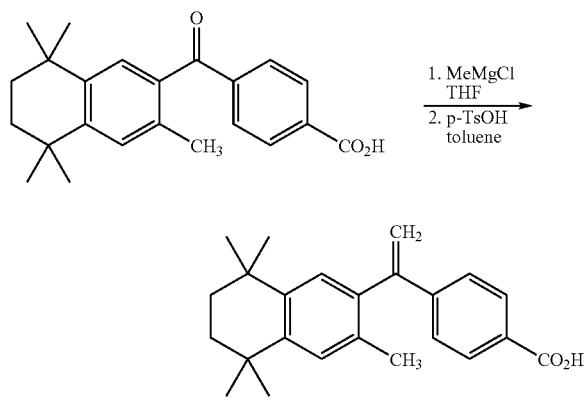

To a solution of 4-(3,5,5,8,8-Pentamethyl-5,6,7,8-tetrahydro-naphthalene-2-carbonyl)-benzoic acid (620 mg, 1.77 mmol) in 10 mL of THF was added MeMgCl (1.4 mL of a 3M THF solution, 4.2 mmol) at 0° C. The mixture was stirred at 0° C. for 10 min. Another portion of MeMgCl (1.4 mL of a 3M THF solution, 4.2 mmol) was added. The mixture was stirred at 0° C. for 30 min. The excess MeMgCl was quenched with the slow addition of water. 1N HCl was added until the mixture became acidic. The methyl tertiary alcohol product was extracted with $CH_2Cl_2$ twice and with EtOAc twice. The combined organic fraction was dried over $Na_2SO_4$, filtered, and concentrated in vacuo. Hexane is added to the mixture, which was filtered. The same procedure was repeated with $CH_2Cl_2$. The filtrates were discarded. EtOAc was added to the residue, and the filtrate was collected, concentrated in vacuo to give 403.3 mg of the crude tertiary alcohol, which was used in the next step without purification.

To the tertiary alcohol obtained above was added 20 mL of toluene and p-TsOH monohydrate (250 mg, 1.31 mmol). The mixture was refluxed with a Dean-Stark trap under nitrogen for 2 hours. Water was added to the mixture, and the product was extracted with EtOAc. The combined organic fraction was dried over $Na_2SO_4$, filtered and concentrated in vacuo. To remove the impurities, hexane is added to the mixture, which was filtered. The filtering procedure was repeated with $CH_2Cl_2$. The filtrates were discarded. EtOAc was then added to the residue, which was filtered again to collect the filtrate. The combined filtrate was concentrated in vacuo to give 373 mg of the product.

Yield: 0.37 g (60% over two steps); white solid; $R_f$=0.6 in 1:1 EtOAc/hexanes.

$^1$H NMR (CDCl$_3$, 300 MHz) δ 1.29 (6H, s), 1.33(6H, s), 1.72 (4H, s), 1.96(3H, s), 5.35 (1H, d), 5.84 (1H, d), 7.09 (1H, s), 7.13 (1H, s), 7.38 (2H, d), 8.02 (2H, d)

Example 5

{4-[1-(3,5,5,8,8-Pentamethyl-5,6,7,8-tetrahydro-naphthalen-2-yl)-vinyl]-phenyl}-methanol

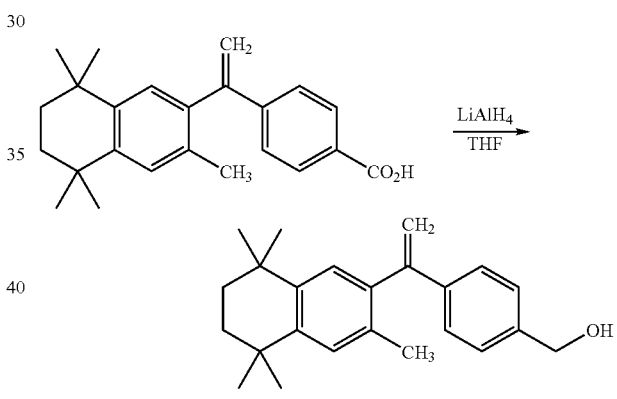

To a solution of 4-[1-(3,5,5,8,8-Pentamethyl-5,6,7,8-tetrahydro-naphthalen-2-yl)-vinyl]-benzoic acid in 10 mL of THF was added 300 mg of LiAlH$_4$ at 0° C. The mixture was stirred at room temperature overnight. The excess LiAlH$_4$ was quenched with EtOAc (3 mL). The mixture was stirred for 30 min. 1N HCl was added. A sequence of extraction with EtOAc, filtering, concentration in vacuo and column chromatography yielded 180 mg of the desired alcohol and 103 mg of its acetate. The acetate formed was dissolved in 2 mL of THF, 1 mL of MeOH and 1 mL of H$_2$O. NaOH (0.2 mL of a 1N solution, 0.2 mmol) was added. The mixture was stirred at room temperature for 1 hour. NH$_4$Cl solution was added, and the alcohol product was extracted with EtOAc. After drying over MgSO$_4$, filtering, concentration in vacuo and chromatography, 73.5 mg of the alcohol product was obtained. Total yield of the alcohol was therefore 253.5 mg.

Yield: 253.5 mg (85%); white solid; $R_f$=0.35 (3:1 hexanes/EtOAc) $^1$H NMR (CDCl$_3$, 300 MHz) δ 1.29 (6H, s), 1.32 (6H, s), 1.72 (4H, s), 1.99 (3H, s), 4.69 (2H, s), 5.21 (1H, d), 5.73 (1H, d), 7.07 (1H, s), 7.13 (1H, s), 7.29 (4H, s)

Example 6

4-[1-(3,5,5,8,8-Pentamethyl-5,6,7,8-tetrahydro-naphthalen-2-yl)-vinyl]-phenyl-acetonitrile

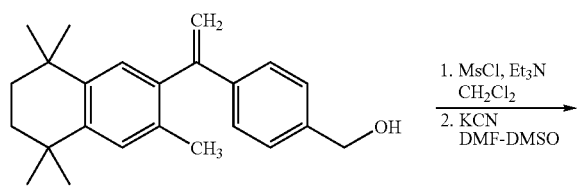

To a solution of {4-[1-(3,5,5,8,8-pentamethyl-5,6,7,8-tetrahydro-naphthalen-2-yl)-vinyl]-phenyl}-methanol (15.5 mg, 0.046 mmol) in 2 mL of $CH_2Cl_2$ was added $NEt_3$ (0.019 mL, 0.136 mmol), followed by Methanesulfonyl chloride (0.007 mL, 0.091 mmol) at 0° C. The mixture was stirred at 0° C. for 15 min, and was concentrated in vacuo. The mesylate obtained was used in the next step without purification.

To the mixture was added 1 mL of DMF and 2 mL of DMSO, followed by 200 mg of KCN. The mixture was stirred at 50° C. for 30 min. After aqueous workup (ether) and purification by PTLC, 12.6 mg of the nitrile product was obtained.

Yield: 12.6 mg (79%); $R_f$=0.9 (10% EtOAc/hexanes)

$^1$H NMR (CDCl$_3$, 300 MHz) δ 1.29 (6H, s), 1.32 (6H, s), 1.71 (4H, s), 1.98 (3H, s), 4.59 (2H, s), 5.23 (1H, d), 5.74 (1H, d), 7.07 (1H, s), 7.12 (1H, s), 7.27 (2H, d), 7.31 (2H, d)

Example 7

2-{4-[1-(3,5,5,8,8-Pentamethyl-5,6,7,8-tetrahydro-naphthalen-2-yl)-vinyl]-phenyl}-acetamide

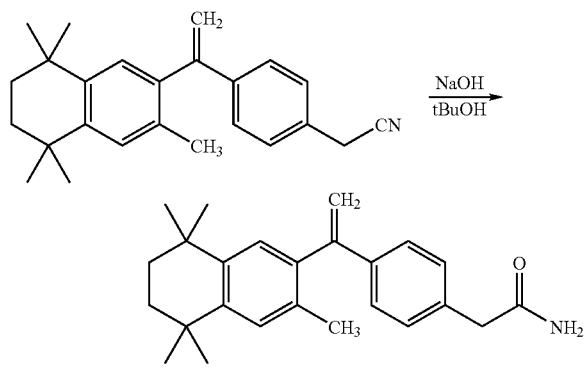

To a solution of 4-[1-(3,5,5,8,8-pentamethyl-5,6,7,8-tetrahydro-naphthalen-2-yl)-vinyl]-phenyl-acetonitrile (15 mg, 0.044 mmol) in 1 mL of t-BuOH was added NaOH (1 mL of 2N solution, 2 mmol). The mixture was heated at 100° C. for 24 hours. After acidification and extraction with EtOAc, the organic fraction was dried over Na$_2$SO$_4$, filtered and concentrated in vacuo. Purification by PTLC gave 5.2 mg of the amide product.

Yield: 5.2 mg (33%) $^1$H NMR (CDCl$_3$, 300 MHz) δ 1.30 (6H, s), 1.33 (6H, s), 1.72 (4H, s), 2.00 (3H, s), 4.7 (2H, s), 5.22 (1H, d), 5.74 (1H, d), 7.07 (1H, s), 7.13 (1H, s), 7.29 (4H, m)

Example 8

2-{4-[1-(3,5,5,8,8-Pentamethyl-5,6,7,8-tetrahydro-naphthalen-2-yl)-vinyl]-benzyl}-malonamide

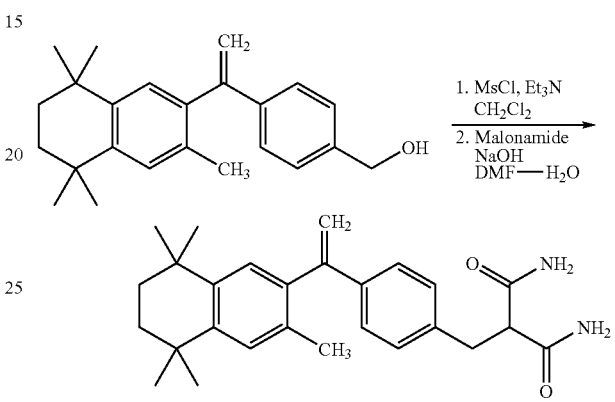

To a solution of {4-[1-(3,5,5,8,8-Pentamethyl-5,6,7,8-tetrahydro-naphthalen-2-yl)-vinyl]-phenyl}-methanol (394 mg, 1.18 mmol) in 10 mL of $CH_2Cl_2$ was added $NEt_3$ (0.5 mL, 3.59 mmol), followed by Methanesulfonyl chloride (0.18 mL, 2.33 mmol) at 0° C. The mixture was stirred at 0° C. for 15 min, and was concentrated in vacuo to give "mixture A".

In a separate flask, malonamide (1.2 g, 11.8 mmol) and NaOH (420 mg, 10.5 mol) were dissolved in 10 mL of DMF and 2 mL of H$_2$O. This mixture was added to "mixture A" and was stirred at room temperature overnight. NH$_4$Cl solution was added, and the bis-amide product was extracted with EtOAc. After drying over Na$_2$SO$_4$, filtering, concentration in vacuo, and chromatography, 167.7 mg of the product was obtained.

Yield: 167.7 mg (34% over 2 steps); white semi-solid; $R_f$=0.5 (10% MeOH/CH$_2$Cl$_2$)

$^1$H NMR (CDCl$_3$, 300 MHz) δ 1.29 (6H, s), 1.32 (6H, s), 1.71 (4H, s), 1.97 (3H, s) 2.27 (4H, s), 3.46 (2H, s), 5.19 (1H, d), 5.72 (1H, d), 7.06 (1H, s), 7.13 (1H, s), 7.23 (4H, m) m/z=441 (M+Na)

Example 9

3-{4-[1-(3,5,5,8,8-Pentamethyl-5,6,7,8-tetrahydro-naphthalen-2-yl)-vinyl]-benzyl}-imidazolidine-2,4-dione

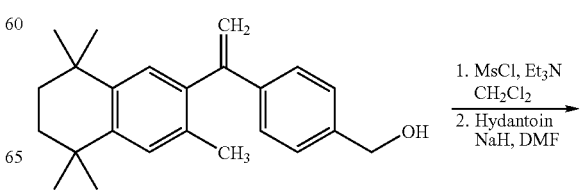

-continued

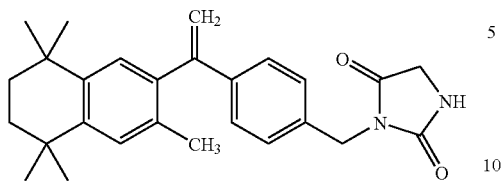

To a solution of {4-[1-(3,5,5,8,8-Pentamethyl-5,6,7,8-tetrahydro-naphthalen-2-yl)-vinyl]-phenyl}-methanol (37 mg, 0.11 mmol) in 3 mL of CH$_2$Cl$_2$ was added NEt$_3$ (0.1 mL, 0.72 mmol), followed by methanesulfonyl chloride (0.05 mL, 0.65 mmol) at 0° C. The mixture was stirred at 0° C. for 15 min, and was concentrated in vacuo to give "mixture B". In a separate flask, 10 mL of DMF was added to hydantoin (300 mg, 3.0 mmol). NaH (72 mg, 3.0 mmol) was added. The mixture was stirred at room temperature for 5 minutes, and was transferred to "mixture B". The new mixture was stirred at room temperature overnight. NH$_4$Cl solution was added, and the product was extracted with EtOAc. The organic fraction was dried over Na$_2$SO$_4$, filtered, concentrated in vacuo, and purified by PTLC to yield 20.1 mg of the product.

Yield: 20.1 mg (44% over 2 steps); white semi-solid; R$_f$=0.6 (EtOAc) $^1$H NMR (CDCl$_3$, 300 MHz) δ 1.28 (6H, s), 1.31 (6H, s), 1.70 (4H, s), 1.97 (3H, s), 3.98 (2H, s), 4.66 (2H, s), 5.19 (1H, d), 5.33 (1H, broad), 5.70 (1H, d), 7.06 (1H, s), 7.09 (1H), s), 7.23 (2H, d), 7.33 (2H, d)

Example 10

3-{4-[1-(3,5,5,8,8-Pentamethyl-5,6,7,8-tetrahydro-naphthalen-2-yl)-vinyl]-benzyl}-thiazolidine-2,4-dione

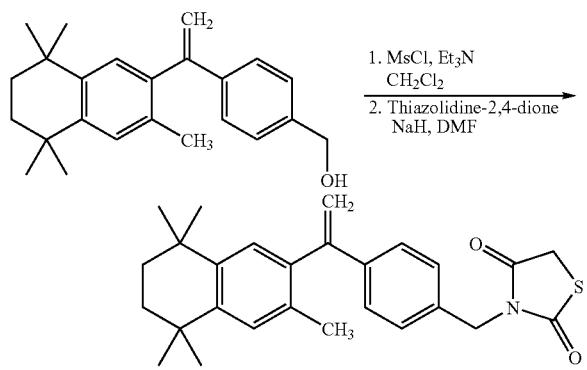

Adopting the procedure outlined for example 9 using 40.0 mg (0.12 mmol) of {4-[1-(3,5,5,8,8-Pentamethyl-5,6,7,8-tetrahydro-naphthalen-2-yl)-vinyl]-phenyl}-methanol, 0.05 mL of Methanesulfonyl chloride, 0.10 mL of NEt$_3$, 280 mg of thiazolidine-2,4-dione, and 57 mg of NaH, 20.1 mg of the product was obtained.

Yield: 20.1 mg (39% over 2 steps); oil $^1$H NMR (CDCl$_3$, 300 MHz) δ 1.28 (6H, s), 1.32 (6H, s), 1.71 (4H, s), 1.97 (3H, s), 3.95 (2H, s), 4.76 (2H, s), 5.21 (1H, d), 5.72 (1H, d), 7.06 (1H, s), 7.10 (1H, s), 7.24 (2H, d), 7.31 (2H, d)

Example 11

1-Methyl-3-{4-[1-(3,5,5,8,8-pentamethyl-5,6,7,8-tetrahydro-naphthalen-2-yl)-vinyl]-benzyl}-imidazo-lidine-2,4-dione

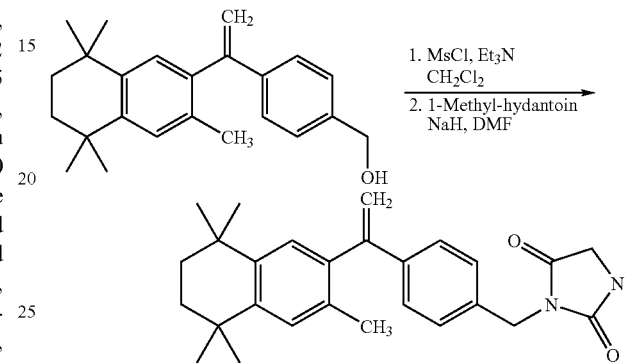

Adopting the procedure outlined for example 9 using 40.0 mg (0.12 mmol) of {4-[1-(3,5,5,8,8-Pentamethyl-5,6,7,8-tetrahydro-naphthalen-2-yl)-vinyl]-phenyl}-methanol, 0.05 mL of methanesulfonyl chloride, 0.10 mL of NEt$_3$, 300 mg of 1-methyl-hydantoin, and 63 mg of NaH, 22.0 mg of the product was obtained.

Yield: 22.0 mg (43% over 2 steps); oil $^1$H NMR (CDCl$_3$, 300 MHz) δ 1.28 (6H, s), 1.31 (6H, s), 1.70 (4H, s), 1.97 (3H, s), 2.99 (3H, s), 3.86 (2H, s), 4.64 (2H, s), 5.19 (1H, d), 5.70 (1H, d), 7.06 (1H, s), 7.09 (1H, s), 7.22 (2H, d), 7.33 (2H, d)

Example 12

5,5-Dimethyl-3-{4-[1-(3,5,5,8,8-pentamethyl-5,6,7,8-tetrahydro-naphthalen-2-yl)-vinyl]-benzyl}-imidazolidine-2,4-dione

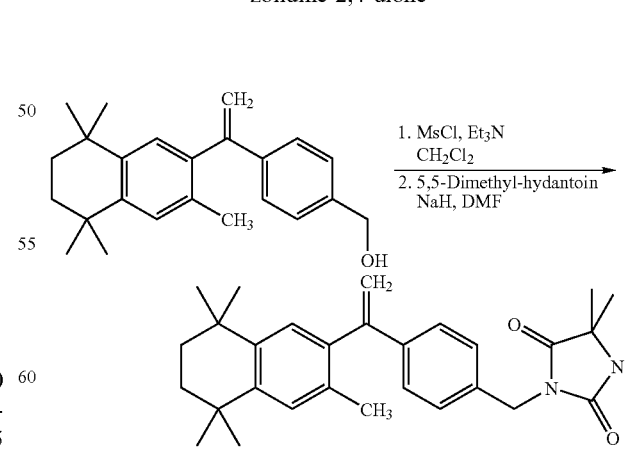

Adopting the procedure outlined for example 9 using 40.0 mg (0.12 mmol) of {4-[1-(3,5,5,8,8-Pentamethyl-5,6,7,8-tetrahydro-naphthalen-2-yl)-vinyl]-phenyl}-methanol, 0.05 mL of methanesulfonyl chloride, 0.10 mL of NEt$_3$, 300 mg of 5,5-dimethylhydantoin, and 56 mg of NaH, 32.0 mg of the product was obtained.

Yield: 32.0 mg (60% over 2 steps); oil $^1$H NMR (CDCl$_3$, 300 MHz) δ 1.28 (6H, s), 1.31 (6H, s), 1.43 (6H, s), 1.70 (4H, s), 1.96 (3H, s), 4.64 (2H, s), 5.19 (1H, d), 5.70 (1H, d), 5.92 (1H, broad), 7.06 (1H, s), 7.10 (1H, s), 7.22 (2H, d), 7.26 (2H, d)

Example 13

3-{4-[1-(3,5,5,8,8-Pentamethyl-5,6,7,8-tetrahydro-naphthalen-2-yl)-vinyl]-benzyl}-dihydro-pyrimidine-2,4-dione

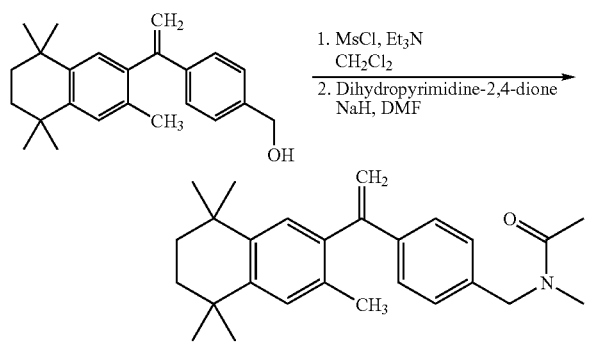

Adopting the procedure outlined for example 9 using 40.0 mg (0.12 mmol) of {4-[1-(3,5,5,8,8-Pentamethyl-5,6,7,8-tetrahydro-naphthalen-2-yl)-vinyl]-phenyl}-methanol, 0.05 mL of methanesulfonyl chloride, 0.10 mL of NEt$_3$, 300 mg of dihydropyrimidine-2,4-dione, and 63 mg of NaH, 28.4 mg of the product was obtained.

Yield: 28.4 mg (55% over 2 steps); white semi-solid $^1$H NMR (CDCl$_3$, 300 MHz) δ 1.28 (6H, s), 1.32 (6H, s), 1.71 (4H, s), 1.98 (3H, s), 2.75 (2H, m), 3.39 (2H, m), 4.94 (2H, s), 5.17 (1H, m), 5.70 (1H, m), 6.12 (1H, broad), 7.06 (1H, s), 7.10 (1H, s), 7.20 (2H, d), 7.29 (2H, d)

Example 14

1,5,5-Trimethyl-3-{4-[1-(3,5,5,8,8-pentamethyl-5,6,7,8-tetrahydro-naphthalen-2-yl)-vinyl]-benzyl}-imidazolidine-2,4-dione

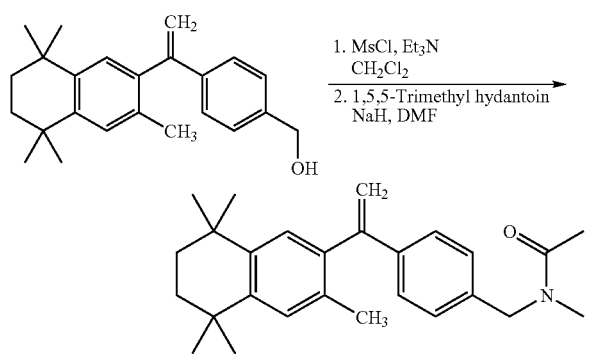

Adopting the procedure outlined for example 9 using 40.0 mg (0.12 mmol) of {4-[1-(3,5,5,8,8-Pentamethyl-5,6,7,8-tetrahydro-naphthalen-2-yl)-vinyl]-phenyl}-methanol, 0.05 mL of Methanesulfonyl chloride, 0.10 mL of NEt$_3$, 300 mg of 1,5,5-trimethyl-hydantoin, and 51 mg of NaH, 21.0 mg of the product was obtained.

Yield: 21.0 mg (38% over 2 steps); oil
$^1$H NMR (CDCl$_3$, 300 MHz) δ 1.28 (6H, s), 1.31 (6H, s), 1.38 (6H, s), 1.70 (4H, s), 1.96 (3H, s), 2.88 (3H, s), 4.64 (2H, s), 5.18 (1H, d), 5.69 (1H, d), 7.06 (1H, s), 7.10 (1H, s), 7.22 (2H, d), 7.28 (2H, d)

Example 15

A375 Tumor Cell Proliferation Assay

A375 cells (5,000 per well in 90% RPMI-1640 plus 10% Fetal Bovine Serum [FBS]) were pre-incubated in a black clear bottom 96-well plate in an atmosphere of 5% CO$_2$ at 37° C. for 24 hours. Stock solutions of compounds in DMSO were diluted using a buffer and dilutions were added to each well. The final concentration DMSO in each well did not exceed 0.5%. The final assay pH was 7.4. The cells were incubated in RPMI-1 640 with each compound for an additional 72 to 168 hours. Alamar Blue was added and the plate was incubated for an additional 12 hours. Fluorescence intensity was measured using a Gemini plate reader with excitation at 530 nm and emission at 590 nm. A decrease of 50 percent or more (≧50%) in fluorescence intensity relative to vehicle treated controls is an indication of significant anti-cancer activity.

| | Reference Data | | |
|---|---|---|---|
| Compound | IC$_{50}$ (μM) | TGI (M) | LC$_{50}$ (μM) |
| Doxorubicin | 0.19 | 0.30 | 8.00 |
| Mitomycin | 4.20 | 8.00 | 10.0 |

IC$_{50}$ (50% Inhibitory Concentration): Test compound concentration where the increase in number or mass of cells from time$_0$ to 72 to 168 hours is reduced 50% relative to the corresponding vehicle controls.

TGI (Total Growth Inhibition): Test compound concentration where the increase in number or mass of cells after 72 to 168 hours is reduced to equal that at time t=0.

LC$_{50}$ (50% Lethal Concentration): Test compound concentration where the number or mass of cells after 72 to 168 hours is reduced 50% relative to that at time t=0.

Example 16

T47D Tumor Cell Proliferation Assay

T-47D cells (15,000 per well in 90% RPMI-1640 medium plus 10% Fetal Bovine Serum [FBS]) were pre-incubated in a black clear bottom 98-well plate in an atmosphere of 5% CO$_2$ at 37° C. for 24 hours. Stock solutions of compounds in DMSO were diluted using a buffer and dilutions were added to each well in the presence or absence 20 μM Tamoxifen. The final concentration DMSO in each well did not exceed 0.5%. The final assay pH was 7.4. The cells were incubated in RPMI-1640 with each compound for an additional 72 to 192 hours. Alamar Blue was added and the plate was incubated for an additional 12 hours. Fluorescence intensity was measured using a Gemini plate reader with excitation at 530 nm and emission at 590 nm. A decrease of 50 percent or more (≧50%) in fluorescence intensity relative to vehicle treated controls is an indication of significant anti-cancer activity.

Example 17

SCC103 Tumor Cell Proliferation Assay

SCC 103 cells (15,000 per well in 90% EMEM medium plus 10% Fetal Bovine Serum [FBS]) were pre-incubated in a black clear bottom 96-well plate in an atmosphere of 5% $CO_2$ at 37° C. for 24 hours. Stock solutions of compounds in DMSO were diluted using a buffer and dilutions were added to each well. The final concentration DMSO in each well did not exceed 0.5%. The final assay pH was 7.4. The cells were incubated in EMEM medium for an additional 72 hours. Alamar Blue (10% of culture volume) was added and the plate was incubated for an additional 12 hours. Fluorescence intensity was measured using a Gemini plate reader with excitation at 530 nm and emission at 590 nm. A decrease of 50 percent or more ($\geq 50\%$) in fluorescence intensity relative to vehicle treated controls is an indication of significant anticancer activity.

Example 18

HepG2 Tumor Cell Proliferation Assay

HepG2 cells (5,000 per well in 90% EMEM medium plus 10% Fetal Bovine Serum [FBS]) were pre-incubated in a black clear bottom 98-well plate in an atmosphere of 5% $CO_2$ at 37° C. for 24 hours. Stock solutions of compounds in DMSO were diluted using a buffer and dilutions were added to each well. The final concentration DMSO in each well did not exceed 0.5%. The final assay pH was 7.4. The cells were incubated in EMEM medium for an additional 72 hours. Alamar Blue (10% of culture volume) was added and the plate was incubated for an additional 12 hours. Fluorescence intensity was measured using a Gemini plate reader with excitation at 530 nm and emission at 590 nm. A decrease of 50 percent or more ($\geq 50\%$) in fluorescence intensity relative to vehicle treated controls is an indication of significant anticancer activity.

Example 19

Radioactive Ligand Binding Assay

[$^3$H]-9 cis-retinoic acid (29 Ci/mmol) and MicroSpin G-25 Columns were purchased from Amersham Biosciences (Piscataway, N.J.). Unlabeled 9-cis retinoic acid was purchased from Affinity BioReagents (Golden, Colo.). The retinoic acid receptor subtype RXRγ was purchased from BIOMOL (Plymouth Meeting, Pa.). Stock solution of 9cis-retinoic acid, was prepared as either 5 mM ethanol or DMSO stock solutions, and serial dilutions were carried out in 1:1 DMSO-ethanol. The assay buffer consisted of the following for receptor assay: 8% glycerol, 120 mM KCl, 8 mM Tris, 5 mM CHAPS, 4 mM DTT, and 0.24 mM PMSF, pH 7.4, at room temperature.

The receptor binding assay was performed with a final volume of 250 μL containing from 10 to 20 μg of protein, plus 10 nM [$^3$H]-9-cis-retinoic acid, RXRγ and varying concentrations of competing ligand (0-10$^{-5}$ M). Incubations were carried out at 4° C. for 18 h. Equilibrium under these conditions of buffer and temperature was achieved by 4 h. Nonspecific binding was defined as that binding remaining in the presence of 1000 nM unlabeled 9-cis-retinoic acid. The receptor-ligand complex was separated from unincorporated [$^3$H]-9-cis-retinoic acid by applying the binding reaction solution to pre-spun MicroSpin G-25 Column and centrifuged at 735 G for 2 minutes in a microcentrifuge. The amount of receptor-ligand complex was determined by liquid scintillation counting of the purified receptor-ligand complex. After correcting for non-specific binding, the $IC_{50}$ value was determined. The $IC_{50}$ value is defined as the concentration of competing ligand required to decrease specific binding by 50%; the $IC_{50}$ value was determined graphically from a log-logit plot of the data. $K_d$ value for 9-cis-retinoic acid using a modified Cheng-Prussof equation as described by Motulsky.

Although the invention has been described with reference to the above examples, it will be understood that modifications and variations are encompassed within the spirit and scope of the invention. Accordingly, the invention is limited only by the following claims.

The invention claimed is:

1. A compound having structural Formula A

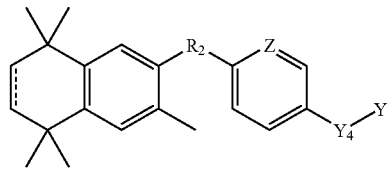

Formula A and pharmaceutically acceptable salts thereof, wherein:
said dashed line indicates an optional double bond;
Z is selected from the group consisting of CH and N;
Y is attached to any position on $Y_4$, wherein Y is selected from the group consisting of cyano, —$COOR_{21}$, —$CONR_{22}R_{23}$, —$CONR_{21}NR_{22}R_{23}$, heteroaryl, and compounds having a structural formula selected from the group consisting of $A_1, A_2, A_3, A_4, A_5$;

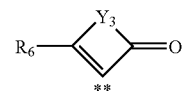

$A_1$

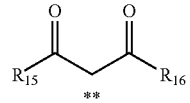

$A_2$

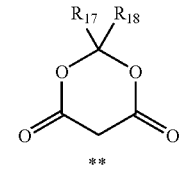

$A_3$

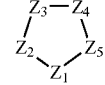

$A_4$

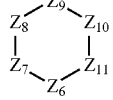

$A_5$ $Y_3$ is selected from the group consisting of $C_{2-8}$ alkyl and $C_{2-8}$ substituted alkyl;

$Y_4$ is $C_{1-6}$ alkyl;

$Z_2$, $Z_5$, $Z_7$ and $Z_{11}$ are each independently selected from the group consisting of C=O, C=S, C=NR$_{17}$, C=NNR$_{22}$R$_{23}$, C=NOR$_{17}$, and CR$_{24}$R$_{25}$;

$Z_1$, $Z_3$, $Z_4$, $Z_6$, $Z_8$, $Z_9$ and $Z_{10}$ are each independently selected from the group consisting of O, S, N, —NH, alkylamino, arylamino, and CR$_{24}$R$_{25}$, with the proviso that none of $Z_1$, $Z_3$, $Z_4$, $Z_6$, $Z_8$, $Z_9$ and $Z_{10}$ is O or S if $Z_1$, $Z_3$, $Z_4$, $Z_6$, $Z_8$, $Z_9$ or $Z_{10}$ is the point of attachment to $Y_4$, with the further proviso that $Z_3$ and $Z_4$ cannot both be O at the same time, with the further proviso that $Z_8$ and $Z_9$ cannot both be O at the same time, with the further proviso that $Z_9$ and $Z_{10}$ cannot both be O at the same time, with the further proviso that $Z_3$, $Z_4$, $Z_8$, $Z_9$ or $Z_{10}$ can form double bonds to each other provided that none of $Z_3$, $Z_4$, $Z_8$, $Z_9$ or $Z_{10}$ is O or S;

$R_2$ is selected from the group consisting of

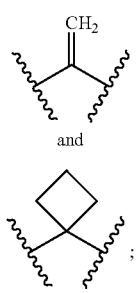

and

;

$R_6$ is selected from the group consisting of —OH, alkyloxy, aryloxy, alkylcarboxy, arylcarboxy, —SH, alkylthio, arylthio, —NH$_2$, alkylamino, arylamino, N-aryl-N-alkylamino, —NHNH$_2$, alkylhydrazino, arylhydrazino, N-aryl-N-alkylhydrazino, —NHOR$_{17}$, —O(P=O)(OR$_{17}$)(OR$_{18}$), —OCH$_2$O(P=O)(OR$_{17}$)(OR$_{18}$), and —OSO$_3$R$_{17}$, $R_{15}$ and $R_{16}$ are each independently selected from the group consisting of —OH, alkyloxy, aryloxy, —NH$_2$, alikylamino, arylamino, N-aryl-N-alkylamino, —NHNH$_2$, alkylhydrazino, arylhydrazino, N-aryl-N-alkylhydrazino, —NHOR$_{17}$, alkyl, and aryl;

$R_{17}$ and $R_{18}$ are each independently selected from the group consisting of hydrogen, alkyl, and aryl;

$R_{21}$, $R_{22}$ and $R_{23}$ are each independently selected from the group consisting of hydrogen, alkyl, aryl, or $R_{22}$ and $R_{23}$ are taken together with the nitrogen to which they are attached forming a saturated cyclic or unsaturated cyclic system containing 3 to 8 carbon atoms with at least one substituent as defined herein; and $R_{24}$ and $R_{25}$ are each independently selected from the group consisting of hydrogen, halogen, alkyl, and aryl.

2. Compounds selected from a group consisting of

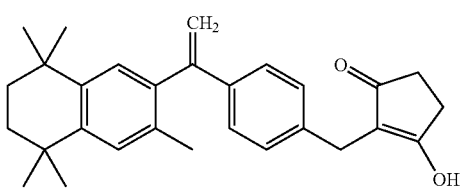

-continued

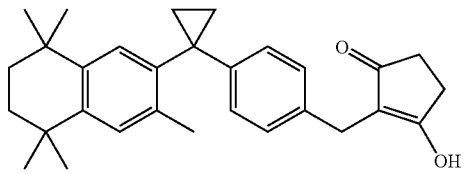

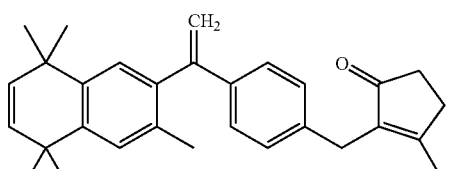

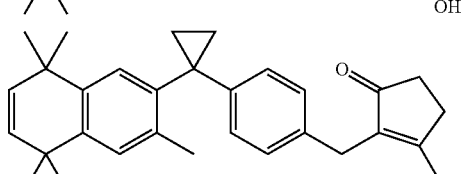

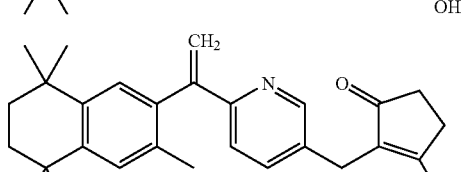

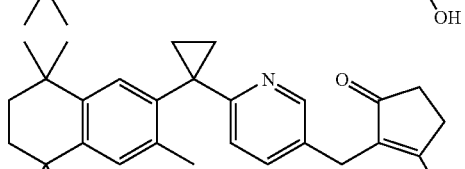

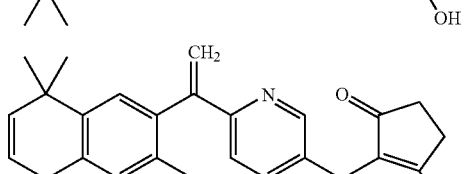

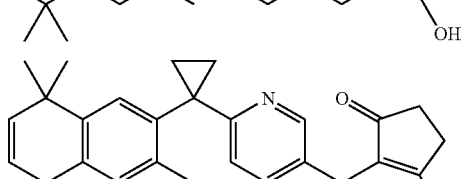

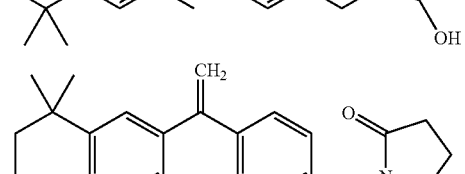

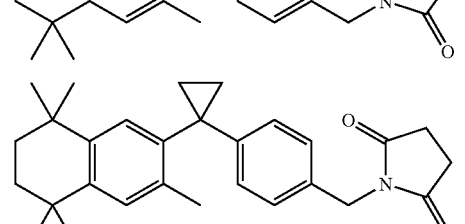

-continued
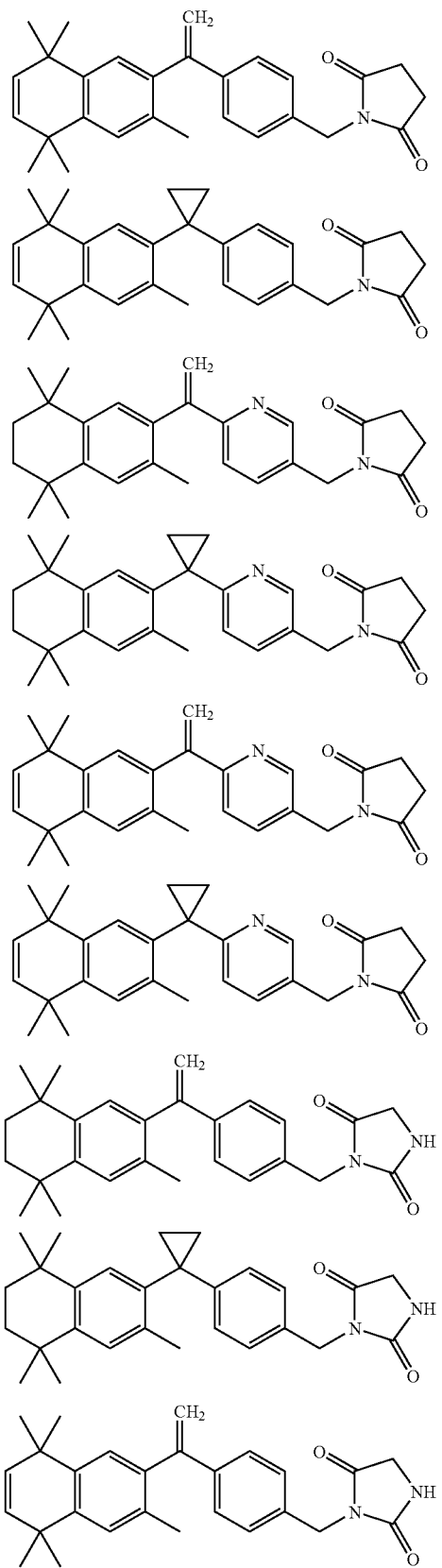
-continued
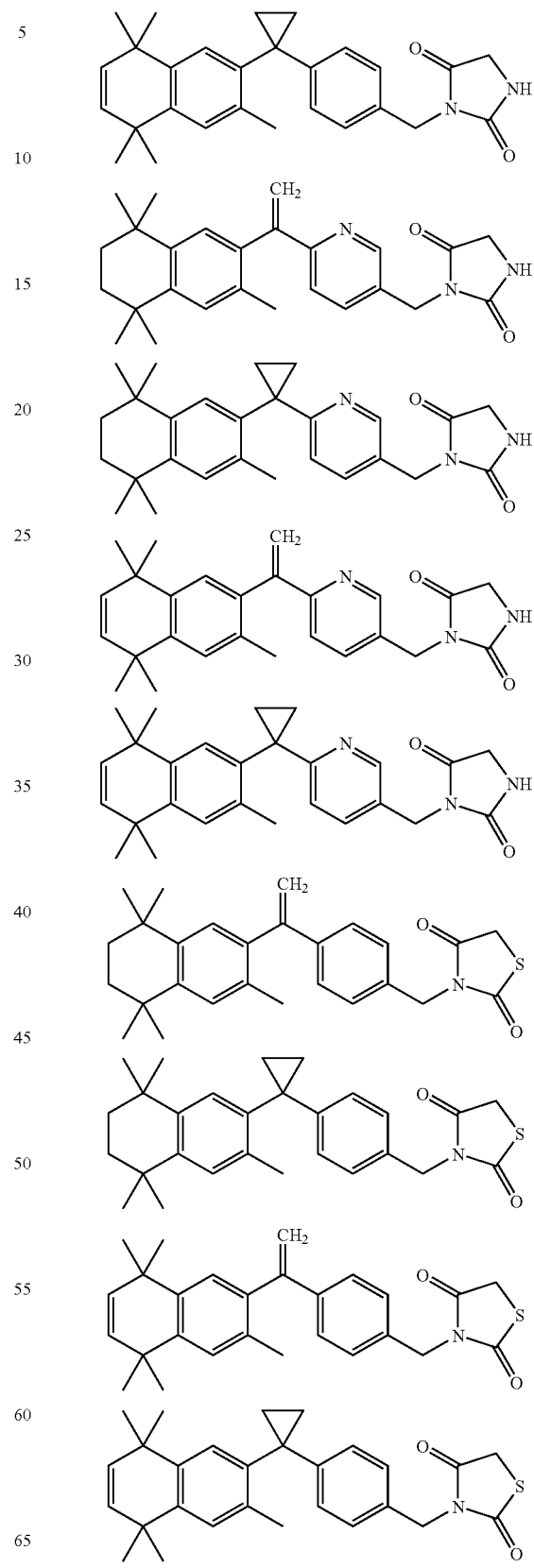

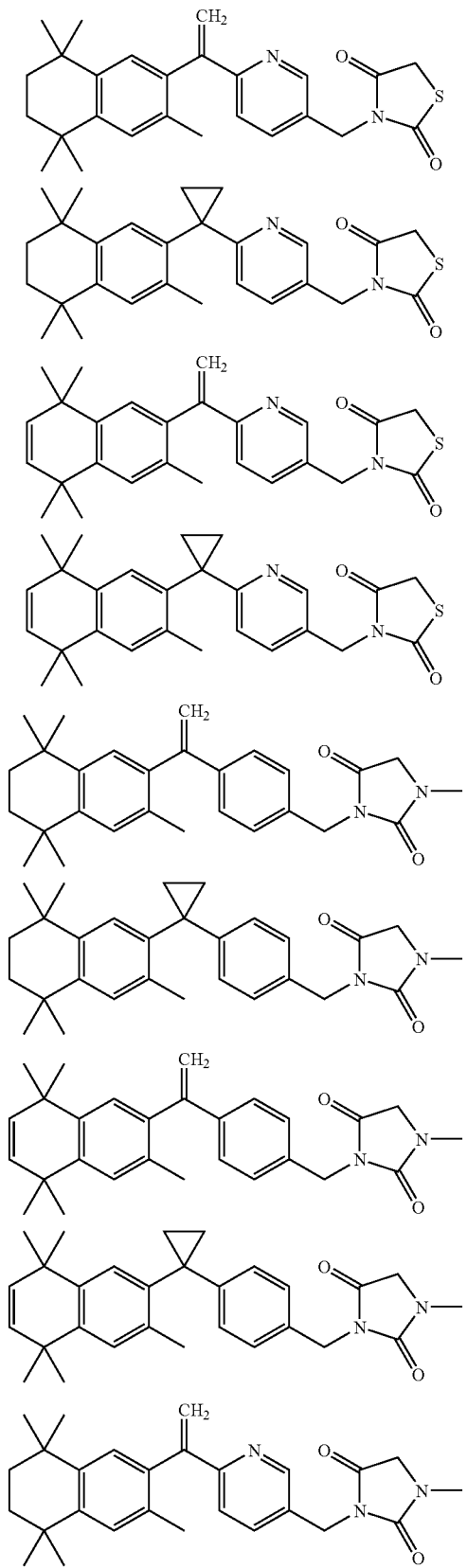
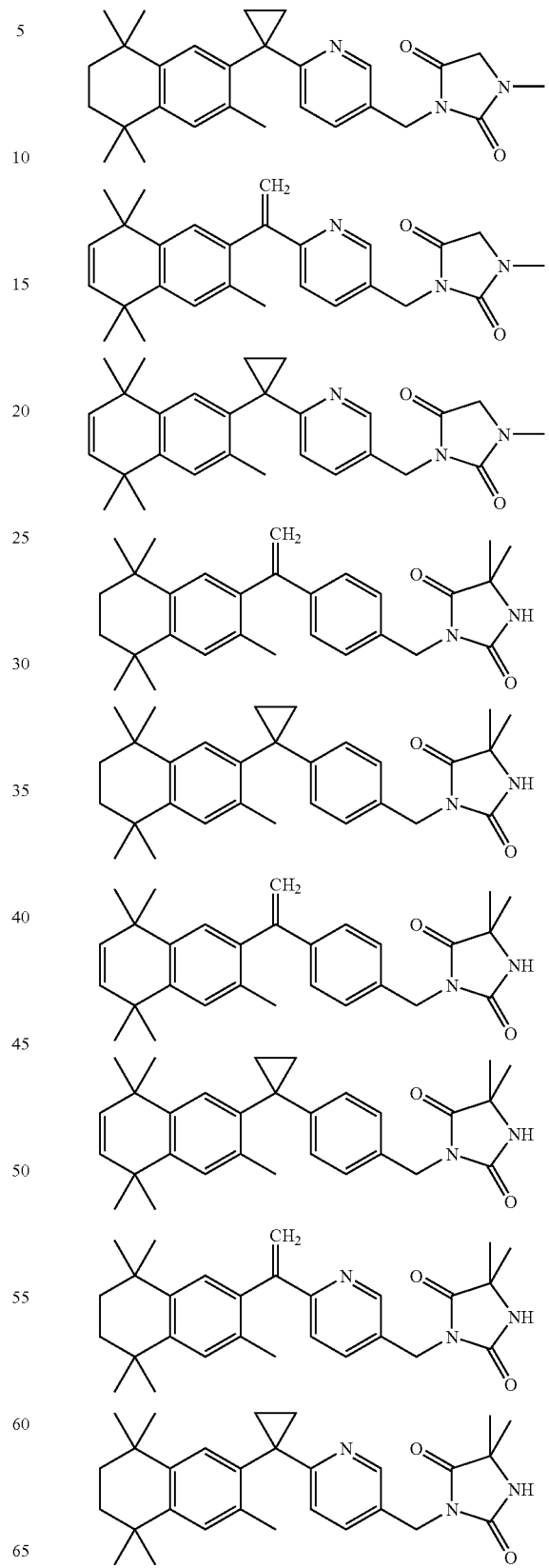

69
-continued
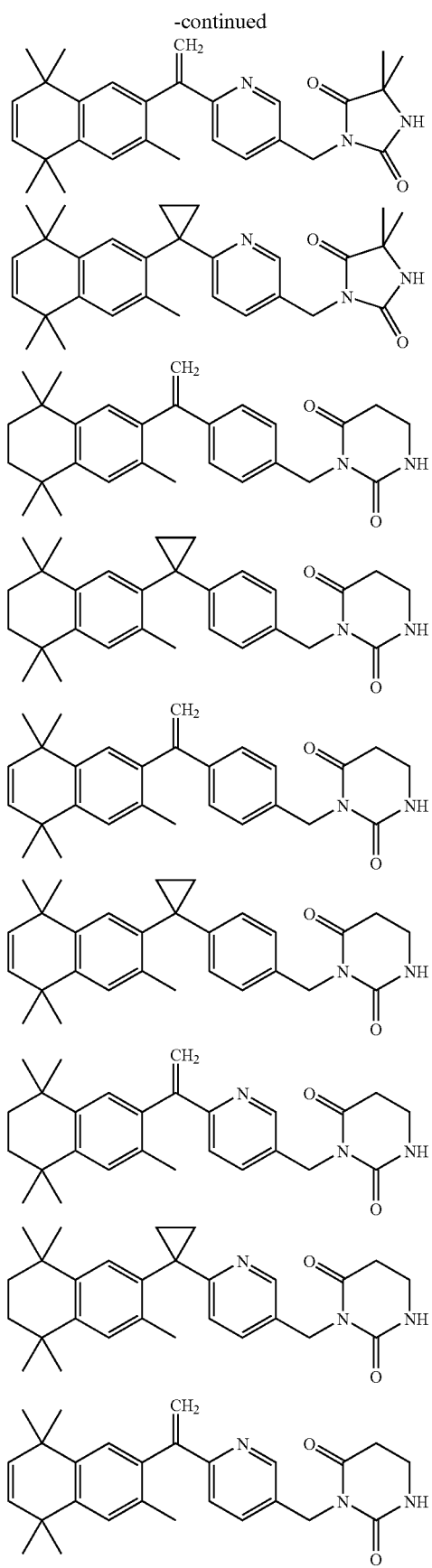
70
-continued
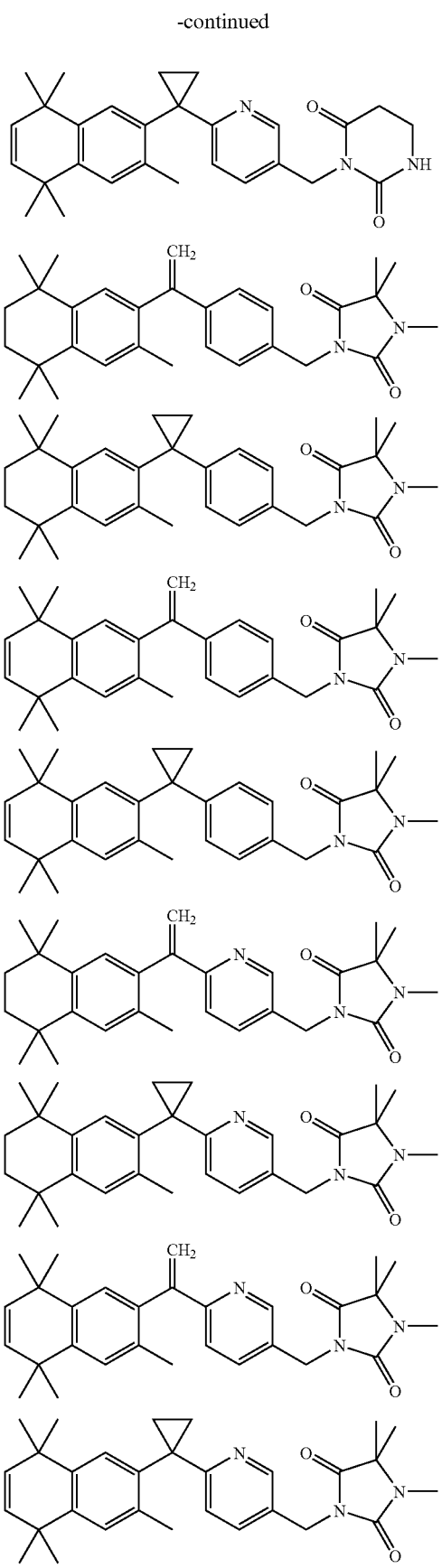

-continued
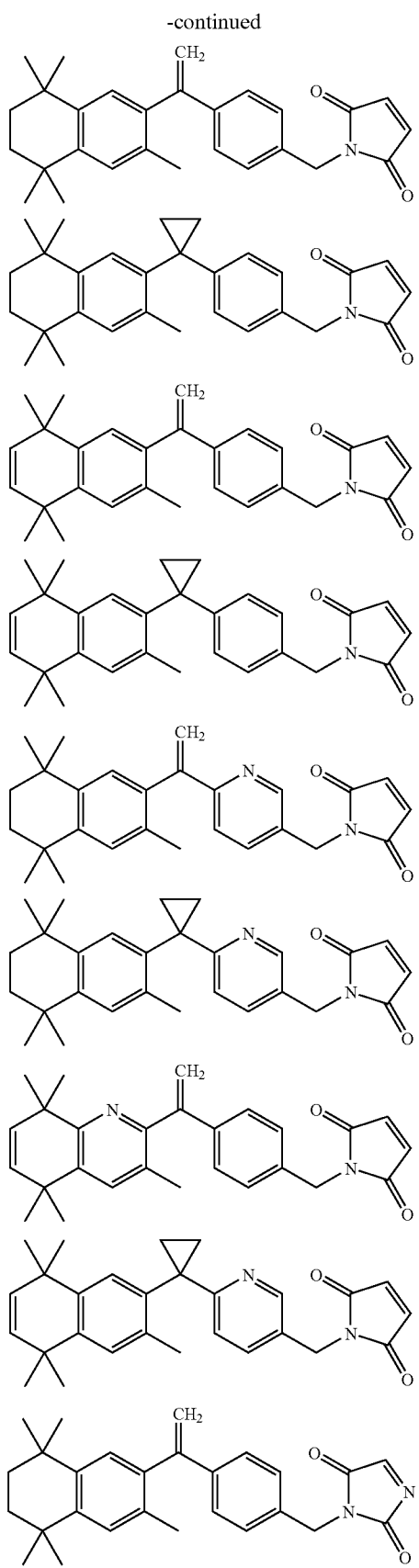
-continued
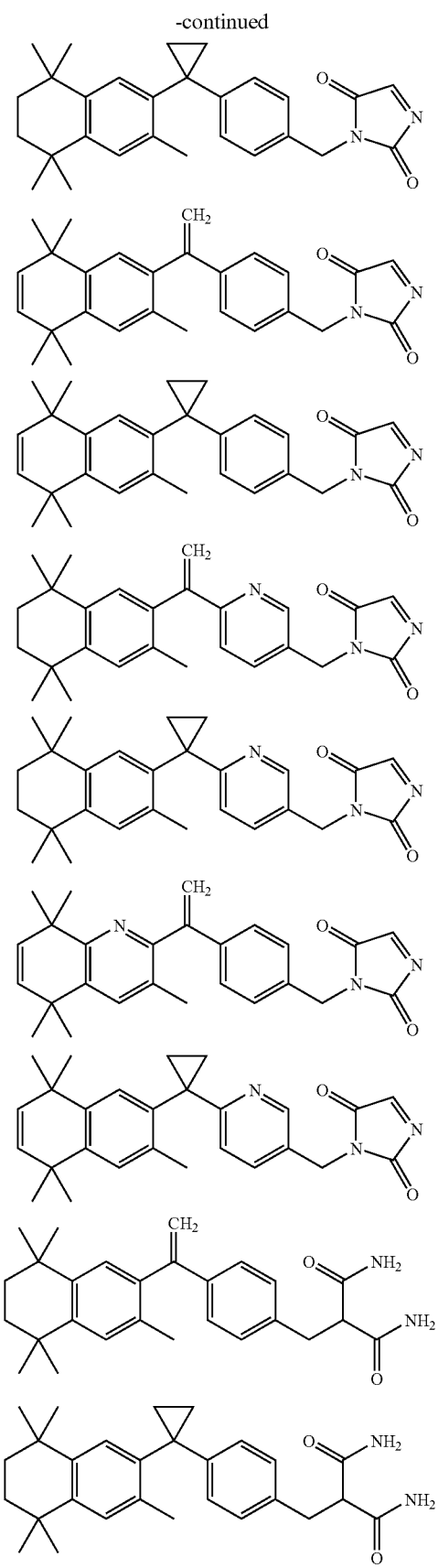

-continued
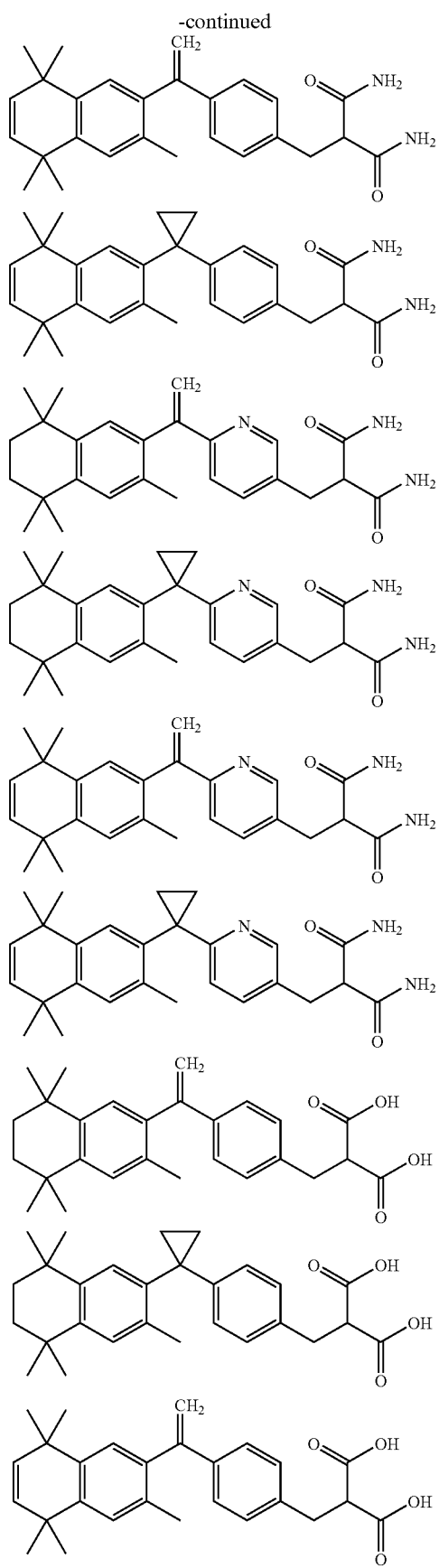
-continued
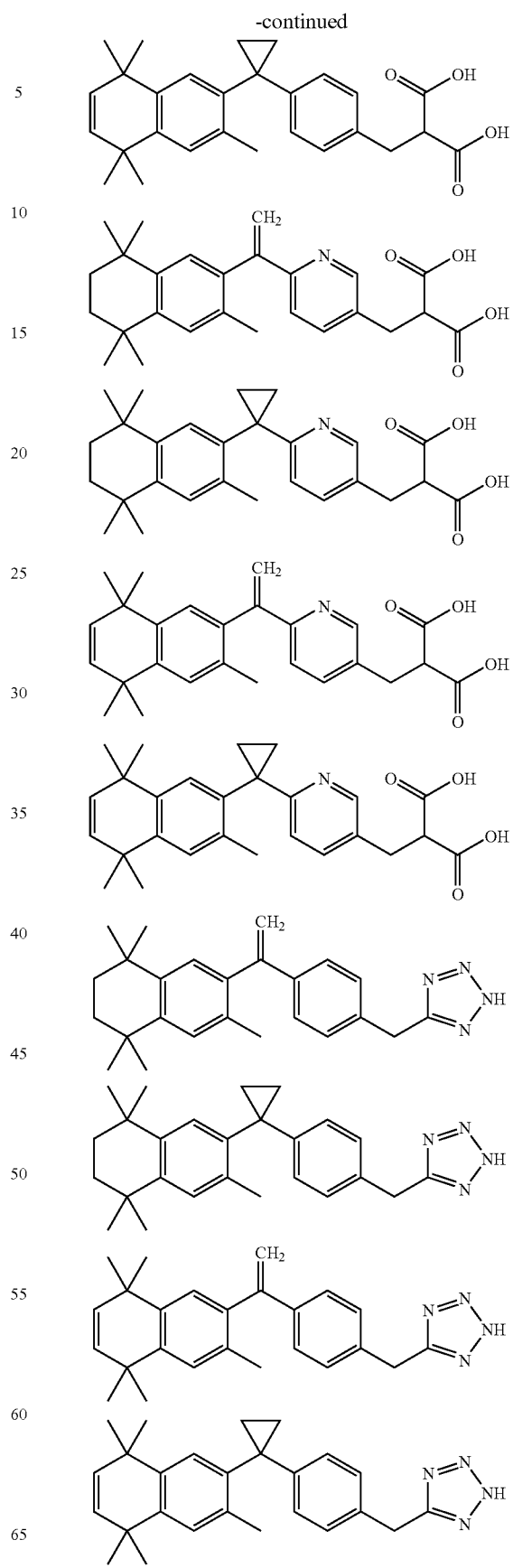

-continued
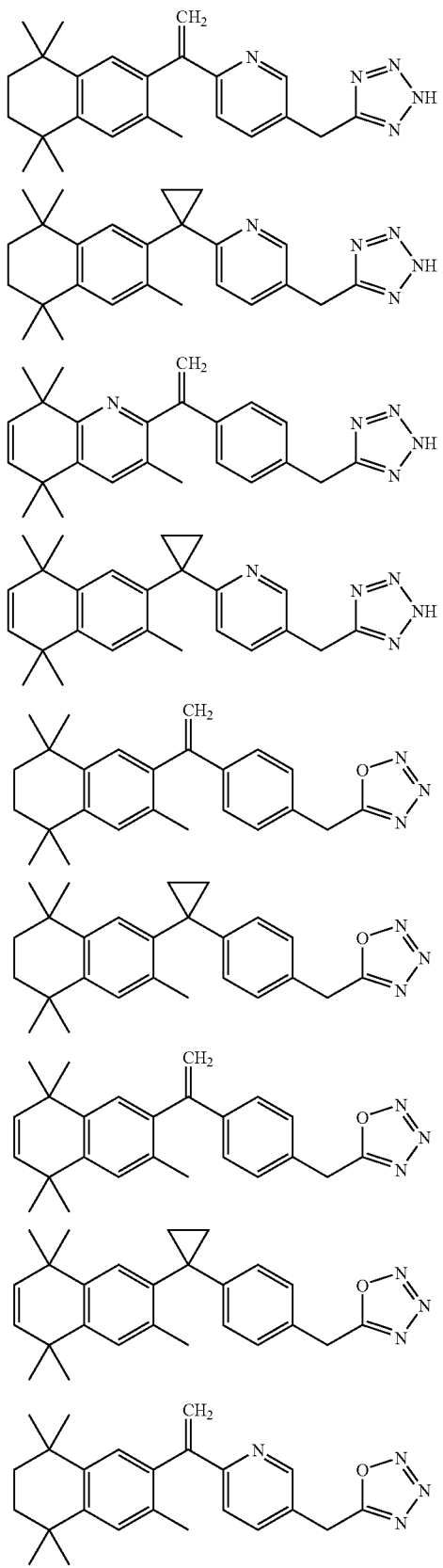
-continued
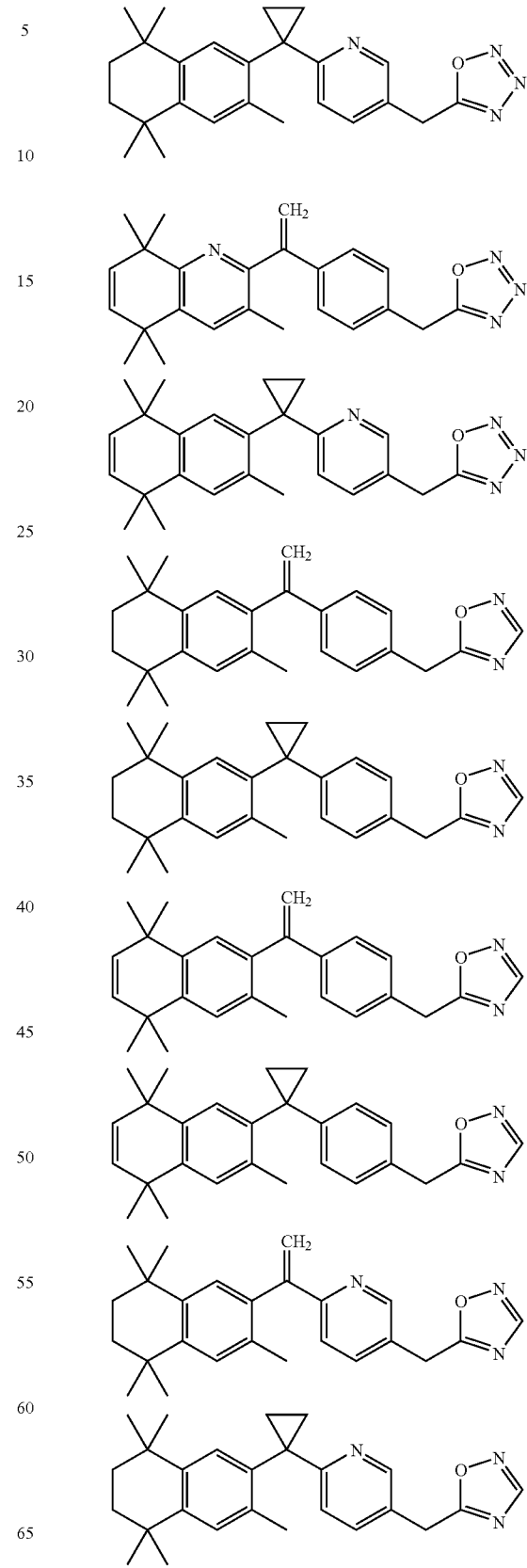

-continued
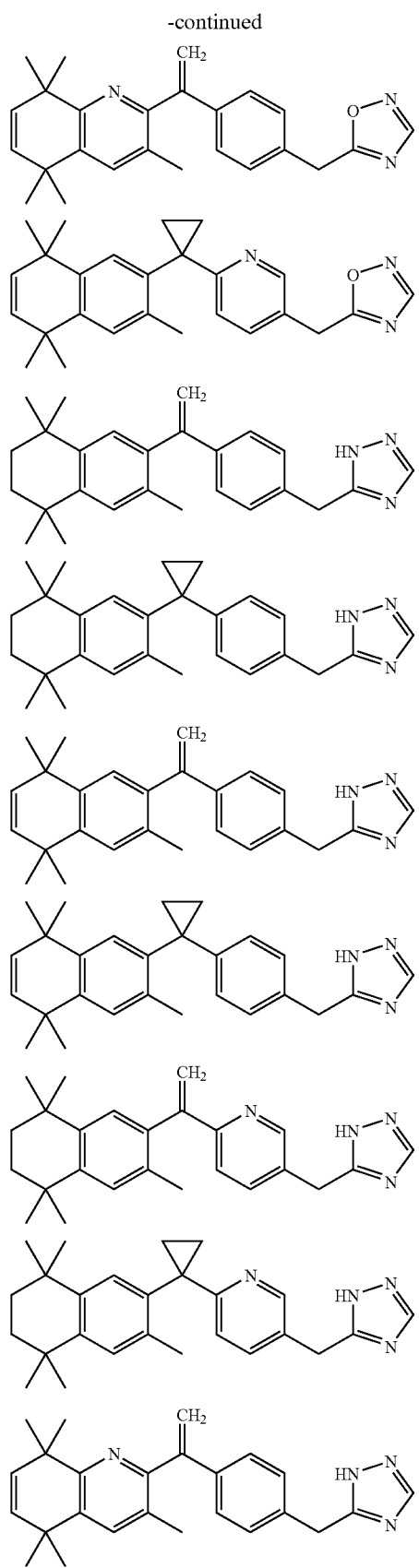
-continued
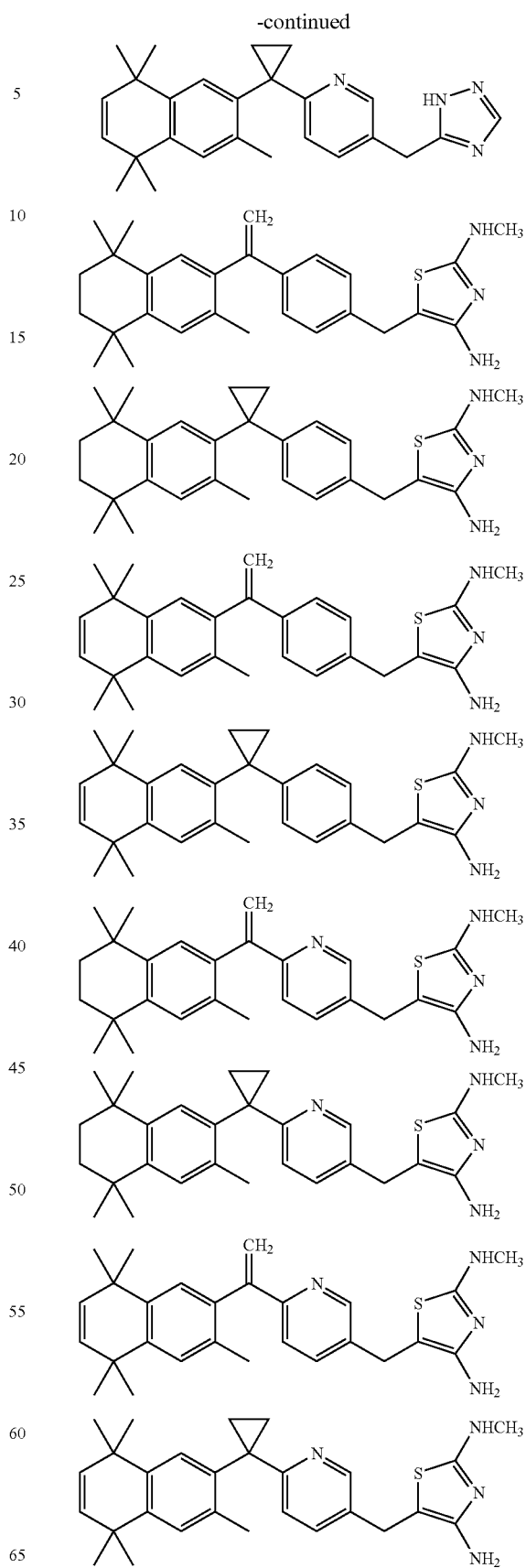

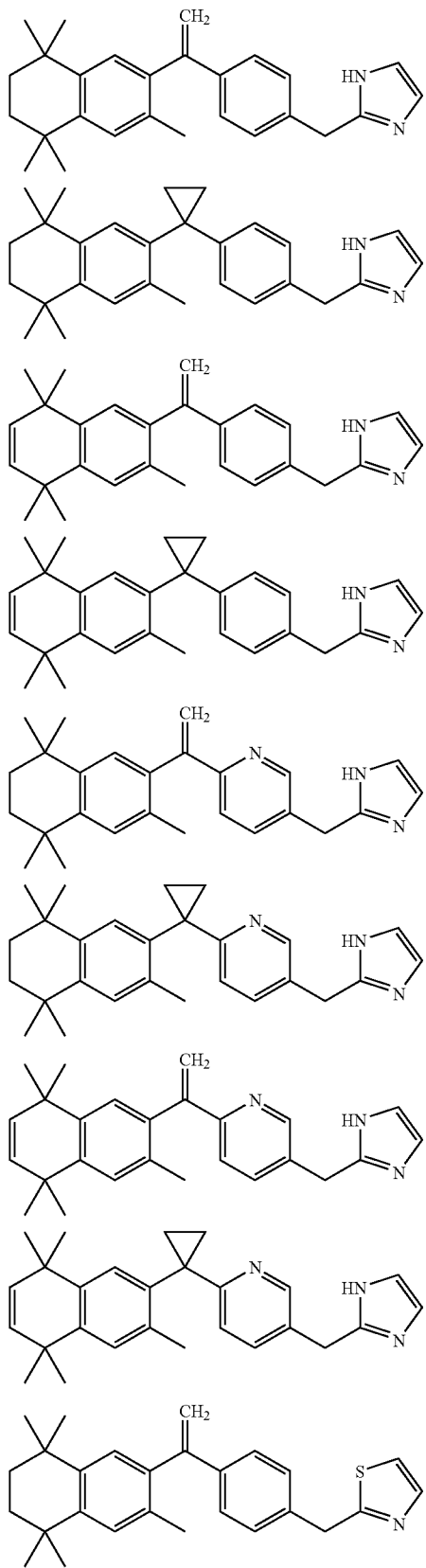
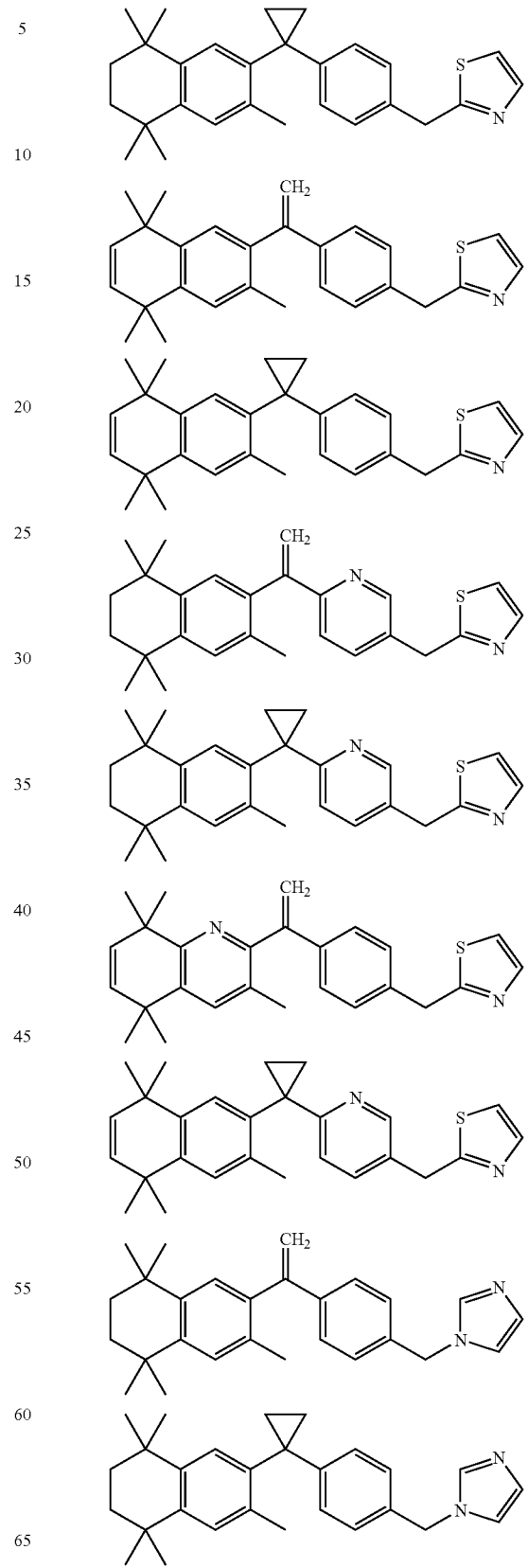

-continued

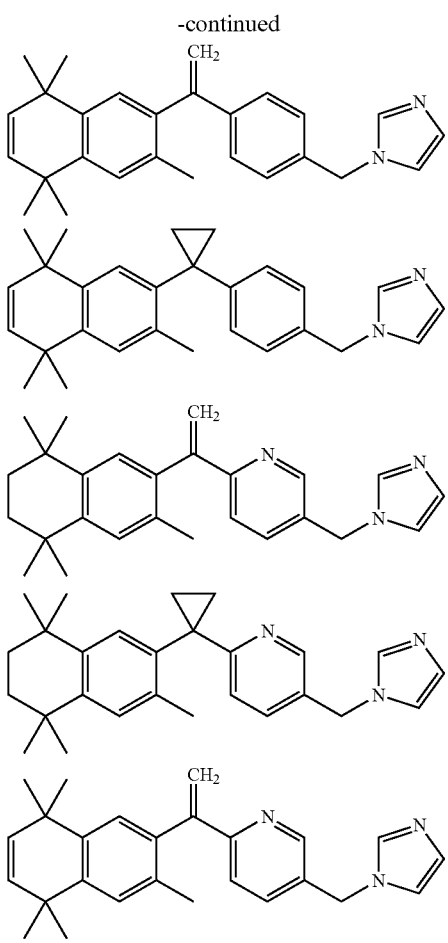

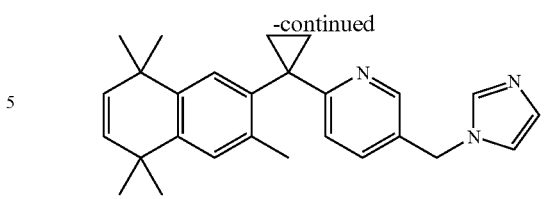

and pharmaceutically acceptable salts thereof.

3. A pharmaceutical composition comprising an effective regulating amount of at least one compound according to claim 1 and a pharmaceutically acceptable vehicle, for control of apoptosis.

4. A pharmaceutical composition comprising at least one compound according to claim 1 in a pharmaceutically acceptable vehicle, for enteral, parenteral, topical, or ocular administration.

5. A pharmaceutical composition comprising at least one compound according to claim 1 in a pharmaceutically acceptable vehicle, for the treatment of cutaneous T-cell lymphoma, squamous cell carcinoma of the head and neck.

6. The pharmaceutical composition according to claim 5, further comprising at least one additional chemotherapeutic agent.

7. The pharmaceutical composition according to claim 6, wherein the additional chemotherapeutic agent is selected from the group consisting of Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Toremifene, Arzoxifene, Raloxifene, and Tamoxifen.

8. The pharmaceutical composition according to claim 6, wherein the additional chemotherapeutic agent is at least one antiestrogenic agent.

* * * * *